United States Patent
Davis et al.

(10) Patent No.: US 12,076,518 B2
(45) Date of Patent: *Sep. 3, 2024

(54) RAPID DELIVERY AND/OR RECEIVING OF FLUIDS

(71) Applicant: YourBio Health, Inc., Medford, MA (US)

(72) Inventors: Shawn Davis, Santa Monica, CA (US); Donald E. Chickering, III, Framingham, MA (US); Ramin Haghgooie, Arlington, MA (US)

(73) Assignee: YourBio Health, Inc., Medford, MA (US)

( * ) Notice: Subject to any disclaimer, the term of this patent is extended or adjusted under 35 U.S.C. 154(b) by 485 days.

This patent is subject to a terminal disclaimer.

(21) Appl. No.: 17/522,878

(22) Filed: Nov. 9, 2021

(65) Prior Publication Data

US 2022/0062607 A1  Mar. 3, 2022

Related U.S. Application Data

(63) Continuation of application No. 15/285,034, filed on Oct. 4, 2016, now Pat. No. 11,202,895, which is a
(Continued)

(51) Int. Cl.
*A61M 37/00* (2006.01)
*A61B 5/15* (2006.01)
(Continued)

(52) U.S. Cl.
CPC ... *A61M 37/0015* (2013.01); *A61B 5/150022* (2013.01); *A61B 5/150221* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS 2,735,671 A  2/1956 Kuhn
2,961,233 A  11/1960 Ullrich
(Continued)

FOREIGN PATENT DOCUMENTS

CN  2065878 U  11/1990
CN  1222334 A  7/1999
(Continued)

OTHER PUBLICATIONS

International Search Report and Written Opinion for PCT/US2011/043698 mailed Feb. 23, 2012.
(Continued)

*Primary Examiner* — Quynh-Nhu H. Vu
(74) *Attorney, Agent, or Firm* — Wolf, Greenfield & Sacks, P.C.

(57) ABSTRACT

The present invention generally relates to systems and methods for delivering and/or receiving a substance or substances such as blood, from subjects, e.g., from the skin and/or from beneath the skin. In one aspect, the present invention is generally directed to devices and methods for receiving or extracting blood from a subject, e.g., from the skin and/or from beneath the skin, using devices containing a fluid transporter (for example, one or more microneedles), and a storage chamber having an internal pressure less than atmospheric pressure prior to receiving blood. In some cases, the device may be self-contained, and in certain instances, the device can be applied to the skin, and activated to receive blood from the subject. The device, or a portion thereof, may then be processed to determine the blood and/or an analyte within the blood, alone or with an external apparatus. For example, blood may be received from the device, and/or the device may contain sensors or agents able to determine the blood and/or an analyte suspected of being contained in the blood. In another aspect, the present inven-
(Continued)

tion is generally directed to arrangements of skin insertion objects such as microneedles and methods of forming and arranging skin insertion objects. Other aspects of the present invention are directed at other devices for receiving blood (or other bodily fluids, e.g., interstitial fluid), kits involving such devices, methods of making such devices, methods of using such devices, and the like.

22 Claims, 16 Drawing Sheets

Related U.S. Application Data continuation of application No. 13/812,248, filed as application No. PCT/US2011/043698 on Jul. 12, 2011, now abandoned.

(60) Provisional application No. 61/367,607, filed on Jul. 26, 2010.

(51) Int. Cl.
*A61B 5/151* (2006.01)
*A61B 5/157* (2006.01)

(52) U.S. Cl.
CPC .. *A61B 5/150229* (2013.01); *A61B 5/150282* (2013.01); *A61B 5/150427* (2013.01); *A61B 5/150435* (2013.01); *A61B 5/150503* (2013.01); *A61B 5/150511* (2013.01); *A61B 5/150984* (2013.01); *A61B 5/15113* (2013.01); *A61B 5/15144* (2013.01); *A61B 5/157* (2013.01); *A61B 5/150526* (2013.01); *A61M 2037/0023* (2013.01); *A61M 2037/0046* (2013.01); *A61M 2037/0053* (2013.01); *Y10T 29/4998* (2015.01)

(58) Field of Classification Search
CPC ............ A61M 2037/0061; A61M 1/38; A61M 2037/0007; A61M 5/00
See application file for complete search history.

(56) References Cited

U.S. PATENT DOCUMENTS

| | | |
|---|---|---|
| 2,976,735 A | 3/1961 | Witte |
| 3,060,429 A | 10/1962 | Winston |
| 3,072,122 A | 1/1963 | Rosenthall |
| 3,339,546 A | 9/1967 | Chen |
| 3,519,171 A | 7/1970 | Kinnavy |
| 3,551,554 A | 12/1970 | Herschler |
| 3,601,861 A | 8/1971 | Moriwaki |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,753,432 A | 8/1973 | Guerra |
| 3,761,013 A | 9/1973 | Schuster |
| 3,908,657 A | 9/1975 | Kowarski |
| 3,964,482 A | 6/1976 | Gerstel et al. |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,280,509 A | 7/1981 | Bethkenhagen et al. |
| 4,329,999 A | 5/1982 | Phillips |
| 4,340,067 A | 7/1982 | Rattenborg |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,572,210 A | 2/1986 | McKinnon |
| 4,615,697 A | 10/1986 | Robinson |
| 4,621,268 A | 11/1986 | Keeling et al. |
| 4,627,445 A | 12/1986 | Garcia et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,855,989 A | 8/1989 | Gyger |
| 4,856,533 A | 8/1989 | Anraku et al. |
| 4,863,970 A | 9/1989 | Patel et al. |
| 4,883,068 A | 11/1989 | Dechow |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,014,718 A | 5/1991 | Mitchen |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,145,565 A | 9/1992 | Kater et al. |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,238,655 A | 8/1993 | Laible et al. |
| 5,279,294 A | 1/1994 | Anderson et al. |
| 5,305,746 A * | 4/1994 | Fendrock ............... A61B 5/257 600/391 |
| 5,320,607 A | 6/1994 | Ishibashi |
| 5,342,397 A | 8/1994 | Guido |
| 5,379,895 A | 1/1995 | Foslien |
| 5,402,798 A | 4/1995 | Swierczek et al. |
| 5,415,177 A | 5/1995 | Zadini et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,504,011 A | 4/1996 | Gavin et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,591,403 A | 1/1997 | Gavin et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,701,910 A | 12/1997 | Powles et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,800,781 A | 9/1998 | Gavin et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |

(56) References Cited

U.S. PATENT DOCUMENTS

| | | |
|---|---|---|
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,897,508 A | 4/1999 | Konrad |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,972,386 A | 10/1999 | Burgoyne |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,024,710 A | 2/2000 | Miller et al. |
| 6,027,459 A | 2/2000 | Shain et al. |
| 6,040,135 A | 3/2000 | Tyrell |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,133,318 A | 10/2000 | Hart |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 * | 5/2001 | Cormier ............ A61B 5/150099 604/20 |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,261,245 B1 | 7/2001 | Kawai et al. |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,315,951 B1 | 11/2001 | Markart |
| 6,319,210 B1 | 11/2001 | Douglas et al. |
| 6,322,574 B1 | 11/2001 | Lloyd |
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,317 B1 | 4/2002 | Kintzig et al. |
| 6,379,324 B1 | 4/2002 | Gartstein et al. |
| 6,391,471 B1 | 5/2002 | Hiraoka et al. |
| 6,394,952 B1 | 5/2002 | Anderson et al. |
| 6,406,919 B1 | 6/2002 | Tyrrell |
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |

(56) References Cited

U.S. PATENT DOCUMENTS

| | | | |
|---|---|---|---|
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,925,317 B1 | 8/2005 | Samuels et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,351 B2 | 11/2005 | Knoll |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,025,774 B2 | 4/2006 | Freeman et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,131,987 B2 | 11/2006 | Sherman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,172,071 B2 | 2/2007 | Hawkins |
| 7,174,199 B2 | 2/2007 | Berner et al. |
| 7,182,910 B2 | 2/2007 | Allen et al. |
| 7,185,764 B2 | 3/2007 | Lee et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 * | 1/2008 | Lastovich ............ A61M 31/002 |
| | | | 604/290 |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,556,615 B2 | 7/2009 | Pettis et al. |
| 7,572,237 B2 | 8/2009 | Saikley et al. |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,236 B2 | 10/2010 | List et al. |
| 7,811,302 B2 | 10/2010 | Steg |
| 7,833,172 B2 | 11/2010 | Hein et al. |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,058,077 B2 | 11/2011 | Groll et al. |
| 8,071,384 B2 | 12/2011 | Burke et al. |
| 8,075,826 B2 * | 12/2011 | Lastovich ............ A61B 17/205 |
| | | | 264/320 |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,246,582 B2 | 8/2012 | Angel et al. |
| 8,344,028 B2 | 1/2013 | Xu et al. |
| 8,383,044 B2 | 2/2013 | Davis et al. |
| 8,396,529 B2 * | 3/2013 | Lee ............................ A61B 5/25 |
| | | | 607/139 |
| 8,440,085 B2 | 5/2013 | Bormann et al. |
| 8,460,210 B2 | 6/2013 | Jacobs |
| 8,465,425 B2 | 6/2013 | Heller et al. |
| 8,517,938 B2 | 8/2013 | Eisenhardt et al. |
| 8,523,894 B2 | 9/2013 | Schmelzeisen-Redeker et al. |
| 8,530,231 B2 | 9/2013 | Nakae et al. |
| 8,561,795 B2 | 10/2013 | Schott |
| 8,628,724 B2 | 1/2014 | Kunstner |
| 8,647,575 B2 | 2/2014 | Ohashi |
| 8,808,202 B2 | 8/2014 | Brancazio |
| 8,821,412 B2 | 9/2014 | Gonzalez-Zugasti et al. |
| 8,821,446 B2 | 9/2014 | Trautman et al. |
| 8,827,971 B2 | 9/2014 | Chickering, III et al. |
| 8,870,903 B2 | 10/2014 | LeVaughn et al. |
| 8,882,794 B2 | 11/2014 | Lum |
| 8,900,180 B2 | 12/2014 | Wolter et al. |
| 8,934,955 B2 | 1/2015 | Schraga |
| 8,971,980 B2 | 3/2015 | Mace et al. |
| 9,028,426 B2 | 5/2015 | List et al. |
| 9,033,898 B2 | 5/2015 | Chickering, III et al. |
| 9,033,989 B2 | 5/2015 | Wolfson et al. |
| 9,039,638 B2 | 5/2015 | Arnitz |
| 9,041,541 B2 | 5/2015 | Levinson et al. |
| 9,101,302 B2 | 8/2015 | Mace et al. |
| 9,113,836 B2 | 8/2015 | Bernstein et al. |
| 9,119,578 B2 | 9/2015 | Haghgooie et al. |
| 9,295,417 B2 | 3/2016 | Haghgooie et al. |
| 9,730,624 B2 | 8/2017 | Gonzalez-Zugasti et al. |
| 9,763,590 B1 * | 9/2017 | Rood .................... A61B 5/291 |
| 9,775,551 B2 | 10/2017 | Bernstein et al. |
| 10,188,335 B2 | 1/2019 | Haghgooie et al. |
| 10,543,310 B2 | 1/2020 | Bernstein et al. |
| 10,799,166 B2 | 10/2020 | Gonzalez-Zugasti et al. |
| 10,835,163 B2 | 11/2020 | Haghgooie et al. |
| 10,939,860 B2 | 3/2021 | Levinson et al. |
| 11,177,029 B2 | 11/2021 | Levinson et al. |
| 11,202,895 B2 | 12/2021 | Davis et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0076443 A1 | 6/2002 | Stein et al. |
| 2002/0077584 A1 | 6/2002 | Lin et al. |
| 2002/0082543 A1 | 6/2002 | Park et al. |
| 2002/0087056 A1 | 7/2002 | Aceti et al. |
| 2002/0099308 A1 | 7/2002 | Bojan et al. |
| 2002/0099356 A1 | 7/2002 | Unger et al. |
| 2002/0112981 A1 | 8/2002 | Cooper et al. |
| 2002/0115967 A1 | 8/2002 | Svedman |
| 2002/0119136 A1 | 8/2002 | Johansen |
| 2002/0130042 A1 | 9/2002 | Moerman et al. |
| 2002/0130093 A1 | 9/2002 | Ferrara et al. |
| 2002/0138049 A1 | 9/2002 | Allen |
| 2002/0143320 A1 | 10/2002 | Levin |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0187556 A1 | 12/2002 | Shartle et al. |
| 2002/0188221 A1 | 12/2002 | Sohrab |
| 2003/0004437 A1 | 1/2003 | Collins et al. |
| 2003/0040682 A1 | 2/2003 | Tapper |
| 2003/0055326 A1 | 3/2003 | Sohrab |
| 2003/0065294 A1 | 4/2003 | Pickup et al. |
| 2003/0083618 A1 | 5/2003 | Angel et al. |
| 2003/0083645 A1 | 5/2003 | Angel et al. |
| 2003/0083685 A1 | 5/2003 | Freeman et al. |
| 2003/0083686 A1 | 5/2003 | Freeman et al. |
| 2003/0100846 A1 | 5/2003 | Custer et al. |
| 2003/0109807 A1 | 6/2003 | Knoll |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |

(56) References Cited

U.S. PATENT DOCUMENTS

| | | |
|---|---|---|
| 2003/0135333 A1 | 7/2003 | Aceti et al. |
| 2003/0143746 A1 | 7/2003 | Sage |
| 2003/0159615 A1 | 8/2003 | Anderson et al. |
| 2003/0162304 A1 | 8/2003 | Dority et al. |
| 2003/0181863 A1 | 9/2003 | Ackley et al. |
| 2003/0187394 A1 | 10/2003 | Wilkinson et al. |
| 2003/0187395 A1 | 10/2003 | Gabel et al. |
| 2003/0195398 A1 | 10/2003 | Suzuki et al. |
| 2003/0204148 A1 | 10/2003 | Lange et al. |
| 2003/0208138 A1 | 11/2003 | Olson |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0053894 A1 | 3/2004 | Mazess et al. |
| 2004/0058458 A1 | 3/2004 | Anker et al. |
| 2004/0087990 A1 | 5/2004 | Boecker et al. |
| 2004/0096959 A1 | 5/2004 | Stiene et al. |
| 2004/0098009 A1 | 5/2004 | Boecker et al. |
| 2004/0102717 A1 | 5/2004 | Qi |
| 2004/0106904 A1 | 6/2004 | Gonnelli et al. |
| 2004/0133126 A1 | 7/2004 | McNenny |
| 2004/0137640 A1 | 7/2004 | Hirao et al. |
| 2004/0138688 A1 | 7/2004 | Giraud |
| 2004/0162521 A1 | 8/2004 | Bengtsson |
| 2004/0163987 A1 | 8/2004 | Allen |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0000514 A1 | 1/2005 | Sullivan et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0033197 A1 | 2/2005 | Cottler |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0090766 A1 | 4/2005 | Montanari |
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0215923 A1 | 9/2005 | Wiegel |
| 2005/0221276 A1 | 10/2005 | Rozakis et al. |
| 2005/0227269 A1 | 10/2005 | Lloyd, Jr. et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2005/0267422 A1 | 12/2005 | Kriesel |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0015061 A1* | 1/2006 | Kuo ............... A61M 37/0015 604/47 |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0089566 A1 | 4/2006 | DeHart |
| 2006/0091669 A1 | 5/2006 | Wilkinson |
| 2006/0100654 A1 | 5/2006 | Fukuda et al. |
| 2006/0129065 A1 | 6/2006 | Matsumoto et al. |
| 2006/0142651 A1 | 6/2006 | Brister et al. |
| 2006/0157362 A1 | 7/2006 | Schraga |
| 2006/0173261 A1* | 8/2006 | Kall ................ A61B 5/296 600/372 |
| 2006/0182738 A1 | 8/2006 | Holmes et al. |
| 2006/0189895 A1 | 8/2006 | Neel et al. |
| 2006/0200046 A1 | 9/2006 | Windus-Smith et al. |
| 2006/0202385 A1 | 9/2006 | Xu et al. |
| 2006/0228259 A1 | 10/2006 | Samsoondar |
| 2006/0257883 A1 | 11/2006 | Bjorkaker et al. |
| 2006/0258959 A1 | 11/2006 | Sode |
| 2006/0259195 A1 | 11/2006 | Eliuk et al. |
| 2006/0264779 A1 | 11/2006 | Kemp et al. |
| 2006/0264782 A1 | 11/2006 | Holmes et al. |
| 2007/0004989 A1* | 1/2007 | Dhillon ............ A61B 5/150022 600/583 |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078376 A1* | 4/2007 | Smith ................ A61N 1/30 604/21 |
| 2007/0078414 A1 | 4/2007 | McAllister et al. |
| 2007/0083131 A1 | 4/2007 | Escutia et al. |
| 2007/0088248 A1 | 4/2007 | Glenn et al. |
| 2007/0092637 A1 | 4/2007 | Brown et al. |
| 2007/0093864 A1 | 4/2007 | Pugh |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161926 A1 | 7/2007 | Imamura et al. |
| 2007/0161964 A1* | 7/2007 | Yuzhakov ......... A61M 37/0015 604/272 |
| 2007/0167340 A1 | 7/2007 | Barthel et al. |
| 2007/0169411 A1 | 7/2007 | Thiessen et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0185515 A1 | 8/2007 | Stout |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2007/0270672 A1 | 11/2007 | Hayter |
| 2007/0272738 A1 | 11/2007 | Berkun |
| 2007/0275193 A1 | 11/2007 | deSimone et al. |
| 2008/0009763 A1* | 1/2008 | Chiou ................ A61B 5/266 600/393 |
| 2008/0014627 A1 | 1/2008 | Merchant et al. |
| 2008/0021491 A1 | 1/2008 | Freeman et al. |
| 2008/0033319 A1 | 2/2008 | Kloepfer et al. |
| 2008/0051689 A1 | 2/2008 | Gura et al. |
| 2008/0077096 A1 | 3/2008 | Nakamura et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0103434 A1 | 5/2008 | Lastovich et al. |
| 2008/0108958 A1 | 5/2008 | Carter et al. |
| 2008/0108959 A1 | 5/2008 | Jung et al. |
| 2008/0112886 A1 | 5/2008 | Mitragotri et al. |
| 2008/0125673 A1 | 5/2008 | Carano et al. |

(56) References Cited

U.S. PATENT DOCUMENTS

| | | |
|---|---|---|
| 2008/0125743 A1* | 5/2008 | Yuzhakov ......... A61M 37/0015 604/506 |
| 2008/0129486 A1 | 6/2008 | Jeckelmann et al. |
| 2008/0138583 A1* | 6/2008 | Bhandari ......... A61M 37/0015 428/156 |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183140 A1 | 7/2008 | Paproski et al. |
| 2008/0183144 A1 | 7/2008 | Trautman et al. |
| 2008/0199851 A1 | 8/2008 | Egan et al. |
| 2008/0200791 A1 | 8/2008 | Simpson et al. |
| 2008/0200838 A1 | 8/2008 | Goldberger et al. |
| 2008/0217391 A1 | 9/2008 | Roof et al. |
| 2008/0220411 A1 | 9/2008 | McNaughton et al. |
| 2008/0221407 A1 | 9/2008 | Baker |
| 2008/0267537 A1 | 10/2008 | Thuries |
| 2008/0269666 A1 | 10/2008 | Wang et al. |
| 2008/0269685 A1* | 10/2008 | Singh ................ A61K 9/0021 604/173 |
| 2008/0275327 A1 | 11/2008 | Faarbaek et al. |
| 2008/0275378 A1 | 11/2008 | Herndon |
| 2008/0281290 A1 | 11/2008 | Yodfat et al. |
| 2008/0283603 A1 | 11/2008 | Barron et al. |
| 2008/0300508 A1 | 12/2008 | Tomer |
| 2008/0315994 A1 | 12/2008 | Maltseff et al. |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0048536 A1 | 2/2009 | Freeman et al. |
| 2009/0054813 A1 | 2/2009 | Freeman et al. |
| 2009/0054971 A1 | 2/2009 | Mitsunaga et al. |
| 2009/0076453 A1 | 3/2009 | Mejlhede et al. |
| 2009/0088648 A1 | 4/2009 | Jaffe et al. |
| 2009/0099427 A1 | 4/2009 | Jina et al. |
| 2009/0099478 A1 | 4/2009 | Cassells et al. |
| 2009/0099529 A1 | 4/2009 | Anderson et al. |
| 2009/0101447 A1 | 4/2009 | Durham et al. |
| 2009/0105614 A1 | 4/2009 | Momose et al. |
| 2009/0118662 A1 | 5/2009 | Schnall |
| 2009/0124994 A1 | 5/2009 | Roe |
| 2009/0130646 A1 | 5/2009 | Fletcher et al. |
| 2009/0131829 A1 | 5/2009 | Freeman et al. |
| 2009/0155838 A1 | 6/2009 | Hale |
| 2009/0182306 A1 | 7/2009 | Lee et al. |
| 2009/0187117 A1 | 7/2009 | Imai |
| 2009/0187160 A1 | 7/2009 | McAllister et al. |
| 2009/0187167 A1 | 7/2009 | Sexton et al. |
| 2009/0198189 A1 | 8/2009 | Simons et al. |
| 2009/0198215 A1 | 8/2009 | Chong et al. |
| 2009/0206158 A1 | 8/2009 | Thuries et al. |
| 2009/0209883 A1 | 8/2009 | Higgins et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0315684 A1 | 12/2009 | Sacco et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0021947 A1 | 1/2010 | Emery et al. |
| 2010/0022864 A1* | 1/2010 | Cordero ............... A61B 5/291 600/372 |
| 2010/0030111 A1 | 2/2010 | Perriere |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0114014 A1 | 5/2010 | Roser |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0240079 A1 | 9/2010 | Jackson |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0282834 A1 | 11/2010 | Devergne |
| 2010/0292191 A1 | 11/2010 | Mainx et al. |
| 2010/0305518 A1* | 12/2010 | Moga ................ A61M 37/0015 604/272 |
| 2010/0318111 A1 | 12/2010 | Sarna et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0034830 A1 | 2/2011 | Nakamura et al. |
| 2011/0040208 A1 | 2/2011 | Mcminn et al. |
| 2011/0040317 A1 | 2/2011 | Lee et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0112384 A1 | 5/2011 | Eisenhardt et al. |
| 2011/0112438 A1 | 5/2011 | Radzuinas et al. |
| 2011/0125058 A1 | 5/2011 | Levinson et al. |
| 2011/0137203 A1 | 6/2011 | Nishiuchi et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0212453 A1 | 9/2011 | Argarwal et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0281346 A1 | 11/2011 | Halpern et al. |
| 2011/0282173 A1 | 11/2011 | Fonduca et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0089050 A1 | 4/2012 | Fukuda |
| 2012/0123297 A1 | 5/2012 | Brancazio |
| 2012/0184906 A1 | 7/2012 | McAllister |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0006217 A1 | 1/2013 | Hattersley et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0157787 A1 | 6/2015 | Cully et al. |
| 2015/0278476 A1 | 10/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2016/0262676 A1 | 9/2016 | Haghgooie et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |

(56) References Cited

U.S. PATENT DOCUMENTS

| | | |
|---|---|---|
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0132774 A1 | 5/2018 | Gonzalez-Zugasti et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0216380 A1 | 7/2019 | Ivosevic et al. |
| 2019/0336058 A1 | 11/2019 | Haghgooie et al. |
| 2020/0015751 A9 | 1/2020 | Chickering et al. |
| 2020/0085414 A1 | 3/2020 | Berthier et al. |
| 2020/0353155 A1 | 11/2020 | Bernstein et al. |
| 2021/0016070 A1* | 1/2021 | Cho ................ A61M 37/0015 |
| 2021/0022681 A1 | 1/2021 | Chickering et al. |
| 2021/0137435 A1 | 5/2021 | Queval |
| 2021/0228124 A1 | 7/2021 | Gonzalez-Zugasti et al. |
| 2021/0259599 A1 | 8/2021 | Haghgooie et al. |
| 2021/0330227 A1 | 10/2021 | Levinson et al. |
| 2021/0369150 A1 | 12/2021 | Bernstein et al. |

FOREIGN PATENT DOCUMENTS

| | | |
|---|---|---|
| CN | 2331315 Y | 8/1999 |
| CN | 2462854 Y | 12/2001 |
| CN | 2600055 Y | 1/2004 |
| CN | 1499949 A | 5/2004 |
| CN | 1501788 A | 6/2004 |
| CN | 1524493 A | 9/2004 |
| CN | 1551743 A | 12/2004 |
| CN | 1753646 A | 3/2006 |
| CN | 101248998 A | 8/2008 |
| CN | 101347384 A | 1/2009 |
| CN | 101678196 A | 3/2010 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 535 266 A1 | 4/1993 |
| EP | 0 555 554 A1 | 8/1993 |
| EP | 0 803 288 A2 | 10/1997 |
| EP | 1 027 864 A1 | 8/2000 |
| EP | 1 360 934 A1 | 11/2003 |
| EP | 1 522 260 A1 | 4/2005 |
| EP | 1 611 837 A2 | 1/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 1 187 653 B1 | 3/2010 |
| EP | 2 701 601 A1 | 3/2014 |
| EP | 3087919 A1 | 11/2016 |
| FR | 2929135 A1 | 10/2009 |
| JP | 61-198061 A2 | 9/1986 |
| JP | 03-060645 A2 | 3/1991 |
| JP | 4-053536 A2 | 2/1992 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-272710 A | 9/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-517463 A | 6/2005 |
| JP | 2005-522243 | 7/2005 |
| JP | 2005-211189 A | 8/2005 |
| JP | 2005-525141 A | 8/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-521555 A | 9/2006 |
| JP | 2006-280912 A | 10/2006 |
| JP | 2007-209549 A | 8/2007 |
| JP | 2007-209747 A | 8/2007 |
| JP | 2007-236686 | 9/2007 |
| JP | 2007-526460 A | 9/2007 |
| JP | 2008-022988 A | 2/2008 |
| JP | 2008-54884 A | 3/2008 |
| JP | 2008-079853 A | 4/2008 |
| JP | 2008-099988 A | 5/2008 |
| JP | 2008-099992 A | 5/2008 |
| JP | 2008-518662 A | 6/2008 |
| JP | 2008-534192 A | 8/2008 |
| JP | 2009-504273 A | 2/2009 |
| JP | 2009-509679 A | 3/2009 |
| JP | 2009-066385 A | 4/2009 |
| JP | 2009-078173 A | 4/2009 |
| JP | 2009-519064 A | 5/2009 |
| JP | 2009-254899 A2 | 8/2009 |
| JP | 2010-520036 A | 6/2010 |
| JP | 2011-511660 A | 4/2011 |
| JP | 2011-522593 A | 8/2011 |
| JP | 2014-516645 A | 7/2014 |
| KR | 2003-0061753 A | 7/2003 |
| WO | WO 92/02175 A1 | 2/1992 |
| WO | WO 92/04867 A1 | 4/1992 |
| WO | WO 93/00043 A1 | 1/1993 |
| WO | WO 95/10223 A2 | 4/1995 |
| WO | WO 95/15783 A1 | 6/1995 |
| WO | WO 97/48442 A1 | 12/1997 |
| WO | WO 99/27852 A1 | 6/1999 |
| WO | WO 99/59657 A1 | 11/1999 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/000101 A2 | 1/2002 |
| WO | WO 02/00101 A2 | 1/2002 |
| WO | WO 02/05890 A2 | 1/2002 |
| WO | WO 02/30301 A1 | 4/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 02/100460 A2 | 12/2002 |
| WO | WO 02/101359 A2 | 12/2002 |
| WO | WO 03/026611 A2 | 4/2003 |
| WO | WO 03/030984 A2 | 4/2003 |
| WO | WO 03/039632 A2 | 5/2003 |
| WO | WO 2003/037403 A1 | 5/2003 |
| WO | WO 03/070099 A1 | 8/2003 |
| WO | WO 03/082091 A2 | 10/2003 |
| WO | WO 2003/083469 A2 | 10/2003 |
| WO | WO 04/006982 A3 | 1/2004 |
| WO | WO 04/085995 A2 | 10/2004 |
| WO | WO 2005/000118 A1 | 1/2005 |
| WO | WO 2005/025413 A2 | 3/2005 |
| WO | WO 2005/095965 A1 | 10/2005 |
| WO | WO 2005/123173 A1 | 12/2005 |
| WO | WO 2006/019823 A2 | 2/2006 |
| WO | WO 2006/050032 A2 | 5/2006 |
| WO | WO 2006/105968 A1 | 10/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A1 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/073870 A2 | 7/2007 |
| WO | WO 2007/079530 A1 | 7/2007 |

(56) References Cited

FOREIGN PATENT DOCUMENTS

| WO | WO 2007/091671 A1 | 8/2007 |
|---|---|---|
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/062032 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/008267 A1 | 1/2009 |
| WO | WO 2009/027950 A2 | 3/2009 |
| WO | WO 2009/071775 A1 | 6/2009 |
| WO | WO 2009/101112 A1 | 8/2009 |
| WO | WO 2009/126653 A1 | 10/2009 |
| WO | WO 2009/145920 A1 | 12/2009 |
| WO | WO 2009/148624 A1 | 12/2009 |
| WO | WO 2009/149308 A2 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | WO 2012/149134 A1 | 11/2012 |
| WO | WO 2014/160893 A2 | 10/2014 |
| WO | WO 2014/172246 A1 | 10/2014 |
| WO | WO 2017/191221 A1 | 11/2017 |

OTHER PUBLICATIONS

International Preliminary Report on Patentability for PCT/US2011/043698 mailed Feb. 7, 2013.
[No Author Listed] Air-Tite Products Co., Inc.—Luer Lock. Oct. 14, 2008. Retrieved from the Internet: https://web.archive.org/web/20081023203858/https://www.air-tite-shop.com/c-7-luer-lock.aspx on Aug. 28, 2019. 2 pages.
[No Author Listed] Air-Tite Products Co., Inc.—Luer Slip. Oct. 14, 2008. Retrieved from the Internet: https://web.archive.org/web/20081014224752/https://www.air-tite-shop.com/c-6-luer-slip.aspx on Aug. 28, 2019. 2 pages.
[No Author Listed] Greiner Bio-One Preanalytics Catalogue. www.gbo.com/preanalytics. Feb. 2012. 76 pages.
Angell et al., Silicon Micromechanical Devices. Scientific American. Apr. 1983;248:44-55.
Baroli, Penetration of metallic nanoparticles in human full-thickness skin. J. Ind. Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Matriano et al., Macroflux microprojection array patch technology: a new and efficient approach for intracutaneous immunization. Pharm Res. Jan. 2002;19(1):63-70.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990; 12(2):O494-95. (The year of publication is sufficiently earlier than the effective U.S. filing date and any foreign priority date so that the particular month of publication is not in issue. See MPEP 609.04(a)).
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.

\* cited by examiner

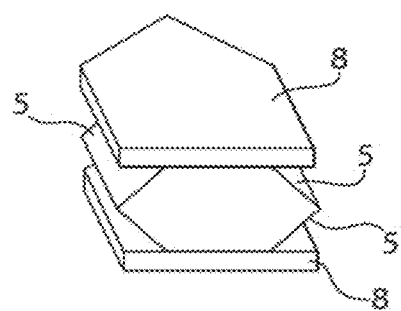
Fig. 19
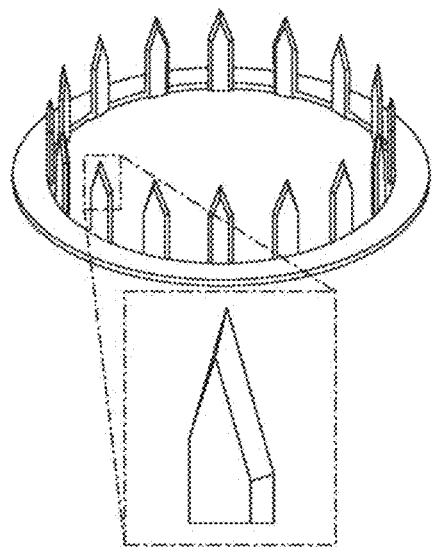 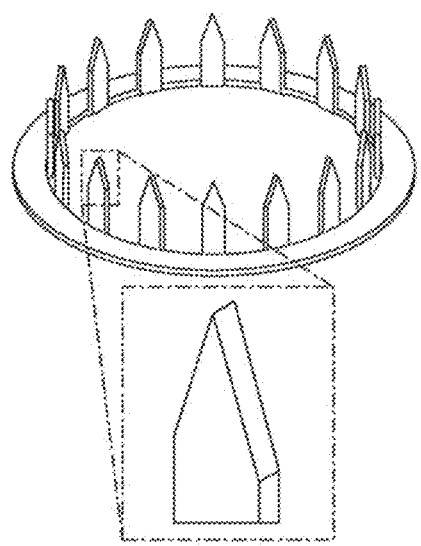
Fig. 20    Fig. 21

RAPID DELIVERY AND/OR RECEIVING OF FLUIDS

RELATED APPLICATIONS

This application is a continuation of U.S. patent application Ser. No. 15/285,034, filed Oct. 4, 2016, which is a continuation of U.S. patent application Ser. No. 13/812,248, filed Jul. 12, 2011, which is a national stage filing under 35 U.S.C. § 371 of International Application No. PCT/US2011/043698, filed Jul. 12, 2011, which claims the benefit of U.S. Provisional Patent Application Ser. No. 61/367,607, filed Jul. 26, 2010.

FIELD OF INVENTION

The present invention generally relates to systems and methods for delivering and/or receiving a substance or substances such as blood and/or drugs, with respect to subjects, e.g., at and/or beneath the skin, and in some cases, with relatively little pain.

BACKGROUND

Phlebotomy or venipuncture is the process of obtaining intravenous access for the purpose of intravenous therapy or obtaining a sample of venous blood. This process is typically practiced by medical practitioners, including paramedics, phlebotomists, doctors, nurses, and the like. Substantial equipment is needed to obtain blood from a subject, including the use of evacuated (vacuum) tubes, e.g., such as the Vacutainer™ (Becton, Dickinson and company) and Vacuette™ (Greiner Bio-One GmBH) systems. Other equipment includes hypodermic needles, syringes, and the like. However, such procedures are complicated and require sophisticated training of practitioners, and often cannot be done in non-medical settings. Accordingly, improvements in methods of obtaining blood or other fluids from the skin are still needed.

SUMMARY OF THE INVENTION

The present invention generally relates to systems and methods for delivering and/or receiving a substance or substances such as blood, from subjects, e.g., from the skin and/or from beneath the skin. The subject matter of the present invention involves, in some cases, interrelated products, alternative solutions to a particular problem, and/or a plurality of different uses of one or more systems and/or articles.

In one aspect of the invention, microneedles in an array may be arranged to maximize a density of microneedles per unit area of the array. For example, a number of microneedles in a circular array according to one embodiment of the invention may be about two times the number of microneedles in a rectangular array having the same footprint size. Improved density may be achieved in some embodiments by having microneedles arranged (while the microneedles are lying in a common plane and prior to bending a penetrating portion of the needles upward from the plane) so that the microneedles generally "point" towards at least one other microneedle in the array and such that the microneedles are generally not parallel with each other. For example, in one embodiment, a method for forming an array of microneedles may include steps of providing a layer of material having opposed substantially planar sides, and etching the layer of material to define a plurality of microneedles. The microneedles may be formed from the layer such that bases of the microneedles are arranged at a periphery of a closed loop and each of the microneedles extends toward a center of the closed loop. Since the microneedles in this illustrative embodiment may point radially inwardly, the microneedles will generally not be parallel with each other (although some needles may be parallel with one or more other needles). This configuration has been found to make efficient use of material in the layer and provide a higher total number of microneedles for a given area than other arrangements, such as a rectangular array in which the microneedles are all parallel to each other. After forming the microneedles from the layer, the penetrating portions of the microneedles may be bent away from the bases (i.e., out of the common plane of the layer) so that the penetrating portions are arranged for insertion into skin or other material. That is, the penetrating portions may be bent upwardly from the common plane of the layer so that the penetrating portions are arranged at an angle relative to the plane of the closed loop.

In another illustrative embodiment, an array of microneedles may include a plurality of microneedles that each include a base portion and a penetrating portion. The base portions of the plurality of needles may be arranged at the periphery of a closed loop lying in a common plane, and the penetrating portions may extend at an angle away from the plane of the closed loop. Such an arrangement may help improve a packing density of needles for the array, e.g., by allowing the needles to be formed from a sheet of material while making efficient use of the material, and/or provide for an array with improved material transfer properties, e.g., by allowing the microneedles to provide a flow channel for fluid exiting from skin penetrated by the needles.

In another aspect of the invention, the microneedle arrangement includes a first plurality of microneedles that each include a base portion and a penetrating portion, the base portions of the first plurality of microneedles being arranged at the periphery of a first closed loop lying in a plane, the penetrating portions of the first plurality of microneedles each extending at a respective angle away from the plane of the first closed loop. The arrangement also includes a second plurality of microneedles that each include a base portion and a penetrating portion, the base portions of the second plurality of microneedles being arranged at a periphery of a second closed loop lying in the plane, the second closed loop being larger than, and surrounding, the first closed loop, the penetrating portions of the second plurality of microneedles each extending at a respective angle away from the plane of the second closed loop. This arrangement may further increase the packing density of needles. In some illustrative embodiments, the closed loops are circles. In one illustrative embodiment, the closed loops are concentric circles.

In another aspect of the invention, a method for forming a microneedle arrangement includes providing a layer of material having opposed substantially planar sides, etching the layer of material to define a plurality of microneedles such that bases of the microneedles are arranged at a periphery of a first closed loop and each of the microneedles extends toward a center of the first closed loop, and etching the layer of material to define a second plurality of microneedles with bases arranged at a periphery of a second closed loop that is arranged around the first closed loop.

In one aspect, the present invention is generally directed to microneedles for insertion into the skin for the purpose of delivering therapeutics, such as medicines, drugs, etc., or receiving fluids, such as blood or interstitial fluid. For example, microneedles may be inserted into skin and then withdrawn, allowing blood or other fluid to flow from the skin. In other arrangements, the microneedles may remain in the skin after insertion (at least temporarily), and be coated, have one or more channels, be capable of degrading or dissolving, or otherwise be arranged to allow fluid to flow from the skin. In one embodiment, microneedles may include a tip having a point that serves as a leading contact surface. Providing a leading contact surface on a microneedle in the form of a point may help reduce a force needed to insert the microneedle into skin or other material, may help the microneedle maintain a straight or other desired trajectory when passing through skin, and/or other features. In one embodiment, the point may be formed at the intersection of four or more surfaces and may reduce a force needed to insert the needle into skin or other material. In another embodiment, a microneedle may have a knife edge, e.g., at least a portion of the edge of the microneedle may be formed by beveled surfaces. The knife edge may have a V-shape and may be symmetrical or asymmetrical. The knife edge may be formed using an etching process, e.g., an isotropic chemical etching process used in combination with a photolithographic patterning or other lithographic patterning process to form the microneedles from a layer of metal or other material.

In yet another aspect, the invention is directed to a kit. In one set of embodiments, the kit includes a fluid sample device comprising a fluid transporter for receiving fluid from the subject and a storage chamber for receiving fluid withdrawn from the subject via the fluid transporter, and an external analytical apparatus having a port for mating with a port on the fluid sample device.

In another aspect, the present invention is directed to a method of making one or more of the embodiments described herein, for example, devices for receiving blood from a subject. In another aspect, the present invention is directed to a method of using one or more of the embodiments described herein, for example, devices for receiving blood from a subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 18 and 19 schematically show two steps in a method for forming microneedles in an illustrative embodiment;

FIG. 20 shows an illustrative array of microneedles in which each microneedle has the configuration as shown in FIG. 14;

FIG. 21 shows an illustrative array of microneedles in which each microneedle has the configuration as shown in FIG. 13;

DETAILED DESCRIPTION

Figure 1A:
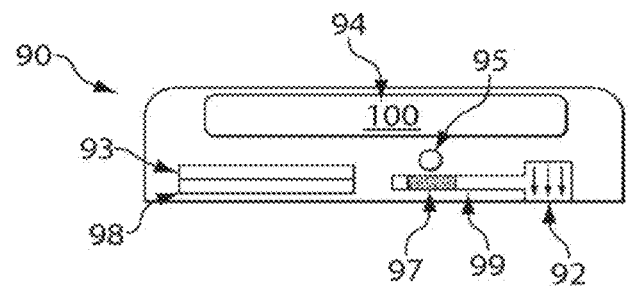
FIGS. 1A-1B illustrate devices according to certain embodiments of the invention.

The present invention generally relates to systems and methods for receiving a substance from a subject, e.g. received from the skin and/or from beneath the skin of the subject, and/or for delivering a substance to a subject, e.g. delivering a substance to the skin and/or to a location beneath the skin of a subject. Throughout the application, the phrase "from the skin" is used to mean from the top or outer surface of the skin, from within the skin, and/or from beneath the skin. Likewise, "to the skin" is used to mean to the top or outer surface of the skin, to within the skin, and/or to beneath the skin. The device, in some cases, may be interfaced with external equipment to determine an analyte contained within a fluid contained within or collected by the device. For example, the device may be mounted on an external holder, the device may include a port for transporting fluid out of the device, the device may include a window for interrogating a fluid contained within the device, or the like.

The received fluid may be any suitable bodily fluid, such as interstitial fluid, other skin-associated material, mucosal material or fluid, whole blood, perspiration, saliva, plasma, tears, lymph, urine, plasma, or any other bodily fluid, or combinations thereof. Substances received from a subject can include solid or semi-solid material such as skin, cells, or any other substance from the subject. Substances that can be delivered to a subject in accordance with some embodiments of the invention include diagnostic substances, therapeutic substances such as drugs, and the like. Various embodiments of the invention are described below in the context of delivering or receiving a fluid, such as blood, from or through the skin. It is to be understood that in all embodiments herein, regardless of the specific exemplary language used (e.g., receiving blood), the devices and methods of other embodiments of the invention can be used for receiving any substance from the skin and/or from beneath the skin of the subject, and/or for delivering any substance to the subject, e.g. to the skin and/or a location beneath the skin of the subject.

In one aspect, the present invention is generally directed to devices and methods for receiving or extracting blood or other bodily fluids from a subject, e.g., from the skin and/or from beneath the skin, using devices having a substance transfer component (which may include, for example, one or more microneedles and/or other skin insertion objects). The device may also contain, in some embodiments, a storage chamber having an internal pressure less than atmospheric pressure prior to receiving blood or other bodily fluids. In some cases, the device may pierce the skin of the subject, and fluid can then be delivered and/or received from the subject. The subject is usually human, although non-human subjects may be used in certain instances, for instance, other mammals such as a dog, a cat, a horse, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like.

In some cases, the device can be applied to the skin, and activated to receive fluid from the subject. The device, or a portion thereof, may then be processed to determine the fluid and/or an analyte within the fluid, alone or with an external apparatus. For example, fluid may be received from the device, and/or the device may contain sensors or agents able to determine the fluid and/or an analyte suspected of being contained in the fluid.

The inventors have appreciated that the performance of microneedles or other skin insertion objects when inserted into skin to receive fluids, or to deliver therapeutics or fluids, depends on the mechanical stability and sharpness of the needles used, and that the force needed to insert microneedles into skin depends on the interfacial area between the microneedle tip and the skin contact surface. That is, needles for some applications should have a suitably small interfacial area to reduce the force needed to insert the needles into skin, and be strong enough to withstand the force so as to prevent breaking or bending of the needles. Also, an amount of fluid received or delivered via the needles depends on the cross sectional area and number of microneedles within a given array, as well as the length of the needles. In some aspects of the invention, provided microneedles have a reduced interfacial area (i.e., increased sharpness) and an increased number of microneedles per unit area of an array (i.e., higher packing density). This results in microneedle arrays that penetrate the skin more easily and reliably than other arrays and/or allow for the receiving or the delivery of greater volumes (and/or higher flow rates) of fluid. In some cases, needles of greater length may be more easily bent or damaged during insertion. Needles that require smaller insertion forces (due to increased sharpness or other factors) allow needles to be formed at longer lengths with less risk of deformation during insertion.

Figure 13:
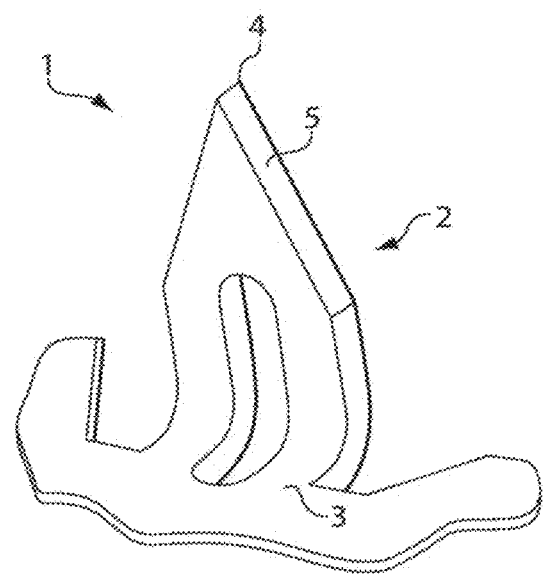
FIG. 13 is a perspective view of a microneedle that is useable in some microneedle array arrangements in accordance with an aspect of the invention.

One aspect of the invention relates to a microneedle arrangement in which the microneedle, and/or an array of microneedles, has improved penetration, fluid transfer or other performance characteristics. In one embodiment, a microneedle may have a point at its distal end that is formed at the intersection of at least four surfaces. Such an arrangement may provide for improved insertion characteristics, e.g., allow the microneedle to more easily penetrate skin and/or maintain a straight trajectory when being inserted into skin or other material. This is in contrast to prior needle tip arrangements in which the needle has a leading contact surface in the form of a line as opposed to a point. For example, FIG. 13 shows a prior microneedle arrangement as taught in U.S. Patent Publication 20070161964 in which the microneedle 1 has a penetrating portion 2 that extends upwardly at an angle relative to a base portion 3 and has a sword-like shape with a tip 4 at a distal end of the penetrating portion 2. In this arrangement, however, the penetrating portion 2 has flat surfaces 5 at its periphery configured such that the tip 4 has a line shape at its extreme distal end. That is, the leading contact surface of the penetrating portion 2 is a line formed by the intersection of two surfaces 5. In some cases, a line-type leading contact surface may not be ideal, e.g., may require relatively higher forces to be placed on the microneedle 1 for insertion than desired.

Figure 14:
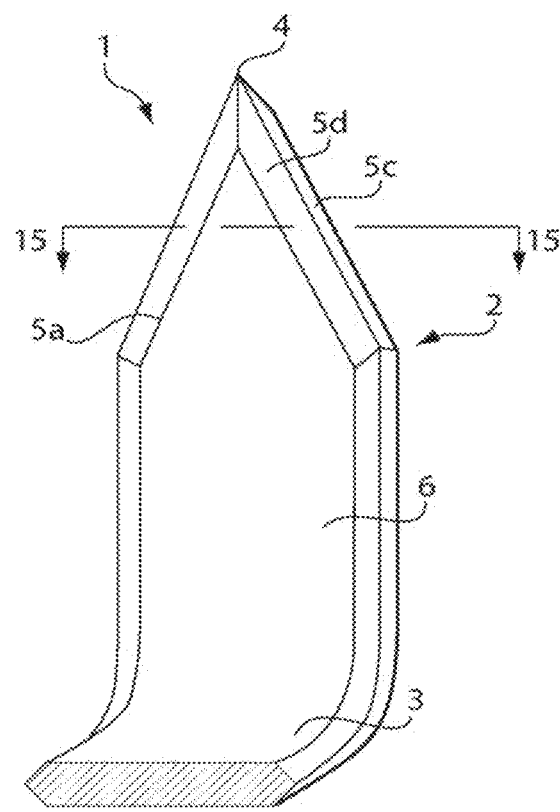
FIG. 14 shows a perspective view of a microneedle having a knife edge in an illustrative embodiment.
Figure 15:
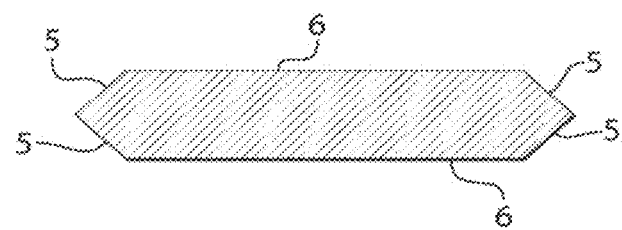
FIG. 15 is a cross sectional view of the microneedle of FIG. 14 along the line 15-15.
Figure 16:
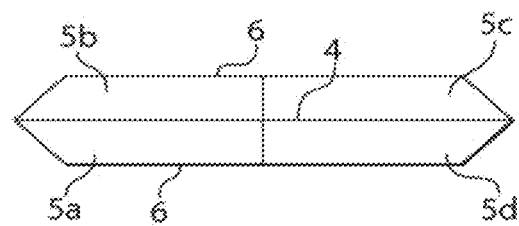
FIG. 16 is a top view of the microneedle in FIG. 14.
Figure 25:
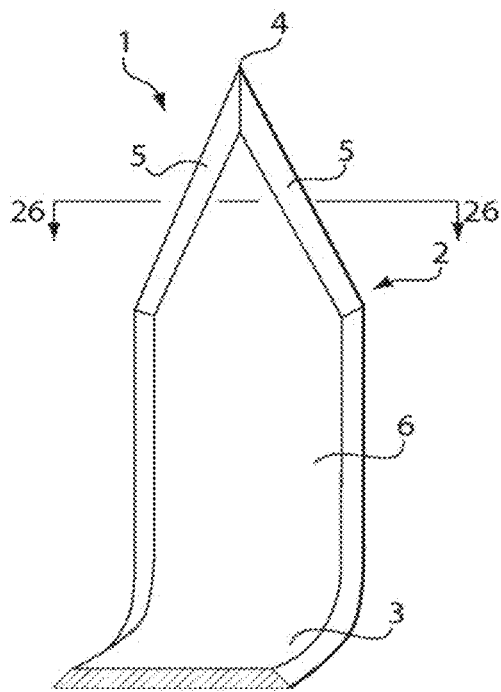
FIG. 25 shows a perspective view of a microneedle having a beveled edge in an illustrative embodiment.
Figure 26:
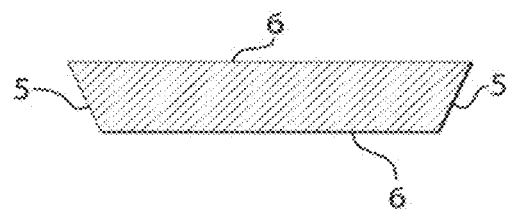
FIG. 26 is a cross sectional view of the microneedle of FIG. 25 along the line 26-26.

In contrast, FIG. 14 shows one embodiment of a microneedle having a tip with a leading contact surface in the form of a point as opposed to a line like that in the FIG. 13 embodiment. That is, in this embodiment, the periphery of the microneedle 1 is formed having a symmetrical V-type knife edge that extends from the base 3 along the length of the penetrating portion 2 to the tip 4. (As used herein, "periphery" refers to at least a portion of an outer edge of the microneedle, and does not necessarily include the entire outer edge of the microneedle.) Accordingly, the penetrating portion 2 has an approximately hexagon-shaped cross-section as shown in FIG. 15 (which is a lateral cross section along a line 15-15 shown in FIG. 14). As can also be seen in FIG. 15, the opposed substantially planar sides 6 of the penetrating portion 2 are interconnected by the knife edge surfaces 5, which are arranged at non-perpendicular angles to the sides 6, and are arranged at an acute angle relative to each other. Thus, when viewed from the top as shown in FIG. 16, the tip 4 has a point at its extreme distal end that is formed at the intersection of four surfaces 5a, 5b, 5c and 5d. Having the tip 4 arranged to have a point may provide benefits, such as reduced force or friction when inserting the penetrating portion 2 into skin or other material. Alternately, or in addition, the surfaces 5a-5d may help maintain a straight trajectory of the tip 4 and penetrating portion 2 when inserted into skin or other material. That is, contact of the surfaces 5a-5d with skin during penetration may exert balanced forces on the penetrating portion 2 that helps to keep the tip 4 traveling along a straight path. This is in contrast to an arrangement like that in FIG. 13 where the tip 4 has no surfaces to provide balanced forces on the tip in directions generally perpendicular to the width of the penetrating portion 2, i.e., in directions parallel to the planes of the side surfaces 5 of the penetrating portion 2 at the tip 4. The pointed tip 4 of the FIG. 14 embodiment is also in contrast to a microneedle arrangement like that shown in FIGS. 25 and 26, in which the microneedle has a single beveled surface 5 at its periphery. Since the microneedle in FIG. 25 has single beveled surfaces 5 at the tip 4, the tip 4 will generally not experience balanced forces when inserted into skin or other material. This is because the beveled surfaces 5 at the tip 4 will exert a force on the tip 4 that tends to bend the penetrating portion away from the base 3, tending to flatten the needle. Such forces can cause the microneedle 1 to bend or break in some environments, rendering the microneedle 1 less useful for its intended function. For example, one of the possible consequences of bending is incomplete insertion. Bending during insertion causes the needles to deflect away from each other and results in a non-parallel arrangement between the needles. This may, in turn, limit the insertion depth.

Figure 17:
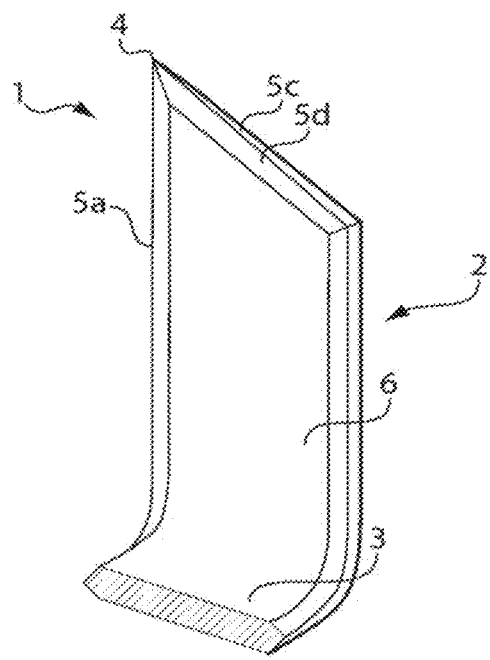
FIG. 17 shows a perspective view of a microneedle having a knife edge in another illustrative embodiment.

It should be understood that embodiments in accordance with the invention may be configured in ways other than that shown in FIGS. 14-16. For example, FIG. 17 shows a microneedle 1 arrangement having a chisel-like shape as opposed to the sword-like shape in FIG. 14. However, as in the FIG. 14 embodiment, a periphery of the penetrating portion 2 has a V-type knife edge formed by surfaces 5 that are arranged at an acute angle relative to each other and that interconnect, or join, the relatively broad, opposed planar sides 6 of the penetrating portion 2. Also like the FIG. 14 embodiment, the tip 4 in FIG. 17 has a point that is formed at the intersection of four surfaces, i.e., the knife edge surfaces 5. However, it should be noted that while the microneedle in FIG. 17 may experience balanced forces on the tip 4 in directions generally perpendicular to the sides 6, the longer, angled surfaces 5 on the right side of the microneedle 1 may exert forces on the penetrating portion 2 that cause the microneedle 1 to bend toward the left (as shown in FIG. 17) when being inserted into skin or other material. Other arrangements are possible in accordance with aspects of the invention, such as forming a knife edge on a periphery of the penetrating portion in an asymmetrical way (e.g., so that the surfaces 5 have a different width and/or are arranged at a different angle with respect to the planar sides 6 of the penetrating portion), forming the knife edge so as to include more than two surfaces that interconnect the planar sides 6 (e.g., each surface 5 may be arranged to be formed by two or more surfaces), the penetrating portion 2 may be arranged to include two or more points (e.g., the sword shaped penetrating portion 2 of FIG. 14 may be split so that a slot extends from the tip 4 down toward the base 3, thus providing the penetrating portion 2 with two points), the penetrating portion 2 may include one or more channels, holes, grooves or other features (e.g., such as the opening in the needle of FIG. 13 to facilitate fluid flow), and others.

Another aspect of the invention relates to a method for forming a microneedle, e.g., so as to include a knife edge or other multiple surface arrangement at a periphery of the microneedle. One embodiment shown schematically in FIGS. 18 and 19 involves providing a layer of material from which one or more microneedles is to be formed. The layer may include any suitable material or combination of materials, such as metals, polymers, ceramics, and other materials. In this illustrative embodiment, the layer 7 is a single layer of titanium (e.g., a roll formed sheet, a sputter or vapor deposited layer, or otherwise formed), having top and bottom (opposed) substantially planar sides. (It should be understood that the term "planar" as used herein refers to a generally flat surface or region that may, in some cases, include bumps, holes or other relatively small surface irregularities. For example, chemical etching can in some environments form pits, grooves or other surface features on a sheet of material. Thus, a planar side or surface need not be completely flat and/or smooth.) In this embodiment, a pattern 8 is formed on both the top and bottom surfaces of the layer 7 that corresponds to at least a portion of the desired shape for the microneedle 1 (FIG. 14). In this case, the patterns 8 have a sword-like shape so as to form a sword shaped microneedle 1, although other shapes or configurations are possible. The pattern 8 may be formed in any suitable way, such as by a photolithographic process including depositing a layer of photoresist on the layer 7, exposing the photoresist to a suitable illumination pattern, and etching the resist to form the pattern 8 shown in FIG. 18. After providing the patterns 8, the layer 7 may be etched (e.g., by chemical etching) from one or both sides (whether simultaneously or consecutively) to form the microneedle 1 having edge surfaces 5 that form a knife edge at the periphery of the microneedle 1. As is understood in the art, if the layer 7 is an isotropic material (or otherwise suitably formed) and the etching process is likewise isotropic (i.e., equal in etch rate in all directions), beveled surfaces 5 will be formed as shown in FIG. 19. This arrangement can provide a convenient way to form a knife edge around the microneedle 1 with a suitably sharp edge and other characteristics. Moreover, the use of photolithographic processes to form the microneedles allows for a flexibility in the shape, size and other features of the needles.

Figure 18:
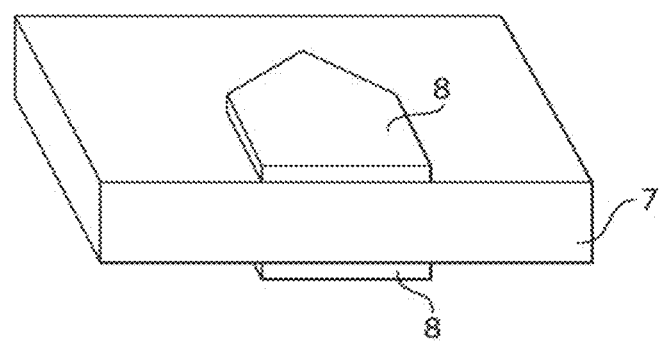

Although the pattern and etching method shown schematically in FIGS. 18 and 19 can be used to form a microneedle in accordance with aspects of the invention, a microneedle can be formed using other techniques. For example, a knife edge can be formed on a microneedle using other techniques that do not involve a pattern and/or chemical etching, such as grinding, molding, stamping, laser etching, and others. Accordingly, aspects of the invention regarding microneedles having certain physical features are not necessarily limited in any way with respect to how those features are formed.

Another aspect of the invention relates to an arrangement for an array of microneedles. In one embodiment, a plurality of microneedles may be configured so that the base of each microneedle is arranged at a periphery of a closed loop that lies in a plane. The penetrating portion of each microneedle may extend at an angle away from the base and the plane of the closed loop, e.g., to form an array of needles in a ring-like shape. For example, FIG. 20 shows a microneedle array including a plurality of microneedles 1 arranged in a circular array such that the base 3 of each needle 1 is arranged in a periphery of a closed loop (in this case a circle). The penetrating portions 2 of the needles 1 all extend at an angle (e.g., a 90 degree angle) away from the plane of the closed loop. Although in this embodiment, the microneedles 1 have a knife edge and other features like that shown in FIG. 14, the microneedles 1 may be arranged in any suitable way. For example, FIG. 21 shows a similar array of microneedles 1 in which the needles have a distal end and tip arranged like that in FIG. 13. In other embodiments, the microneedles may have an arrangement like that shown in FIG. 25. Thus, an array of microneedles in accordance with this aspect of the invention is not limited with respect to how the tip or other features of the microneedle 1 are configured. The closed loop may be of any suitable shape, including, but not limited to, circular, elliptical, hexagonal, rectangular, pentagonal, octagonal or other curved or irregular shape. Also, the term "closed loop" does not require that the bases 3 of the microneedles 1 in an array be connected together in a continuous fashion like that shown in FIGS. 20 and 21. Rather, "closed loop" is used to refer to a shape that is formed by drawing a line that connects the bases of the microneedles in an array to each other. Thus, for example, the array in FIG. 20 may be arranged so that the bases 3 of the microneedles 1 are not connected together by an annular ring as shown, but may instead be physically separate from each other. In other embodiments, however, the array may be arranged so that the bases 3 of the microneedles 1 are connected together.

Figure 22:
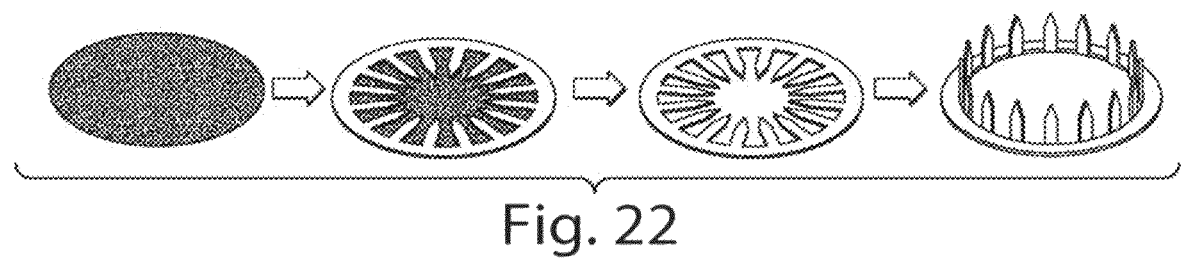
FIG. 22 schematically shows steps in a method for forming the array of FIG. 20.

FIG. 22 shows schematic steps in an illustrative method for forming an array of microneedles arranged like that in FIGS. 20 and 21. In an initial step, a layer of material is provided, e.g., a layer of titanium or other suitable material or combination of materials. Next, a pattern is provided on one or both sides of the layer. In this embodiment, the pattern corresponds to a desired shape of the microneedles. The pattern may be formed in any suitable way, such as using a photolithographic process, a stamping process, or other. Next, the layer is etched, e.g., using a chemical etch or other suitable process, to form the layer into a desired arrangement. Etching may be performed from one or both sides of the layer. In this embodiment, a plurality of microneedles are formed from the layer with each microneedle having its base arranged in a periphery of a closed loop (in this case a circle) and with the penetrating portions 2 of the needles 1 extending toward a center of the closed loop. As can be seen in the third step from the left in FIG. 22, the microneedles 1 each "point" toward at least one other microneedle in the array, and the microneedles are generally not parallel with each other (although some microneedles may be parallel to one or more microneedles). Although in this embodiment the penetrating portions 2 extend toward an exact center of the closed loop, the penetrating portions may generally extend toward a center of the closed loop. For example, if the closed loop is in the form of an ellipse, the penetrating portions may generally extend inwardly without having all of the penetrating portions extending toward a precise, geometric center of the ellipse. In other embodiments, the penetrating portions 2 may generally extend away from the center of the closed loop. Lastly, the penetrating portions 2 of the microneedles 1 may be bent upwardly from the plane of the base and closed loop so that the penetrating portions 2 extend at an angle from the plane. In this embodiment, the penetrating portions 2 are arranged at a 90 degree angle to the plane, but other angles may be used. For example, the penetrating portions 2 may be bent upwardly at a 45 degree angle at a point near the base 3, and then bent upwardly again another 45 degrees at an upper region so that the tip 4 extends generally perpendicularly to the plane of the closed loop and the bases 3. This arrangement may allow the tips 4 of the penetrating portions 2 to be more compliant, allowing the penetrating portions 2 to bend elastically rather than plastically when confronted with a material that is difficult to penetrate. In another embodiment, a 90 degree bend may be made at a position along the length of the needle away from the plane of the base.

Figure 23:
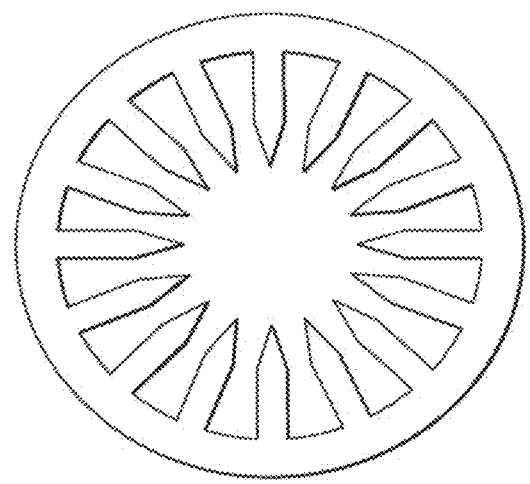
FIG. 23 shows a plan view of the array of FIG. 21 prior to a bending step
Figure 24:
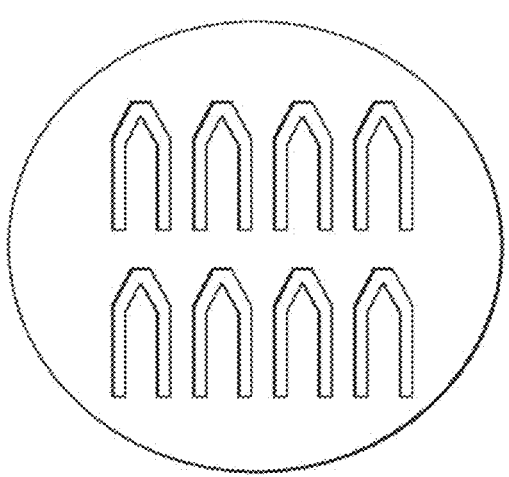
FIG. 24 shows a plan view of a rectangular microneedle array prior to a bending step.

Arranging microneedles such that the bases of the needles are located at a periphery of a closed loop allows for an increased packing density (e.g., number of needles per unit area) than prior arrangements. In some embodiments, the packing density may be 2 microneedles per square millimeter or more, e.g., where the microneedle length is greater than 500 microns. For example, FIG. 23 shows a plan view of a microneedle array formed like that in FIG. 22 prior to bending the penetrating portions 2 upwardly away from the bases 3 and the common plane of the layer in which the microneedles are initially formed. This arrangement includes a total of 16 microneedles. In one embodiment, the microneedles may each be about 750 μm long and the array may have a diameter of about 3 mm. In contrast, FIG. 24 shows a rectangular array of 8 microneedles each having the same size and shape as in the FIG. 23 embodiment, i.e., the needles are 750 μm long and are parallel to each other, and the array has a diameter of about 3 mm. Since the FIG. 23 array has twice the number of needles, the FIG. 23 array will have a larger capacity for fluid flow (whether total fluid volume and/or flow rate) as compared to the FIG. 24 array while having the same overall size. Moreover, the central void in the FIG. 23 array (i.e., the central area containing no needles) may provide additional benefits, such as channeling flow toward a center of the array for easier collection. In some cases, a small distance between microneedles may decrease ease of insertion. In some cases, it may be desirable to maintain a minimum spacing between microneedles. For example, the minimum spacing may be about 100 micrometers, about 200 micrometers, about 300 micrometers, about 400 micrometers, about 500 micrometers, about 600 micrometers, about 700 micrometers, about 800 micrometers or about 900 micrometers. This minimum spacing limits the number of needles that can be arranged in a confined area, for example, a base with a small area. In some cases, a circular configuration may maximize the number of needles that can fit in the confined area.

Figure 27:
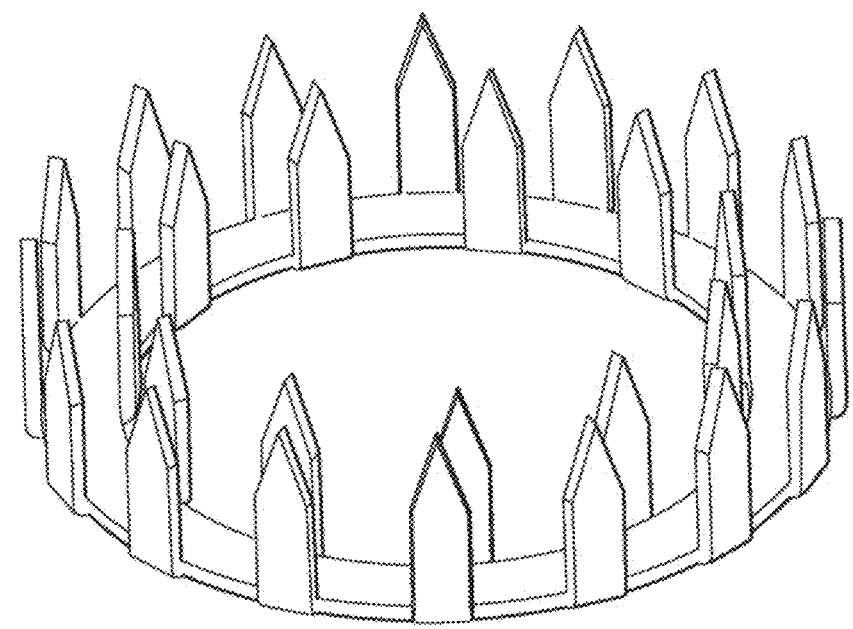
FIG. 27 shows an illustrative array of microneedles having two groups of microneedles arranged with respect to concentric closed loops.

Aspects of the invention are not limited to microneedle arrays in which only a single group of microneedles are arranged with their bases at the periphery of a closed loop. For example, an array may include two or more groups of needles that are arranged with respect to different closed loops. Arrays may include a plurality of groups of needles. FIG. 27 shows an illustrative embodiment that includes a first group of microneedles 1 arranged in an inner pattern (in this case a circular arrangement) and a second group of microneedles 1 arranged in an outer pattern (also a circular pattern in this embodiment. Other arrangements will occur to those of skill in the art. For example, the closed loops for concentric patterns like that in FIG. 27 may have different sizes or shapes, such as a first inner group of needles arranged with respect to a closed loop in a pentagonal shape and a second outer group of needles arranged with respect to a closed loop in a hexagonal shape. Moreover, the centers of the closed loops need not be coincident, but instead may be offset from each other.

In yet other embodiments, an array may include three or more closed loops of microneedles, such as a larger closed loop of microneedles that surrounds two smaller closed loops of microneedles. The closed loops need not be "concentric" in the sense that a smallest closed loop is contained within a medium sized closed loop, which is in turn contained within a larger closed loop and so on. Instead, for example, two smaller closed loops may be adjacent each other and contained within a larger closed loop. In some illustrative embodiments, however, the closed loops are concentric circles. In some embodiments, a needle arrangement may include a plurality of these pairs of closed loops.

The invention, in one set of embodiments, involves the determination of a condition of a subject. Bodily fluids and/or other material associated with the skin may be analyzed, for instance, as an indication of a past, present and/or future condition of the subject, or to determine conditions that are external to the subject. Determination may occur, for instance, visually, tactilely, by odor, via instrumentation, etc. In one aspect, accordingly, the present invention is generally directed to various devices for delivering and/or receiving blood, or other bodily fluids, from the skin and/or from beneath the skin of a subject. Accordingly, in the description that follows, the discussion of blood is by way of example only, and in other embodiments, other fluids may be received from the skin in addition to and/or instead of blood.

In one set of embodiments, the device includes a substance transfer component able to deliver to or receive fluid from the subject. As used herein, "substance transfer component" is any component or combination of components that facilitates movement of a substance or a fluid from one portion of the device to another, and/or from the device to the subject or vice versa. The substance transfer component may include an opening of any size and/or geometry that is constructed to receive fluid into the device. For example, an opening of a substance transfer component may lie in a two-dimensional plane or the opening may include a three-dimensional cavity, hole, groove, slit, etc. In some embodiments, the substance transfer component may also include one or more microneedles or other skin insertion objects, arranged to cause fluid to be released from the subject, e.g., by piercing the skin of a subject. In some embodiments, if fluid may partially or fully fill an enclosure surrounding a skin insertion object or other object, then the enclosure can define at least part of a substance transfer component. A substance transfer component may include any other suitable fluid transporter or flow activator. Other components including partially or fully enclosed channels, microfluidic channels, tubes, wicking members, vacuum containers, etc. can be, or be a part of, a substance transfer component.

If needles or microneedles are used, they may be solid or hollow, i.e., blood or other fluid may travel in and/or around the needles or microneedles into or from the device. In some cases, the needles or microneedles may also be removed from the subject, e.g., after insertion into the skin, for example, to increase the flow of blood or other fluids from the subject. In one set of embodiments, the substance transfer component includes solid needles that are removed from the skin and a cup or channel to direct the flow of blood or other bodily fluids.

It should be noted that a skin insertion object or other flow activator need not be included with all embodiments as the device may not necessarily employ a mechanism for causing fluid release from the subject. For instance, the device may receive fluid that has already been released due to another cause, such as a cut or an abrasion, fluid release due to a separate and independent device, such as a separate lancet, an open fluid access such as during a surgical operation, and so on. Additionally, fluid may be introduced into the device via urination, spitting, pouring fluid into the device, etc. If included, a skin insertion object or other substance transfer component may physically penetrate, pierce, and/or or abrade, chemically peel, corrode and/or irritate, release and/or produce electromagnetic, acoustic or other waves, other otherwise operate to cause fluid release from a subject. The substance transfer component may include a moveable mechanism, e.g., to move a needle, or may not require movement to function. For example, the substance transfer component may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of an element to cause fluid release from a subject.

In some aspects, the device may include a support structure, such as a housing. The housing may be used, as discussed herein, for applying the substance transfer component to the surface of the skin of the subject, e.g., so that fluid may be delivered and/or received from the skin of the subject. In some cases, the housing may immobilize the substance transfer component such that the substance transfer component cannot move relative to the housing; in other cases, however, the substance transfer component, or a portion thereof, may be able to move relative to the housing. In one embodiment, as a non-limiting example, the substance transfer component is immobilized relative to the housing, and the deployment actuator is positioned within the device such that application of the device to the skin causes at least a portion of the substance transfer component to pierce the skin of the subject. In some cases, as previously discussed, the housing encloses a deployment actuator.

In some embodiments, the deployment actuator, or a portion of the deployment actuator, may move from a first position to a second position. For example, the first position may be one where the deployment actuator has attached thereto a substance transfer component that is not in contact with the skin (e.g., a skin insertion object of the substance transfer component may be contained within a recess of the substance transfer component), while the second position of the deployment actuator may be one where the substance transfer component does contact the skin, e.g., to pierce the skin. The deployment actuator may be moved using any suitable technique, e.g., manually, mechanically, electromagnetically, using a servo mechanism, or the like. In one set of embodiments, for example, the deployment actuator may be moved from a first position to a second position by pushing a button on the device, which causes the deployment actuator to move (either directly, or through a mechanism linking the button with the deployment actuator). Other mechanisms (e.g., dials, levers, sliders, etc., as discussed herein) may be used in conjunction of or instead of a button. In another set of embodiments, the deployment actuator may be moved from a first position to a second position automatically, for example, upon activation by a computer, upon remote activation, after a period of time has elapsed, or the like. For example, in one embodiment, a servo connected to the deployment actuator is activated electronically, moving the deployment actuator from the first position to the second position. In some cases, the deployment actuator may include a triggering mechanism that initiates deployment.

In some cases, the deployment actuator and/or the substance transfer component may also be moved from the second position to the first position (or some other position). For example, after fluid has been delivered and/or received from the skin, e.g., using a substance transfer component, the deployment actuator may be moved, which may move the substance transfer component away from contact with the skin. The deployment actuator may be moved from the second position to the first position using any suitable technique, including those described above, and the technique for moving the deployment actuator from the second position to the first position may be the same or different as that moving the deployment actuator from the first position to the second position.

In some cases, the device may be able to draw skin towards the substance transfer component. For example, in one set of embodiments, the device may include a vacuum interface or region. The interface or region may be connected with a vacuum source (external and/or internal to the device), and when a vacuum is applied, skin may be drawn towards the device, e.g., for contact with a substance transfer component, such as one or more needles or microneedles.

In one set of embodiments, the device includes a deployment actuator able to drive a substance transfer component into the skin, e.g., so that the device can receive a fluid from the skin of a subject, and/or so that the substance transfer component can deliver a substance to a subject, e.g. deliver a substance to the skin and/or to a location beneath the skin of a subject. The deployment actuator may be a structure that can be deformed using unaided force (e.g., by a human pushing the structure), or other forces (e.g., electrically-applied forces, mechanical interactions or the like), but is able to restore its original shape after the force is removed or at least partially reduced. For example, the structure may restore its original shape spontaneously, or some action (e.g., heating) may be needed to restore the structure to its original shape. In one set of embodiments, the deployment actuator may include a flexible concave member or a reversibly deformable structure that is moveable between a first configuration and a second configuration. The deployment actuator may be formed out a suitable elastic material, in some cases. For instance, the structure may be formed from a plastic, a polymer, a metal, etc. In one set of embodiments, the structure may have a concave or convex shape. For instance, the edges of the structure may be put under compressive stress such that the structure "bows" out to form a concave or convex shape. A person pushing against the concave or convex shape may deform the structure, but after the person stops pushing on the structure, the structure may be able to return to its original concave or convex shape, e.g., spontaneously or with the aid of other forces as previously discussed. In some cases, the device may be bistable, i.e., having two different positions in which the device is stable.

Figure 10A:
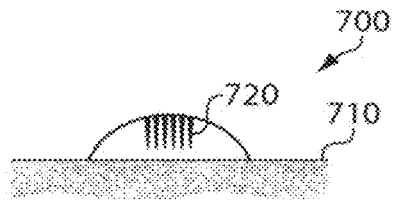
FIGS. 10A-10C illustrate a device in still another embodiment illustrating a deployment actuator.
Figure 10B:
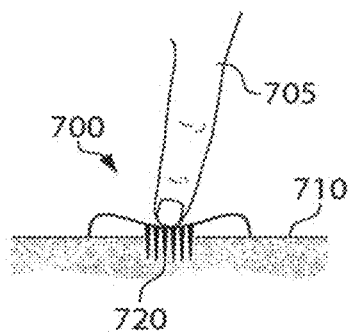
Figure 10C:
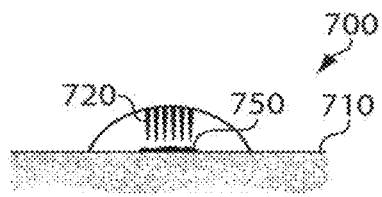

An example of a deployment actuator is now illustrated with respect to FIG. 10. In FIG. 10A, structure 700 has a generally concave shape, and is positioned on the surface of skin 710. Structure 700 also includes a substance transfer component 720 for insertion into the skin. In FIG. 10B, a person (indicated by finger 705) pushes onto structure 700, deforming at least a portion of the structure and thereby forcing a substance transfer component 720 into at least a portion of the skin. In FIG. 10C, after the person releases structure 700, the structure is allowed to return to its original position, e.g., spontaneously, lifting substance transfer component 720 out of the skin. In some cases, e.g., if the substance transfer component includes needles or other skin insertion objects that are sufficiently large or long, blood or other fluids 750 may come out of the skin through the holes created by the needles, and optionally the fluid may be collected by the device for later storage and/or use, as discussed herein.

Figure 11:
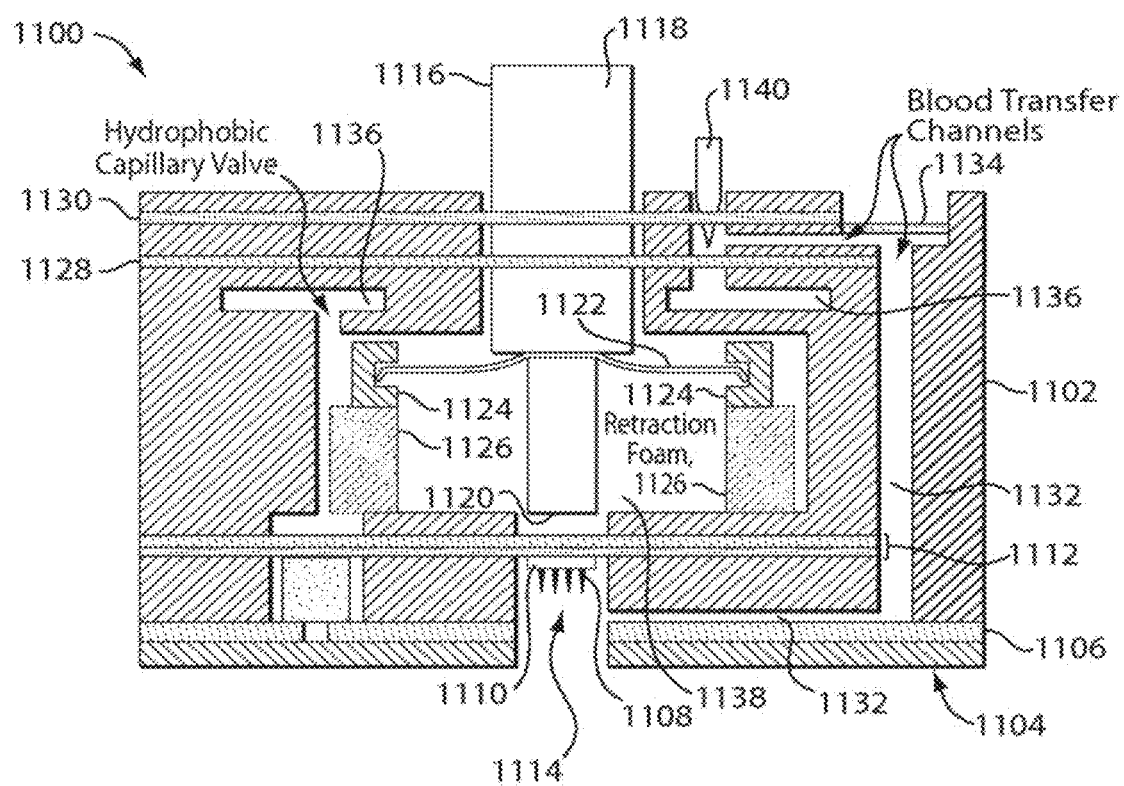
FIG. 11 illustrates yet another embodiment of the invention in which a device is actuated by a deployment actuator.

As another example, referring now to FIG. 11, a device 1100 is illustrated schematically in which a substance transfer component is driven by a deployment actuator. In FIG. 11, device 1100 includes a housing 1102 defining a plurality of chambers and channels. In other embodiments (not shown) a plurality of components that can be separable from and attachable to each other (e.g., modular components) can together define the device and together define a series of channels and compartments necessary for device function. See, e.g., U.S. patent application Ser. No. 12/716,233, filed Mar. 2, 2010, entitled "Systems and Methods for Creating and Using Suction Blisters or Other Pooled Regions of Fluid within the Skin," by Levinson, et al.; U.S. patent application Ser. No. 12/716,226, filed Mar. 2, 2010, entitled "Techniques and Devices Associated with Blood Sampling," by Levinson, et al.; or U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al., each incorporated herein by reference.

In the specific device illustrated, device 1100 includes a surface 1104 for positioning the device proximate the skin of a subject during use. Where desired in certain embodiments, the device can include an adhesive layer 1106 where the adhesive is selected to be suitable for retaining the device in a relatively fixed position relative to the skin during use, but may allow for relatively easy removal of the device from the skin following use. Specific non-limiting examples of adhesives are discussed below. The adhesive also can be selected to assist in maintaining a vacuum within portions of the device proximate the skin as will be understood.

In FIG. 11, device 1100 includes a substance transfer component 1108. The substance transfer component may be or include, for example, a skin insertion object or other suitable object as discussed herein. Specific non-limiting examples include needles or microneedles, e.g., as shown in FIG. 11. The substance transfer component can be or include, as described elsewhere herein and in other documents incorporated herein by reference, any of a variety of components able to receive a substance from the skin and/or from beneath the skin of a subject, and or deliver a substance to the skin and/or to a location beneath the skin of the subject. For example, the substance transfer component may include one or more needles and/or microneedles, a hygroscopic agent, a cutter or other piercing element, an electrically-assisted system, or the like. In the specific device illustrated, substance transfer component 1108 includes an array of skin insertion objects such as solid or hollow microneedles. In one set of embodiments, substance transfer component 1108 is selected to have a particular size and profile for a particular use. For example, the substance transfer component may include an array of skin insertion objects which, in the device illustrated, emanate from a base 1110 which will be described further below.

In certain embodiments, a plurality of skin insertion objects of the substance transfer component 1108 and are relatively small, and are relatively completely driven into the skin. The skin insertion objects may be positioned to address the skin of the subject, each protruding from a base and defining a length from the base, and are able to be inserted into or through the skin to a depth essentially equal to their length but are prevented, by the base, from inserting at a depth greater than their length. In some embodiments, the plurality of skin insertion objects have an average length (measured from the base) of no more than about 1,000 microns or more than about 2,000 microns, although lengths can differ between individual skin insertion objects. In one set of embodiments, the skin insertion objects are of relatively uniform length, together defining an average length and each differing from the average length by no more than about 50%, about 40%, about 30%, about 10%, or about 5%. The average length of the skin insertion objects, in other embodiments, are no more than about 1,500 microns, no more than about 1,000 microns, no more than about 900 microns, no more than about 800 microns, no more than about 750 microns, no more than about 600 microns, no more than about 500 microns, no more than about 400 microns, or no more than about 350 microns. In some embodiments, a deployment actuator as discussed herein is provided that is able to move the skin insertion objects from a fully pre-deployed position to a fully deployed position with a force sufficient to insert the plurality of skin insertion object into or through the skin to an average insertion depth of at least about 50% the average length of the plurality of skin insertion objects. In other embodiments, the deployment actuator is able to insert the plurality of skin insertion objects to an average insertion depth of at least about 55%, at least about 60%, at least about 65%, at least about 70%, at least about 75%, at least about 80%, at least about 85%, at least about 90%, at least about 92%, about 94%, about 96%, or about 98% of the average length of the plurality of skin insertion objects.

In the device illustrated, the skin insertion objects of the substance transfer component 1108 are mounted on a flexible structure 1112 which, as illustrated, is maintained relatively rigidly through various aspects of the device but which mounts substance transfer component 1108 flexibly for up/down movement relative to the skin. Flexible structure 1112 can be a membrane, a single or multi-layer structure selected from various polymers or the like to provide sufficient properties such as any combination of flexibility, elasticity, gas permeability or impermeability, fluid permeability or impermeability, or the like for desired operation. Portions of flexible structure 1112, skin insertion objects t 1108, and other interior walls of the device define a region 1114 which allows for movement of skin insertion objects 1108 relative to the skin for delivery of a substance to and/or receiving of a substance from the skin or beneath the skin, and, where a substance is received from the skin or from beneath the skin, region 1114 can serve as a reservoir for introduction of the substance into the device. Where a vacuum is used to receive a substance from the subject (as in the embodiment illustrated in FIG. 11), region 1114, when positioned against the skin, can expose vacuum to that portion of the skin proximate surface 1104 of the device and abutting the chamber.

Device 1100 also includes a transfer component actuator 1116 which, as illustrated, includes a proximate portion 1118 which can be addressed by a user of the device (who may be the same or different from the subject the device is administered to) and a distal portion 1120 for addressing skin insertion objects 1108 via flexible structure 1112. Proximal portion 1118 and distal portion 1120 are, in the device illustrated, opposite ends of a single component but, as would be understood by those of ordinary skill in the art, the actuator can include a plurality of individual components operably linked in any way necessary to perform actuation as will be described.

As will be understood, FIG. 11 is a cross-section of a device illustrating various components and channels within the device. As will also be understood by those of ordinary skill in the art, different arrangements of devices and channels are contemplated herein so long as the purpose of the device described herein is met. In this figure, device actuator 1116 is directly connected to or otherwise operably linked to a deployment actuator 1122 which, in the device illustrated, is in the form of a "snap dome," the function and use of which will be described below. The snap dome in this figure has an approximately circular profile. The structure may define an interior and a periphery which, if not circular, may include a plurality of tabs, protrusions, or the like sufficient for support of structure 1122 within the device. As illustrated, a plurality of tabs (or the essentially circular perimeter of) the device are supported within holders 1124, and the center, snap dome portion of the device is operably linked to device actuator 1116, such that movement of the central portion of snap dome 1122 and the periphery of the snap dome can be controlled independently of each other. Holders 1124 are directly connected to or otherwise operably linked to a retraction actuator 1126 which, in the device illustrated, can be a ring-shaped structure positioned under and supporting holders 1124. Holders 1124 can be individual holders and/or a ring-like structure surrounding the periphery of snap dome 1122. A series of one, two, or more support members (e.g., 1130) are positioned near the top of device 1100 and serve to define a series of channels for sample flow, vacuum control, or the like as will be described.

Turning now to channels defined within the device, as described above, region 1114, when the device is positioned against skin, can serve to expose a portion of the skin defined by the periphery of the region to a vacuum, to substance transfer component 1108 as it moves toward and/or away from the skin, and/or to transfer a substance from or to the subject. Region 1114 can house a substance for transfer to the subject, in the form of a pharmaceutical composition or the like, optionally loaded on skin insertion objects 1108. Where blood and/or interstitial fluid is drawn from a subject, region 1114 can serve to introduce the substance into the device from the subject.

A channel 1132 connects region 1114 to other portions of the device in this example. Channel 1132 can be used to deliver a substance to region 1114 for transfer to a subject, or for application of a vacuum to region 1114, and/or for receiving of a substance from a subject. The remainder of the description of device 1100 will be made within the context of receiving a substance such as blood and/or interstitial fluid from a subject, but it is to be understood that substances can also be delivered via various channels. Channel 1132 typically emanates in one direction from region 1114 although a plurality of channels can emanate from the region, arranged radially or otherwise relative to the center of the device. In device 1100, channel 1132 first passes laterally from the center of the device and then upwardly where, near the top of the device, it can, optionally, include one wall defining a window 1134 through which a user of the device can observe transfer of a substance, or through which analysis of a substance may occur. It can also itself define a reservoir, in whole or in part, or be connected to an internal or an external reservoir for maintaining, storing, and/or transferring a substance drawn from a subject. As shown here, it can be connected to a substance collection reservoir 1136 which, as illustrated, is a disc-shaped reservoir formed in the device housing and surrounding the center of the device including device actuator 1116 and related components.

Device 1100, illustrated as one example of devices provided by the invention, includes a vacuum chamber for applying a vacuum proximate the skin of a subject for receiving a substance from the skin. As illustrated, vacuum chamber 1138 is positioned in a central portion of the device surrounding device actuator 1116, although it can be provided anywhere in or proximate the device. The vacuum chamber can be evacuated to an appropriate level just prior to use, or the device can be pre-packaged under vacuum as described elsewhere herein. As illustrated, vacuum chamber 1138 is in fluid communication with substance collection reservoir 1136 but, in its initial state and prior to use, a membrane or other component, such as support member 1128, separates channel 1132 connecting it to region 1102. In the device illustrated, a vacuum actuation component 1140 can be actuated to puncture the membrane or other component (e.g., 1128) and thereby connect vacuum chamber 1138 with channel 1132, at an appropriate time during use of the device. In other embodiments, device actuator 1116 and vacuum actuation component 1140 can be combined into a single button or operably linked so that only one operation is needed to actuate both the skin insertion objects and the vacuum.

Deployment actuator (or, as shown, a snap dome) 1122 can be provided in a variety of forms including a monostable or bistable configuration. In the embodiment illustrated, a bistable configuration is illustrated including first and second low energy or stable configurations separated by a relatively high energy or unstable configuration. As shown, the deployment actuator 1122 is shown in a "cocked" or pre-deployed position. The deployment actuator may be formed from any suitable material, for example, a metal such as stainless steel (e.g., 301, 301LN, 304, 304L, 304LN, 304H, 305, 312, 321, 321H, 316, 316L, 316LN, 316Ti, 317L, 409, 410, 430, 440A, 440B, 440C, 440F, 904L), carbon steel, spring steel, spring brass, phosphor bronze, beryllium copper, titanium, titanium alloy steels, chrome vanadium, nickel alloy steels (e.g., Monel 400, Monel K 500, Inconel 600, Inconel 718, Inconel x 750, etc.), a polymer (e.g., polyvinylchloride, polypropylene, polycarbonate, etc.), a composite or a laminate (e.g., comprising fiberglass, carbon fiber, bamboo, Kevlar, etc.), or the like. The deployment actuator may be of any shape and/or size. For example, the deployment actuator may have a generally domed shape (e.g., as in a snap dome), and be circular (no legs), or the deployment actuator may have other shapes, e.g., oblong, triangular (3 legs), square (4 legs), pentagonal (5 legs), hexagonal (6 legs), spiderlegged, starlike, clover-shaped (with any number of lobes, e.g., 2, 3, 4, 5, etc.), or the like. The deployment actuator may have, in some embodiments, a hole, dimple, or button in the middle. The deployment actuator may also have a serrated disc or a wave shape. In some cases, the substance transfer component may be mounted on the deployment actuator. In other cases, however, the substance transfer component is mounted on a separate structure which is driven or actuated upon movement of the deployment actuator.

In one set of embodiments, the deployment actuator is not planar, and has a portion that can be in a first position (a "cocked" or pre-deployed position) or a second position (a "fired" or deployed position), optionally separated by a relatively high energy configuration. In some cases, the pre-deployed position may be at a higher energy level than the deployed position. In some cases, both the first position and the second position are stable (i.e., the structure is bistable), although conversion between the first position and the second position requires the structure to proceed through an unstable configuration.

In some cases, surprisingly, the distance or separation between the first position and the second position is relatively small. Such distances or separations may be achieved using snap domes or other configurations such as those described herein, in contrast to springs or other devices which require longer translational or other movements. For example, the perpendicular distance (i.e., in a direction away from the skin) in the deployment actuator between the top of the structure and the bottom of the structure (excluding the substance transfer component) when the device containing the structure is placed on the skin of a subject may be no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm. In another set of embodiments, the deployment actuator may have a greatest lateral dimension (parallel to the skin) when the device containing the structure is placed on the skin of a subject of no more than about 50 mm, no more than about 40 mm, no more than about 30 mm, no more than about 25 mm, no more than about 20 mm, no more than about 15 mm, no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm.

Use of device 1100 will now be described in the context of receiving a substance such as blood from a subject. Device 1100 is placed against the skin of a subject such that at least a portion of surface 1104 contacts the skin. Prior to use, a cover member (not shown) can cover surface 1104 of the device and can cover region 1114, to protect surface 1104 and region 1114 from contaminants, etc. optionally maintaining the interior of the device in a sterile condition. The cover can be peeled off or otherwise removed from the device, and the device placed against the skin, optionally adhering to the skin. Vacuum actuation component 1140 can be actuated to expose channel 1132 and region 1114 to vacuum at any time, including before, simultaneously, or after actuation of substance transfer component 1108. In one arrangement, vacuum actuation component 1140 is actuated to apply vacuum to region 1114 prior to actuation to substance transfer component 1108, thereby to create a vacuum against the skin proximate region 1114 prior to use. Actuation of device actuator 1116 can take place before or after deployment of vacuum.

When device actuator 1116 is actuated by a user (e.g., when proximal portion 1118 is depressed downwardly as shown in the figure), distal portion 1120 engages skin insertion objects 1108 (optionally via flexible structure 1112) to drive it toward the skin. In some embodiments, foil 1128 is first broken, then retraction actuator 1126 is compressed, then retraction actuator 1126 is broken, before flexible structure 1112 is stretched and the deployment actuator 1122 of the device fires or is actuated. Membranes or other members 1112, 1128, or 1130 may have, in some cases, sufficient flexibility and/or elasticity to allow actuator 1116 to drive skin insertion objects 1108 sufficiently distally (downwardly, as shown) to engage the skin of the subject and carry out the desired function of the device. Various gaskets, bearings, or membranes as shown can be used for this function. Where support member 1128 is a foil or the like used for the purpose of initially separating vacuum reservoir 1138 from channel 1132 (e.g., prior to use), when device actuator 1116 is moved downwardly, vacuum actuation component 1140 may rupture support member 1128 proximate actuator 1116, or flexibly deform as need be, so long as member 1130 (or another component) serves to allow device actuator 1116 to move slidably within the device while maintaining sufficient vacuum in vacuum reservoir 1138 and related channels for use of the device.

When skin insertion objects 1108 engage the skin of the subject and facilitates receiving of a substance from the skin and/or from beneath the skin of the subject, a vacuum can draw the substance into region 1114, through channel or channels 1132, and into substance collection reservoir 1136.

In this process, device actuator 1116 first urges deployment actuator 1122 from its first stable configuration to a relatively unstable configuration and beyond that point, at which point the deployment actuator 1122 rapidly moves to a second stable configuration associated with downward driving of device actuator 1116 to quickly drive access substance transfer component 1108 proximate the skin.

After that point, if it is desirable for access substance transfer component 1108 to be received from the skin, then a variety of techniques can be used to do so. In the device illustrated, retraction actuator 1126 drives holder 1124 upwardly, retracting structure 1122 and device actuator 1116 from substance transfer component 1108. At that point, device actuator 1116 can be operably linked to transfer component 1108 and retract the transfer component, or it can move freely relative to substance transfer component 1108, whereby flexible structure 1112 (e.g., an elastic membrane) or other component can retract substance transfer component 1108 from the skin. The retraction actuator 1126 may include any suitable retraction component. Again, in the device illustrated, retraction actuator 1126 can itself be a reversibly deformable structure such as a leaf spring, coil spring, foam, or the like. During use, when device actuator 1116 is driven downwardly, retraction actuator 1126 is first compressed and, depending upon the size and arrangement of components 1126, 1124, 1122, 1116 and 1108, during compression, substance transfer component 1108 can be driven downwardly to some extent. At the point at which retraction actuator 1126 is compressed and provides a sufficient resistance force, deployment actuator 1122 can be urged from its first configuration through an unstable configuration and can return to its second configuration, driving substance transfer component 1108 against the skin. Then, upon release of user pressure (or other actuation, which can be automatic) from actuator 1116, retraction actuator 1126 can expand and, with structure 1122 optionally remaining in its second, downwardly-driven low-energy configuration, actuator 1116 can be retracted and substance transfer component 1108 retracted from the skin.

Figure 12A:
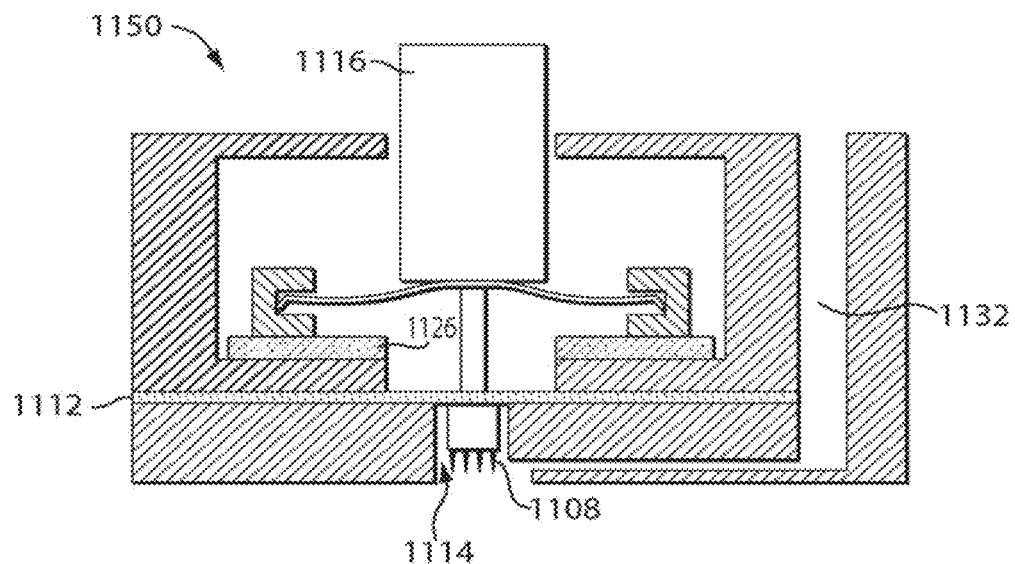
FIGS. 12A and 12B illustrate yet another embodiment of the invention, in which a device is actuated by a deployment actuator, at different stages of operation of the device.
Figure 12B:
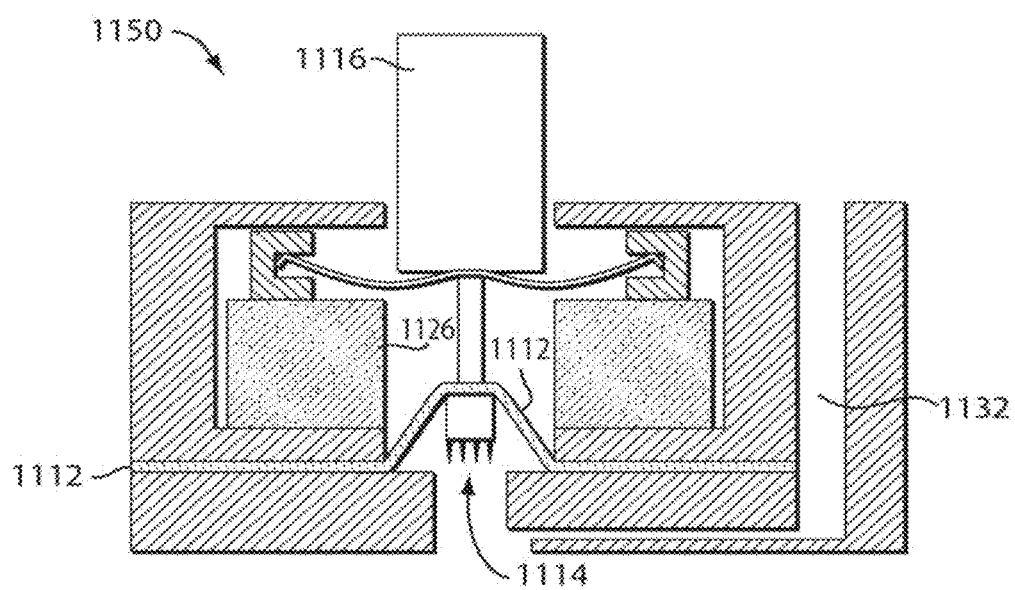

Referring now to FIGS. 12A and 12B, device 1150 is illustrated schematically. Device 1150 is similar to and can be considered essentially identical to device 1100 in all aspects other than those described here with respect to FIGS. 12A and 12B. As such, the reader will observe that not all components are provided, although other components similar to those of device 1100 can exist. One way in which device 1150 differs from device 1100 is that in device 1150, in the pre-deployment or post-deployment retracted configuration, membrane 1112 is drawn proximally (upwardly) as illustrated in FIG. 12B. Membrane 1112 is in a less-stressed lower-energy configuration as shown in FIG. 12A when retraction actuator 1126 is compressed and substance transfer component 1108 is driven proximate the skin. Devices 1100, 1150, and other similar devices are one way to enact a deployment actuator that can move a substance transfer component 1108 relative to the skin in particularly advantageous ways. Examples of deployment actuators include, in addition to the examples shown in FIGS. 11 and 12, blasting caps, explosives, other chemical reactions, solenoids or other electrical interactions, pneumatics (e.g., compressed air), other thermal interactions or mechanical interactions, or the like.

In one set of embodiments, the deployment actuator may move substance transfer component 1108 from a fully pre-deployed position (e.g., as shown in FIG. 11) to a fully deployed position in which substance transfer component 1108 is fully engaged with the skin, in a short period of time.

In one embodiment, that period of time is less than about 0.01 seconds, and in other embodiments, less than about 0.009 seconds, less than about 0.008 seconds, less than about 0.007 seconds, less than about 0.006 seconds, less than about 0.005 seconds, less than about 0.004 seconds, less than about 0.003 seconds, less than about 0.002 seconds, less than about 0.001 seconds, less than about 0.0005 seconds, less than about 0.00025, or less than about 0.0001 seconds.

In some embodiments, the distance between the fully pre-deployed position and the fully deployed position is no more than about 1,000 microns, no more than about 2,500 microns, or no more than about 5,000 microns.

In another embodiment, substance transfer component 1108 moves quickly relative to skin during deployment via the deployment actuator, reaching a speed of at least about 4 m/s, at least about 5 m/s, at least about 6 m/s, at least about 7 m/s, at least about 8 m/s, at least about 10 m/s, at least about 12 m/s, at least about 15 m/s, or at least about 20 m/sat the point at which substance transfer component 1108 first touches the skin during deployment.

In some cases, substance transfer component 1108 achieves relatively high accelerations due to the deployment actuator. For example, in some cases, the deployment actuator can produce average accelerations (e.g., average acceleration from start of movement to a position where a substance transfer component first contacts a subject) of at least about 4 m/s2, about 6 m/s2, about 8 m/s2, about 10 m/s2, about 12 m/s2, about 15 m/s2, or about 20 m/s2, at least about 30 m/s2, at least about 50 m/s2, at least about 100 m/s2, at least about 300 m/s2, at least about 500 m/s2, at least about 1,000 m/s2, at least about 3,000 m/s2, at least about 5,000 m/s2, at least about 10,000 m/s2, at least about 30,000 m/s2, at least about 50,000 m/s2, at least about 60,000 m/s2, at least about 70,000 m/s2, at least about 100,000 m/s2, at least about 200,000 m/s2, or at least about 300,000 m/s2. In some cases, the deployment actuator can produce instantaneous accelerations of at least about 4 m/s2, about 6 m/s2, about 8 m/s2, about 10 m/s2, about 12 m/s2, about 15 m/s2, or about 20 m/s2, at least about 30 m/s2, at least about 50 m/s2, at least about 100 m/s2, at least about 300 m/s2, at least about 500 m/s2, at least about 1,000 m/s2, at least about 3,000 m/s2, at least about 5,000 m/s2, at least about 10,000 m/s2, at least about 30,000 m/s2, at least about 50,000 m/s2, at least about 60,000 m/s2, at least about 70,000 m/s2, at least about 80,000 m/s2, at least about 80,000 m/s2, at least about 100,000 m/s2, at least about 200,000 m/s2, or at least about 300,000 m/s2.

Average acceleration is used to mean the rate of change of velocity over the entire time period from the pre-deployed position to the deployed position, and instantaneous acceleration is used to mean the acceleration at a specific point in time during the time period. The average acceleration and the instantaneous accelerations may be determined using high-speed imaging analysis. High speed imaging is used to capture a sequence of video frames with very short time steps between frames. In one example, the time step between frames may be 66 microseconds, although other time steps are possible depending on imaging equipment capability and/or the total capture time. Each video frame captures the position of a moving object at a specific moment in time. Using this data, position as a function of time may be plotted. An equation that is fit to this data approximates position as a function of time. The second derivative of the position equation is an equation for instantaneous acceleration as a function of time. The acceleration equation can then be used to calculate the instantaneous acceleration at any given point in time.

In some embodiments, the substance transfer component 1108 is accelerated for relatively short periods of time, e.g., less than about 1 second, less than about 300 milliseconds, less than about 100 milliseconds, less than about 30 milliseconds, less than about 10 milliseconds, less than about 3 milliseconds, or less than about 1 millisecond, and/or over relatively short distances, e.g., less than about 5 millimeters, less than about 4 millimeters, less than about 3 millimeters, less than about 2 millimeters, less than about 1 millimeter, less than about 800 micrometers, less than 600 micrometers, less than 500 micrometers, less than 400 micrometers, less than about 300 micrometers, less than about 200 micrometers, less than about 100 micrometers, less than about 50 micrometers, etc. Significant forces can be applied to substance transfer component 1108 as it moves relative to the skin via the deployment actuator. In another set of embodiments, substance transfer component 1108, at the point at which it first contacts the skin, is driven by a force created at least in part by the deployment actuator of at least about 6 micronewtons, about 8 micronewtons, about 10 micronewtons, about 12 micronewtons, or about 15 micronewtons.

Significant forces can be applied to substance transfer component 1108 as it moves relative to the skin via the deployment actuator. In another set of embodiments, substance transfer component 1108, at the point at which it first contacts the skin, is driven by a force created at least in part by the deployment actuator of at least about 6 micronewtons, about 8 micronewtons, about 10 micronewtons, about 12 micronewtons, or about 15 micronewtons.

In another set of embodiments, substance transfer component 1108 applies a pressure to the skin, during deployment caused by the deployment actuator, of at least about 100 N/m2, at least about 300 N/m2, at least about 1,000 N/m2, at least about 3,000 N/m2, etc. In force assessment, the area can be measured as the area of skin displaced by the transfer component at full deployment, e.g., the area of the skin ruptured by the total of the cross sectional area of all substance transfer components inserted into the skin, at the top surface of the skin.

In some cases, the substance transfer component is forced into the skin via the deployment actuator with a force sufficient to insert the substance transfer component into or through the skin to an average depth of at least about 60% of the substance transfer component (or the average length of the substance transfer components, if more than one is used, e.g., as in an array of microneedles). In some cases, the depth is at least about 65%, at least about 70%, at least about 75%, at least about 80%, at least about 85%, at least about 90%, or at least about 95% of the substance transfer component, e.g., the length of the needle or the microneedle inserted into the skin.

Devices of the invention can provide significant advantage in some embodiments. For example, deployment actuators able to move substance transfer components in short time periods, and/or at high velocities, and/or with high forces, and/or with high pressure, and/or drive relatively short substance transfer components such as skin insertion objects or microneedles relatively deeply into the skin and/or through the skin, and/or any combination of the above can provide significant advantage. In some embodiments, these features can provide better control of substance delivery or receipt. Better mechanical stability can be provided in some cases by shorter substance transfer components (e.g., bending and/or buckling can be avoided) and relatively shorter substance transfer components, designed to be driven relatively completely (for example, through nearly all of their entire length) into the skin may offer better control of penetration in some embodiments. If better control of penetration can be achieved, better delivery or receiving can also be achieved in some cases, for example, resulting in less pain or essentially painless deployment.

Moreover, if substance transfer components are used to deliver a substance such as a pharmaceutical composition into or through the skin, more precise delivery can be provided, according to certain embodiments. With better, precise control over depth of insertion of the substance transfer components (e.g., by using devices designed to insert the substance transfer components essentially fully), and/or the substance transfer components contain and/or are coated with a pharmaceutical composition, then more control exists over the amount of pharmaceutical substance inserted into the skin by the substance transfer components, in some embodiments. Furthermore, quick and/or high velocity, and/or high force and/or pressure application of skin insertion objects to the skin may in certain embodiments result in lower pain or painless deployment.

According to one set of embodiments, many devices as discussed herein use various techniques for delivering and/or receiving fluid, for example, in connection with substance transfer components, skin insertion objects, or the like. For example, one or more needles and/or microneedles, a hygroscopic agent, a cutter or other piercing element, an electrically-assisted system, or the like may be used in conjunction with a snap dome or other device as described above. Additional examples of such techniques are described herein and/or in the applications incorporated herein. It is to be understood that, generally, fluids may be delivered and/or received in a variety of ways, and various systems and methods for delivering and/or receiving fluid from the skin are discussed below and/or in the applications incorporated herein. In some embodiments, for example, techniques for piercing or altering the surface of the skin to transport a fluid are discussed, for example, using a needle such as a hypodermic needle or microneedles, chemicals applied to the skin (e.g., penetration enhancers), jet injectors or other techniques such as those discussed below, etc.

As an example, in one embodiment, a needle such as a hypodermic needle can be used to deliver and/or receive fluid to or from the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, the needles may be of any suitable size and length, and may be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc. In one embodiment, the needle is a microneedle. As an example, microneedles such as those disclosed in U.S. Pat. No. 6,334,856, issued Jan. 1, 2002, entitled "Microneedle Devices and Methods of Manufacture and Use Thereof," by Allen, et al., may be used to deliver and/or receive fluids or other materials to or from a subject. The microneedles may be hollow or solid, and may be formed from any suitable material, e.g., metals, ceramics, semiconductors, organics, polymers, and/or composites. Examples include, but are not limited to, pharmaceutical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters.

In some cases, more than one microneedle may be used. For example, arrays of microneedles may be used, and the microneedles may be arranged in the array in any suitable configuration, e.g., periodic, random, etc. In some cases, the array may have 2 or more, 3 or more, 4 or more, 5 or more, 6 or more, 10 or more, 15 or more, 20 or more, 35 or more, 50 or more, 100 or more, or any other suitable number of microneedles. In some embodiments, the device may have at least 3 but no more than 5 needles or microneedles (or other skin insertion objects), at least 6 but no more than 10 needles or microneedles, or at least 11 but no more than 20 needles or microneedles. Typically, a microneedle will have an average cross-sectional dimension (e.g., diameter) of less than about a micron. It should be understood that references to "needle" or "microneedle" as discussed herein are by way of example and ease of presentation only, and that in other embodiments, more than one needle and/or microneedle may be present in any of the descriptions herein.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

In some cases, the microneedles may be present in an array selected such that the density of microneedles within the array is between about 0.5 needles/mm$^2$ and about 10 needles/mm$^2$, and in some cases, the density may be between about 0.6 needles/mm2 and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the subject. The microneedles may be chosen to have smaller or larger areas (or smaller or large diameters), so long as the area of contact for the microneedles to the skin is sufficient to allow adequate blood flow from the subject to the device. The needles or microneedles may have any suitable cross-sectional area. For example, in certain embodiments, each microneedle may be selected to have a cross-sectional area of at least 5 nm$^2$, at least about 100 nm$^2$, at least about 500 nm$^2$, at least about at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, or at least about 25,000 microns$^2$. For example, in certain embodiments, the microneedles may be selected to have a combined skin-penetration area of at least about 500 nm$^2$, at least about 1,000 nm$^2$, at least about 3,000 nm$^2$, at least about 10, nm$^2$nm2, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin, or insertion depth, of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 1500 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum insertion depth of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound or a vasodilator to assist with the flow of blood from the skin of the subject. The coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

At least some the skin insertion objects may be at least partially coated by a substance such as a drug, analgesic or agent by using dip or spray coating or other suitable technique. Thus, the substance may be delivered to the skin by the substance dissolving or otherwise detaching from the substance transfer component at or in the skin or other subject site. Alternately, the substance may be delivered after a substance transfer component penetrates the subject, e.g., in a way similar to a hypodermic needle. For example, a skin insertion object of the substance transfer component may be inserted into the skin, and a substance may be pumped or pushed through a hole, groove or other channel of the skin insertion object (e.g., by a high pressure gas).

A drug may be any composition which possesses therapeutic, prophylactic, or diagnostic properties in vivo, for example when administered to an animal, including mammals, such as humans. The drug can be for local treatment or for regional or systemic therapy. The drug can be or include a peptide, protein, carbohydrate (including monosaccharides, oligosaccharides, and polysaccharides), nucleoprotein, mucoprotein, lipoprotein, glycoprotein, nucleic acid molecules (including any form of DNA such as cDNA, RNA, or a fragment thereof, oligonucleotides, and genes), nucleotide, nucleoside, lipid, biologically active organic or inorganic molecules, or combination thereof. Examples of suitable therapeutic and/or prophylactic active agents include anti-infectives, analgesics, anti-inflammatories, steroids, decongestants, neuroactive agents, anesthetics, and sedatives. Examples of suitable diagnostic agents include radioactive isotopes and radioopaque agents, metals, gases, labels including chromatographic, fluorescent, or enzymatic labels.

Examples of biologically active polypeptides or proteins include, but are not limited to, glucagon, glucagon-like peptides such as, GLP-1, GLP-2 or other GLP analogs, derivatives or agonists of Glucagon Like Peptides, exendins such as, exendin-3 and exendin-4, derivatives, agonists and analogs thereof, vasoactive intestinal peptide (VIP), immunoglobulins, antibodies, cytokines (e.g., lymphokines, monokines, chemokines), interleukins, macrophage activating factors, interferons, erythropoietin, nucleases, tumor necrosis factor, colony stimulating factors (e.g., G-CSF), insulin, enzymes (e.g., superoxide dismutase, plasminogen activator, etc.), tumor suppressors, blood proteins, hormones and hormone analogs and agonists (e.g., follicle stimulating hormone, growth hormone, adrenocorticotropic hormone, and luteinizing hormone releasing hormone (LHRH)), vaccines (e.g., tumoral, bacterial and viral antigens), antigens, blood coagulation factors, growth factors (NGF and EGF), gastrin, GRH, antibacterial peptides such as defensin, enkephalins, bradykinins, calcitonin and muteins, analogs, truncation, deletion and substitution variants and pharmaceutically acceptable salts of all the foregoing. Suitable analgesics include but are not limited to lidocaine, bupivacaine, and tetracaine. Suitable steroids include but are not limited to cortisone, betametasone, budesonide and fluticasone.

In one set of embodiments, the needles or microneedles may be used to deliver a drug into the skin of a subject. The needles or microneedles may be at least partially coated, and the coating may comprise a drug or other therapeutic agent such as those described herein. For example, in one set of embodiments, at least about 50%, at least about 60%, at least about 70%, at least about 80%, at least about 90%, or substantially all of a needle or a microneedle may be coated, and one or more than one needle or microneedle may be coated in a device as discussed herein. For instance, at least about 25%, at least about 50%, at least about 60%, at least about 70%, at least about 80%, at least about 90%, or substantially all of the needles or microneedles in a device may comprise a coating.

Without wishing to be bound by any theory, it is believed that, at least in some cases, longer needles or microneedles may be useful for the delivery of a drug or other therapeutic agent. For example, a needle having a greater depth of penetration into the skin may be useful for delivering the drug or other therapeutic agent deeper into the skin, e.g., closer to capillaries within or below the skin, which may minimize the distance the drug needs to travel before being available systemically and allow a more rapid onset of the drug effect. In addition, greater depth of penetration can be useful for delivering greater amounts of drug. A longer needle can have more surface area exposed internally of the subject, relative to a shorter needle (e.g., of the same diameter), and the increased surface area may allow more of the coating containing drug to be exposed internally of the skin. Thus, for example, a greater amount of drug may be delivered per needle or microneedle that enters the skin.

Accordingly, in certain embodiments, relatively long needles or microneedles may be used for the delivery of a drug or other therapeutic agent into the skin, for example. For instance, the average length of the needles or microneedles in the device may be at least about 200 micrometers, at least about 300 micrometers, at least about 400 micrometers, at least about 500 micrometers, at least about 600 micrometers, at least about 750 micrometers, at least about 800 micrometers, at least about 900 micrometers, at least about 1,000 micrometers, at least about 1,200 micrometers, at least about 1,500 micrometers, at least about 1,700 micrometers, or at least about 2,000 micrometers in some embodiments.

Any of a variety of suitable techniques may be used to coat a needle or a microneedle. For instance, the needle or microneedle may be coated by exposing the needles or microneedles to a liquid containing a substance to be coated thereon. For example, the needles or microneedles may be dipped into a liquid, a liquid may be sprayed on or aerosolized onto the needles or microneedles, an electric field may be used to attract a charged liquid onto the needles or microneedles, etc.

In one embodiment, the fluid is delivered and/or received manually, e.g., by manipulating a plunger on a syringe. In another embodiment, the fluid can be delivered and/or received from the skin mechanically or automatically, e.g., using a piston pump or the like. Fluid may also be received using vacuums such as those discussed herein. For example, vacuum may be applied to a conduit, such as a needle, in fluidic communication with a bodily fluid in order to draw up at least a portion of the fluid from the pooled region. In yet another embodiment, fluid is received using capillary action (e.g., using a microfluidic channel or hypodermic needle having a suitably narrow inner diameter). In still another embodiment, pressure may be applied to force fluid out of the needle.

In some embodiments, a substance is delivered to a subject from a device. In cases where the needle or other skin insertion object is coated with a drug or other substance, the device may deliver the drug or substance to a subject by penetrating the skin with the coated needle. The substance may be delivered to or beneath the skin by the substance dissolving or otherwise detaching from the substance transfer component at the skin or other subject site. The device may or may not cause fluid release from the subject. In some cases, fluid from the subject is not received into the device and a vacuum source is not needed. Also, in some cases, the device may additionally or alternatively deliver a fluid drug or other fluid substance to a subject. The fluid substance may delivered to or beneath the skin through hollow needles that transfer fluid from the device to the subject.

As still another example, pressurized fluids may be used to deliver fluids or other materials into the skin, for instance, using a jet injector or a "hypospray." Typically, such devices produce a high-pressure "jet" of liquid or powder (e.g., a biocompatible liquid, such as saline) that drives material into the skin, and the depth of penetration may be controlled, for instance, by controlling the pressure of the jet. The pressure may come from any suitable source, e.g., a standard gas cylinder or a gas cartridge. A non-limiting example of such a device can be seen in U.S. Pat. No. 4,103,684, issued Aug. 1, 1978, entitled "Hydraulically Powered Hypodermic Injector with Adapters for Reducing and Increasing Fluid Injection Force," by Ismach.

In some embodiments, fluid may be received using a hygroscopic agent applied to the surface of the skin, or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be delivered and/or received from the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the delivery and/or receiving of fluid from the skin. In one embodiment, a cutter is used to create such a pathway and removed, then fluid may be delivered and/or received via this pathway. In another embodiment, the cutter remains in place within the skin, and fluid may be delivered and/or received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a perm-selective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby receiving a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise a substance transfer component in the form of an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a substance transfer component in the form of a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

The device may also contain, in some embodiments, a vacuum source. In some cases, the vacuum source is one that is self-contained within the device, i.e., the device need not be connected to an external vacuum source (e.g., a house vacuum) during use of the device to receive blood from the skin. For example, in one set of embodiments, the vacuum source may include a vacuum chamber having a pressure less than atmospheric pressure before blood (or other fluid) is received into the device, i.e., the vacuum chamber is at a "negative pressure" (that is, negative relative to atmospheric pressure) or a "vacuum pressure" (or just having a "vacuum"). For example, the vacuum in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg, i.e., below atmospheric pressure. However, in other embodiments, it should be understood that other pressures may be used and/or that different methods may be used to produce other pressures (greater than or less than atmospheric pressure). As non-limiting examples, an external vacuum or a mechanical device may be used as the vacuum source; various additional examples are discussed in detail herein.

As a specific, non-limiting example, in one embodiment, a device may be used to receive fluid without an external power and/or a vacuum source. Examples of such devices include skin patches, strips, tapes, bandages, or the like. For instance, a skin patch may be contacted with the skin of a subject, and a vacuum created through a change in shape of a portion of the skin patch or other device (e.g., using a shape memory polymer), which may be used to deliver and/or receive fluid from the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum.

Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

In one set of embodiments, the device may be able to create a pressure differential (e.g. a vacuum). The pressure differential may be created by a pressure regulator. As used here, "pressure regulator" is a pressure controller component or system able to create a pressure differential between two or more locations. The pressure differential should be at least sufficient to urge the movement of fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric pressure in one location, relative to a lower pressure at another location (atmospheric pressure or some other pressure), where the differential between the pressures is sufficient to urge fluid in accordance with the invention. In another example, the regulator or controller will involve a pressure lower than atmospheric pressure (a vacuum) in one location, and a higher pressure at another location(s) (atmospheric pressure or a different pressure) where the differential between the pressures is sufficient to urge fluid in accordance with the invention. Wherever "vacuum" or "pressure" is used herein, in association with a pressure regulator or pressure differential of the invention, it should be understood that the opposite can be implemented as well, as would be understood by those of ordinary skill in the art, i.e., a vacuum chamber can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum chamber, pre-packaged vacuum chamber, or the like. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like. Vacuum chambers can be used in some embodiments, where the device contains, e.g., regions in which a vacuum exits or can be created (e.g. a variable volume chamber, a change in volume of which will affect vacuum or pressure). A vacuum chamber can include pre-evacuated (i.e., pre-packaged) chambers or regions, and/or self-contained actuators. A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for very general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum chamber in the device when used (i.e., the device can be provided ready for use by a subject or practitioner with an evacuated region on or in the device, without the need for any actuation to form the initial vacuum). A pre-packaged pressure or vacuum chamber regulator can, e.g., be a region evacuated (relative to atmospheric pressure) upon manufacture and/or at some point prior to the point at which it is used by a subject or practitioner. For example, a chamber is evacuated upon manufacture, or after manufacture but before delivery of the device to the user, e.g. the clinician or subject. For instance, in some embodiments, the device contains a vacuum chamber having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric pressure. In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum chamber may be in fluidic communication with a needle, which can be used to move the skin towards the device, receive fluid from the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone)diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

Figure 3:
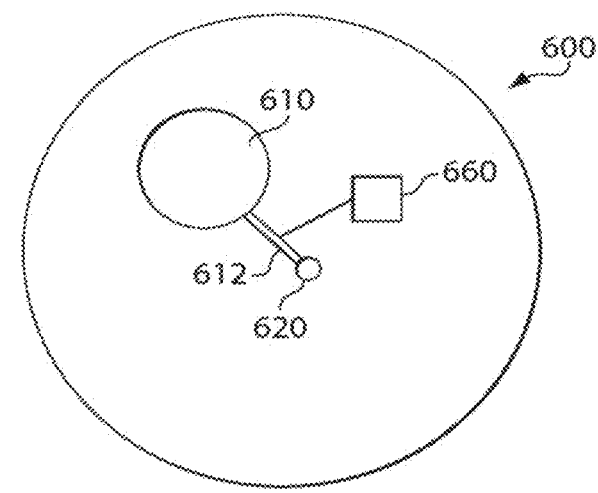
FIG. 3 illustrates a device in one embodiment of the invention, having a vacuum chamber.

In one set of embodiments, the device contains a vacuum chamber that is also used as a storage chamber to receive blood or other fluid received from the subject into the device. For instance, blood received from a subject through or via the substance transfer component may enter the vacuum chamber due to its negative pressure (i.e., because the chamber has an internal pressure less than atmospheric pressure), and optionally stored in the vacuum chamber for later use. A non-limiting example is illustrated in FIG. 3. In this figure, device 600 contains vacuum chamber 610, which is connected to substance transfer component 620 (which may include, e.g., one or more microneedles). Upon activation of vacuum chamber 610 (e.g., using actuator 660, as discussed below), vacuum chamber 610 may be put into fluidic communication with substance transfer component 620. Substance transfer component 620 may accordingly cause negative pressure to be applied to the skin of the subject, for instance, due to the internal pressure within vacuum chamber 610. Fluid (e.g., blood) exiting the skin via substance transfer component 620 may accordingly be drawn into the device and into vacuum chamber 610, e.g., through conduit 612. The fluid collected by the device can then be analyzed within the device or removed from the device for analysis, storage, etc.

In another set of embodiments, however, the device may include separate vacuum chambers and storage chambers (e.g., chambers to store fluid such as blood from the subject). The vacuum chamber and storage chambers may be in fluid communication, and may have any suitable arrangement. In some embodiments, the vacuum from the vacuum chamber may be used, at least in part, to receive fluid from the skin, which is then directed into a storage chamber, e.g., for later analysis or use, for example, as discussed below. As an example, blood may be received into the device, flowing towards a vacuum chamber, but the fluid may be prevented from entering the vacuum chamber. For instance, in certain embodiments, a material permeable to gas but not to a liquid such as blood may be used. For example, the material may be a membrane such as a hydrophilic or hydrophobic membrane having a suitable porosity, a porous structure, a porous ceramic frit, a dissolvable interface (e.g., formed from a salt or a polymer, etc.), or the like.

Figure 4:
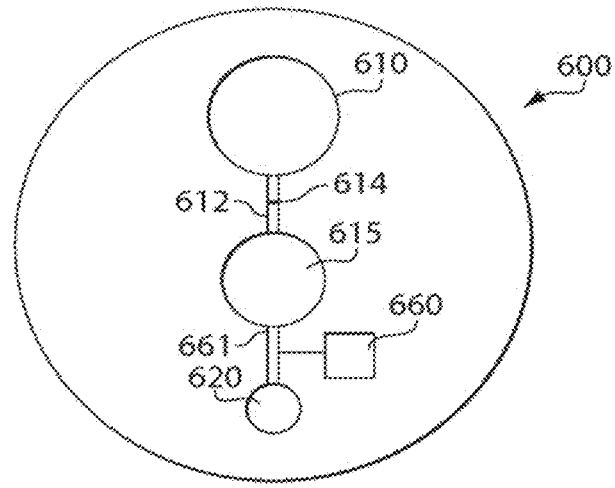
FIG. 4 illustrates a device in another embodiment of the invention, having a vacuum chamber and a storage chamber.

One non-limiting example is illustrated in FIG. 4. In this figure, device 600 contains vacuum chamber 610 and storage chamber 615. Vacuum chamber 610 can be put in fluidic communication with storage chamber 615 via conduit 612, which contains material 614. Material 614 may be any material permeable to gas but not to a liquid in this example, e.g., material 614 may be a membrane such as a hydrophilic membrane or a hydrophobic membrane that has a porosity that allows gas exchange to occur but does not allow the passage of blood from the subject. When device 600 is actuated using actuator 660, blood (or other fluid) flows through substance transfer component 620 via conduit 661 into collection chamber 615 because of the internal vacuum pressure from vacuum chamber 610, which is not completely impeded by material 614 since it is permeable to gases. However, because of material 614, blood (or other suitable bodily fluid) is prevented from entering vacuum chamber 610, and instead remains in storage chamber 615, e.g., for later analysis or use.

In some embodiments, the flow of blood (or other fluid) into the storage chamber may be controlled using a flow controller. The flow controller may be manually and/or automatically controlled to control the flow of blood. The flow controller may activate or deactivate when a certain amount or volume of fluid has entered the storage chamber in certain cases. For instance, the flow controller may stop blood flow after a predetermined amount or volume of blood has entered the storage chamber, and/or the flow controller may be able to control the internal pressure of the storage chamber, e.g., to a specific level, such as a predetermined level. Examples of suitable flow controllers for the device include, but are not limited to, a membrane, a valve, a dissolvable interface, a gate, or the like.

Figure 5:
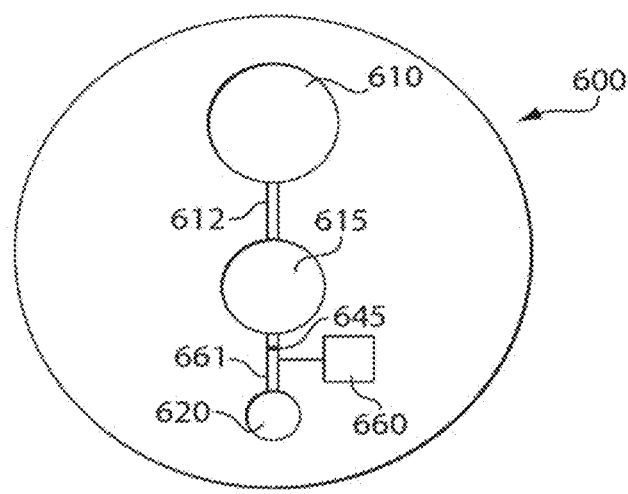
FIG. 5 illustrates a device in yet another embodiment of the invention, having a flow controller.

One non-limiting example of a flow controller is now illustrated with reference to FIG. 5. In this example figure, device 600 includes a vacuum chamber 610 and a storage chamber 615. Fluid entering device 600 via substance transfer component 620 is prevented from entering storage chamber 615 due to flow controller 645 present within conduit 661. However, under suitable conditions, flow controller 645 may be opened, thereby allowing at least some fluid to enter storage chamber 615. In some cases, for instance, storage chamber 615 also contains at least a partial vacuum, although this vacuum may be greater or less than the pressure within chamber 610. In other embodiments, flow controller 645 may initially be open, or be externally controllable (e.g., via an actuator), or the like. In some cases, the flow controller may control the flow of fluid into the device such that, after collection, at least some vacuum is still present in the device.

Thus, in some cases, the device may be constructed and arranged to reproducibly obtain from the subject a controlled amount of fluid, e.g., a controlled amount or volume of blood. The amount of fluid reproducibly obtained from the subject may be controlled, for example, using flow controllers, materials permeable to gas but not to liquids, membranes, valves, pumps, gates, microfluidic systems, or the like, as discussed herein. In particular, it should be noted that the volume of blood or other fluid obtained from the subject need not be strictly a function of the initial vacuum pressure or volume within the device. For example, a flow controller may initially be opened (e.g., manually, automatically, electronically, etc.) to allow fluid to begin entering the device; and when a predetermined condition is reached (e.g., when a certain volume or amount of blood has entered the device), the flow controller may be closed at that point, even if some vacuum pressure remains within the device. In some cases, this control of fluid allows the amount of fluid reproducibly obtained from the subject to be controlled to a great extent. For example, in one set of embodiments, the amount of fluid received from the subject may be controlled to be less than about 1 ml, may be less than about 300 microliters, less than about 100 microliters, less than about 30 microliters, less than about 10 microliters, less than about 3 microliters, less than about 1 microliter, etc.

Figure 6:
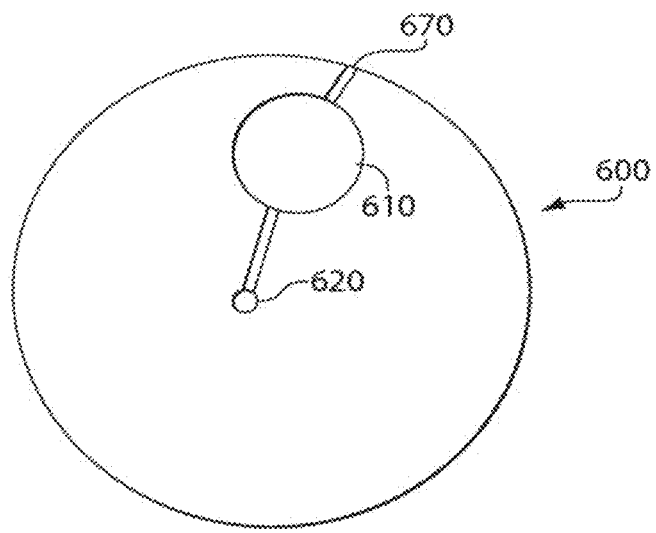
FIG. 6 illustrates a device in yet another embodiment of the invention, having an exit port.
Figure 7:
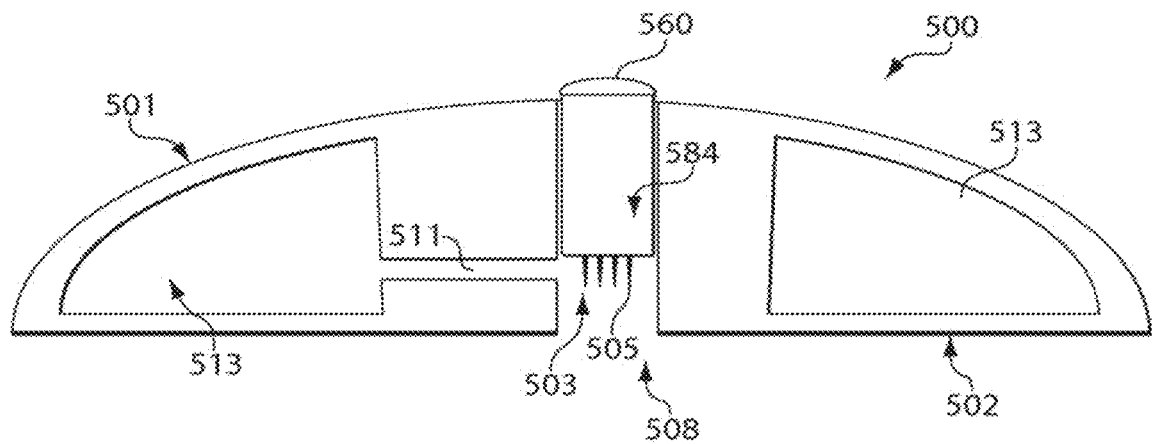
FIG. 7 illustrates a device according to another embodiment of the invention.
Figure 8:
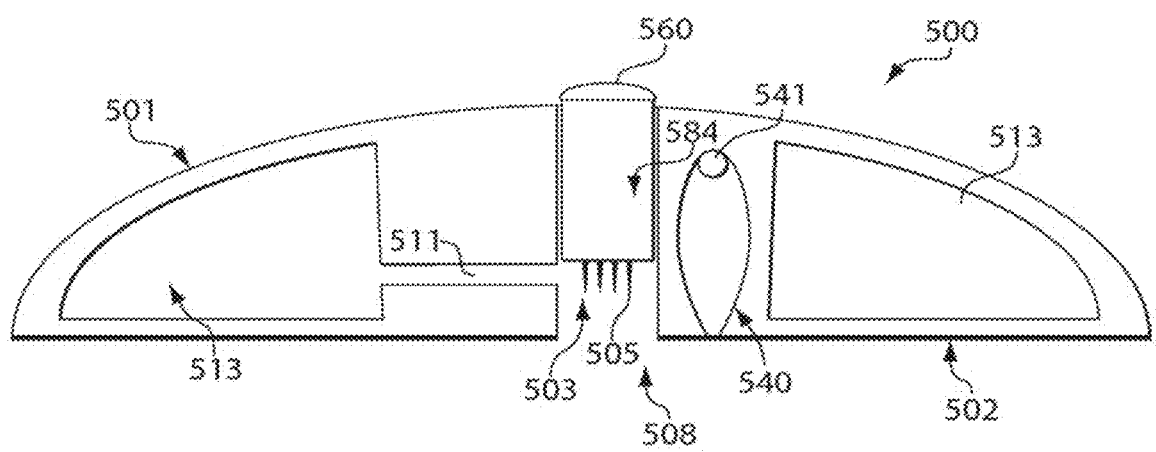
FIG. 8 illustrates a device containing a fluid reservoir, in another embodiment of the invention.

Further examples of various embodiments of the invention are illustrated in FIGS. 6 and 8. In FIG. 7, device 500 is illustrated. In this example, device 500 includes a housing 501, an adhesive 502 for adhesion of the device to the skin, and a substance transfer component 503. In this figure, substance transfer component 503 includes a plurality of microneedles 505, although other substance transfer components as discussed herein may also be used. Microneedles 505 are contained within recess 508. Also shown in FIG. 7 is vacuum chamber 513 which, in this example, is self-contained within device 500. Vacuum chamber 513 is in fluidic communication with recess 508 via channel 511, for example, as controlled by a controller or an actuator. Device actuator 560 is shown at the top of device 500. Device actuator 560 may be, for example, a button, switch, slider, dial, etc. and may cause microneedles 505 to move towards the skin when the device is placed on the skin. For example, the microneedles may be moved mechanically (e.g., compression spring, Belleville spring, etc.), electrically (e.g., with the aid of a servo, which may be computer-controlled), pneumatically, etc. In some cases, device actuator 560 (or another actuator) may be used to cause the microneedles to be received from the skin, and/or the microneedles may be received automatically after delivering and/or receiving fluid from the subject, e.g., without any intervention by the subject, or by another person. Non-limiting examples of such techniques are discussed in detail below.

Another example is illustrated with reference to FIG. 8. In this figure, device 500 includes a housing 501, an adhesive 502 for adhesion of the device to the skin, and a substance transfer component 503. In FIG. 8, substance transfer component 503 includes a plurality of microneedles 505 within recess 508, although other substance transfer components as discussed herein may also be used. Device actuator 560 is shown at the top of device 500. Device actuator 560 may be, for example, a button, switch, slider, dial, etc. and may cause microneedles 505 to move towards the skin when the device is placed on the skin. For example, the microneedles may be moved mechanically (e.g., compression spring, Belleville spring, etc.), electrically (e.g., with the aid of a servo, which may be computer-controlled), pneumatically, etc., e.g., via component 584 (e.g., a piston, a screw, a mechanical linkage, etc.). In some cases, device actuator 560 may also be able to receive the microneedles from the skin after use, e.g., after a fluid is delivered and/or received from the skin.

Chamber 513, in this figure, is a self-contained vacuum chamber. Vacuum chamber 513 is in fluidic communication with recess 508 via channel 511, for example, as controlled by a controller or an actuator. Also illustrated in FIG. 8 is fluid reservoir 540, which may contain a fluid such as an anticoagulant. The fluid may be introduced into blood or other fluid received from the skin. Controlling fluid flow from fluid reservoir may be one or more suitable fluidic control elements, e.g., pumps, nozzles, valves, or the like, for example, pump 541 in FIG. 8.

In certain embodiments, the substance transfer component may be fastened on a deployment actuator. In some cases, the deployment actuator can bring the substance transfer component to the skin, and in certain instances, insert the substance transfer component into the skin. For example, the substance transfer component can be moved mechanically, electrically (e.g., with the aid of a servo, which may be computer-controlled), pneumatically, via a piston, a screw, a mechanical linkage, or the like. In one set of embodiments, the deployment actuator can insert the substance transfer component into the skin at a speed of at least about 0.1 cm/s, at least about 0.3 cm/s, about 1 cm/s, at least about 3 cm/s, at least about 10 cm/s, at least about 30 cm/s, at least about 1 m/s, at least about 2 m/s, at least about 3 m/s, at least about 4 m/s, at least about 5 m/s, at least about 6 m/s, at least about 7 m/s, at least about 8 m/s, at least about 9 m/s, at least about 10 m/s, at least about 12 m/s, etc., at the point where the substance transfer component initially contacts the skin. Without wishing to be bound by any theory, it is believed that relatively faster insertion speeds may increase the ability of the substance transfer component to penetrate the skin (without deforming the skin or causing the skin to move in response), and/or decrease the amount of pain felt by the application of the substance transfer component to the skin. Any suitable method of controlling the penetration speed into the skin may be used, include those described herein.

As mentioned, in some embodiments, blood or other bodily fluids may be stored within the device for later use and/or analysis. For example, the device may be attached to a suitable external apparatus able to analyze a portion of the device (e.g., containing the fluid), and/or the external apparatus may remove at least some of the blood or other fluid from the device for subsequent analysis and/or storage. In some cases, however, at least some analysis may be performed by the device itself, e.g., using one or more sensors, etc., contained within the device.

For example, as discussed in detail below, in some cases, a storage chamber may contain a reagent or a reaction entity able to react with an analyte suspected of being present in the blood (or other fluid) entering the device, and in some cases, the reaction entity may be determined to determine the analyte. In some cases, the determination may be made externally of the device, e.g., by determining a color change or a change in fluorescence, etc. The determination may be made by a person, or by an external apparatus able to analyze at least a portion of the device. In some cases, the determination may be made without removing blood from the device, e.g., from the storage chamber. (In other cases, however, blood or other fluid may first be removed from the device before being analyzed.) For example, the device may include one or more sensors (e.g., ion sensors such as K+ sensors, colorimetric sensors, fluorescence sensors, etc.), and/or contain "windows" that allow light to penetrate the device. The windows may be formed of glass, plastic, etc., and may be selected to be at least partially transparent to one or a range of suitable wavelengths, depending on the analyte or condition to be determined. As a specific example, the entire device (or a portion thereof) may be mounted in an external apparatus, and light from the external apparatus may pass through or otherwise interact with at least a portion of the device (e.g., be reflected or refracted via the device) to determine the analyte and/or the reaction entity.

In one aspect, the device may be interfaced with an external apparatus able to determine an analyte contained within a fluid in the device, for example within a storage chamber as discussed herein. For example, the device may be mounted on an external holder, the device may include a port for transporting fluid out of the device, the device may include a window for interrogating a fluid contained within the device, or the like. Examples may be seen in U.S. patent application Ser. No. 13/006,165 filed on Jan. 13, 2011, entitled "Sampling Device Interfaces," incorporated herein by reference in its entirety.

Thus, the device, in certain embodiments, may contain a portion able to determine a fluid received from the skin. For example, a portion of the device may contain a sensor, or reagents able to interact with an analyte contained or suspected to be present within the received fluid from the subject, for example, a marker for a disease state. The sensor may be embedded within or integrally connected to the device, or positioned remotely but with physical, electrical, and/or optical connection with the device so as to be able to sense a chamber within or fluid from the device. For example, the sensor may be in fluidic communication with fluid received from a subject, directly, via a microfluidic channel, an analytical chamber, etc. The sensor may be able to sense an analyte, e.g., one that is suspected of being in a fluid received from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a chamber within the device. As another example, a sensor may be positioned on or within the device, and may sense activity in a chamber by being connected optically to the chamber. Sensing communication can also be provided where the chamber is in communication with a sensor fluidly, optically or visually, thermally, pneumatically, electronically, or the like, so as to be able to sense a condition of the chamber. As one example, the sensor may be positioned downstream of a chamber, within a channel such a microfluidic channel, on an external apparatus, or the like. Thus, the invention provides, in certain embodiments, sensors able to determine an analyte. Such determination may occur within the skin, and/or externally of the subject, e.g., within a device on the surface of the skin, depending on the embodiment. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. The species may be, for example, a bodily fluid and/or an analyte suspected of being present in the bodily fluid. "Determining" also means detecting or quantifying interaction between species.

Non-limiting examples of sensors include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other suitable sensors. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

Examples of sensors include, but are not limited to, pH sensors, optical sensors, ion sensors, colorimetric sensors, a sensor able to detect the concentration of a substance, or the like, e.g., as discussed herein. For instance, in one set of embodiments, the device may include an ion selective electrode. The ion selective electrode may be able to determine a specific ion and/or ions such as K+, H+, Na+, Ag+, Pb2+, Cd2+, or the like. Various ion selective electrodes can be obtained commercially. As a non-limiting example, a potassium-selective electrode may include an ion exchange resin membrane, using valinomycin, a potassium channel, as the ion carrier in the membrane to provide potassium specificity.

Examples of analytes that the sensor may be used to determine include, but are not limited to, pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, e.g., legal prescription levels of drugs such as coumadin, other drugs such as nicotine, or illegal such as cocaine. Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever. Still other potentially suitable analytes include various pathogens such as bacteria or viruses, and/or markers produced by such pathogens.

As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the received fluid may be determined in some cases. Those of ordinary skill in the art will be aware of many suitable commercially-available sensors, and the specific sensor used may depend on the particular analyte being sensed. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasi-electric light scattering; polarimetry; refractometry; chemical indicators such as dyes; or turbidity measurements, including nephelometry.

In one set of embodiments, a sensor in the device may be used to determine a condition of the blood present within the device. For example, the sensor may indicate the condition of analytes commonly found within the blood, for example, O2, K+, hemoglobin, Na+, glucose, or the like. As a specific non-limiting example, in some embodiments, the sensor may determine the degree of hemolysis within blood contained within the device. Without wishing to be bound by any theory, it is believed that in some cases, hemolysis of red blood cells may cause the release of potassium ions and/or free hemoglobin into the blood. By determining the levels of potassium ions, and/or hemoglobin (e.g., by subjecting the device and/or the blood to separate cells from plasma, then determining hemoglobin in the plasma using a suitable colorimetric assay), the amount of blood lysis or "stress" experienced by the blood contained within the device may be determined. Accordingly, in one set of embodiments, the device may indicate the usability of the blood (or other fluid) contained within the device, e.g., by indicating the degree of stress or the amount of blood lysis. Other examples of devices suitable for indicating the usability of the blood (or other fluid) contained within the device are also discussed herein (e.g., by indicating the amount of time blood has been contained in the device, the temperature history of the device, etc.).

For instance, fluids received from the subject will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; H+ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. As discussed herein, certain embodiments of the present invention are generally directed at methods for receiving fluids from the body, and optionally determining one or more analytes within the received fluid. Thus, in some embodiments, at least a portion of the fluid may be stored, and/or analyzed to determine one or more analytes, e.g., a marker for a disease state, or the like. The fluid received from the skin may be subjected to such uses, and/or one or more materials previously delivered to the skin may be subject to such uses.

Still other potentially suitable analytes include various pathogens such as bacteria or viruses, and/or markers produced by such pathogens. Thus, in certain embodiments of the invention, as discussed below, one or more analytes within the pooled region of fluid may be determined in some fashion, which may be useful in determining a past, present and/or future condition of the subject.

In some embodiments, the device may connected to an external apparatus for determining at least a portion of the device, a fluid removed from the device, an analyte suspected of being present within the fluid, or the like. For example, the device may be connected to an external analytical apparatus, and fluid removed from the device for later analysis, or the fluid may be analyzed within the device in situ, e.g., by adding one or more reaction entities to the device, for instance, to a storage chamber, or to analytical chamber within the device. For example, in one embodiment, the external apparatus may have a port or other suitable surface for mating with a port or other suitable surface on the device, and blood or other fluid can be removed from the device using any suitable technique, e.g., using vacuum or pressure, etc. The blood may be removed by the external apparatus, and optionally, stored and/or analyzed in some fashion. For example, in one set of embodiments, the device may include an exit port for removing a fluid from the device (e.g., blood). In some embodiments, fluid contained within a storage chamber in the device may be removed from the device, and stored for later use or analyzed outside of the device. In some cases, the exit port may be separate from the substance transfer component. An example is shown with exit port 670 and substance transfer component 620 in device 600 in FIG. 6. As shown in this figure, the exit port can be in fluidic communication with vacuum chamber 610, which can also serve as a fluid reservoir in some cases.

In one set of embodiments, the device may include an anticoagulant or a stabilizing agent for stabilizing the fluid received from the skin. For example, the fluid may be stored within the device for a certain period of time, and/or the device (or a portion thereof) may be moved or shipped to another location for analysis or later use. For instance, a device may contain anticoagulant or a stabilizing agent in a storage chamber. In some cases, more than one anticoagulant may be used, e.g., in the same storage chamber, or in more than one storage chamber.

As a specific non-limiting example, an anticoagulant may be used for blood received from the skin. Examples of anticoagulants include, but are not limited to, heparin, citrate, thrombin, oxalate, ethylenediaminetetraacetic acid (EDTA), sodium polyanethol sulfonate, acid citrate dextrose. Other agents may be used in conjunction or instead of anticoagulants, for example, stabilizing agents such as solvents, diluents, buffers, chelating agents, antioxidants, binding agents, preservatives, antimicrobials, or the like. Examples of preservatives include, for example, benzalkonium chloride, chlorobutanol, parabens, or thimerosal. Non-limiting examples of antioxidants include ascorbic acid, glutathione, lipoic acid, uric acid, carotenes, alpha-tocopherol, ubiquinol, or enzymes such as catalase, superoxide dismutase, or peroxidases. Examples of microbials include, but are not limited to, ethanol or isopropyl alcohol, azides, or the like. Examples of chelating agents include, but are not limited to, ethylene glycol tetraacetic acid or ethylenediaminetetraacetic acid. Examples of buffers include phosphate buffers such as those known to ordinary skill in the art.

In one set of embodiments, at least a portion of the device may be colored to indicate the anticoagulant(s) contained within the device. In some cases, the colors used may be identical or equivalent to that commercially used for Vacutainers™, Vacuettes™, or other commercially-available phlebotomy equipment. For example, lavender and/or purple may indicate ethylenediaminetetraacetic acid, light blue may indicate citrate, dark blue may indicate ethylenediaminetetraacetic acid, green may indicate heparin, gray may indicate a fluoride and/or an oxalate, orange may indicate a thrombin, yellow may indicate sodium polyanethol sulfonate and/or acid citrate dextrose, black may indicate citrate, brown may indicate heparin, etc. In other embodiments, however, other coloring systems may be used.

Other coloring systems may be used in other embodiments of the invention, not necessarily indicative of anticoagulants. For example, in one set of embodiments, the device carries a color indicative of a recommended bodily use site for the device, e.g., a first color indicative of a device suitable for placement on the back, a second color indicative of a device suitable for placement on a leg, a third color indicative of a device suitable for placement on the arm, etc.

As mentioned, in one set of embodiments, a device of the invention as discussed herein may be shipped to another location for analysis. In some cases, the device may include an anticoagulant or a stabilizing agent contained within the device, e.g., within a storage chamber for the fluid. Thus, for example, fluid such as blood received from the skin may be delivered to a chamber (e.g., a storage chamber) within the device, then the device, or a portion of the device (e.g., a module) may be shipped to another location for analysis. Any form of shipping may be used, e.g., via mail.

Non-limiting examples of various devices of the invention are shown in FIG. 1. In FIG. 1A, device 90 is used for receiving a fluid from a subject when the device is placed on the skin of a subject. Device 90 includes sensor 95 and substance transfer component 92, e.g., including a needle, a microneedle, etc., as discussed herein. In fluidic communication with substance transfer component 92 via fluidic channel 99 is sensing chamber 97. In one embodiment, sensing chamber 97 may contain agents such as particles, enzymes, dyes, etc., for analyzing bodily fluids, such as interstitial fluid or blood. In some cases, fluid may be received using substance transfer component 92 by a vacuum, for example, a self-contained vacuum contained within device 90. Optionally, device 90 also contains a display 94 and associated electronics 93, batteries or other power supplies, etc., which may be used to display sensor readings obtained via sensor 95. In addition, device 90 may also optionally contain memory 98, transmitters for transmitting a signal indicative of sensor 95 to a receiver, etc.

In the example shown in FIG. 1A, device 90 may contain a vacuum source (not shown) that is self-contained within device 90, although in other embodiments, the vacuum source may be external to device 90. (In still other instances, other systems may be used to deliver and/or receive fluid from the skin, as is discussed herein.) In one embodiment, after being placed on the skin of a subject, the skin may be drawn upward into a recess of the substance transfer component 92, for example, upon exposure to the vacuum source. Access to the vacuum source may be controlled by any suitable method, e.g., by piercing a seal or a septum; by opening a valve or moving a gate, etc. For instance, upon activation of device 90, e.g., by the subject, remotely, automatically, etc., the vacuum source may be put into fluidic communication with the recess such that skin is drawn into the recess due to the vacuum. Skin drawn into the recess may come into contact with a skin insertion object (e.g., solid or hollow needles), which may, in some cases, pierce the skin and allow a fluid to be delivered and/or received from the skin. In another embodiment, a skin insertion object may be actuated and moved downward to come into contact with the skin, and optionally retracted after use.

Figure 1B:
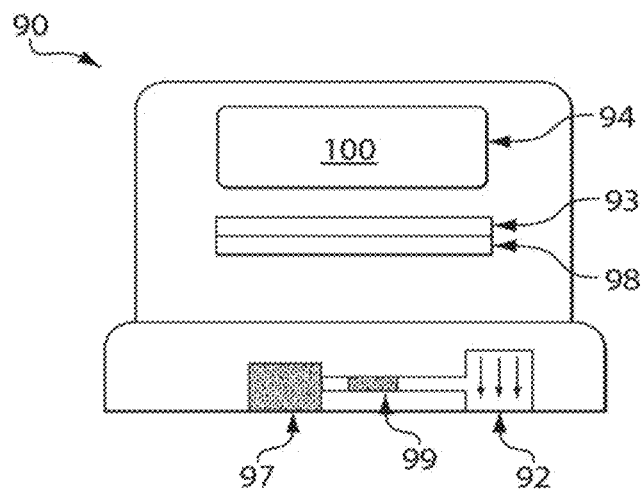

Another non-limiting example of a device is shown in FIG. 1B. This figure illustrates a device useful for delivering a fluid to the subject. Device 90 in this figure includes substance transfer component 92, e.g., including a needle, a microneedle, etc., as discussed herein. In fluidic communication with substance transfer component 92 via fluidic channel 99 is chamber 97, which may contain a drug or other agent to be delivered to the subject. In some cases, fluid may be delivered with a pressure controller, and/or received using substance transfer component 92 by a vacuum, for example, a self-contained vacuum contained within device 90. For instance, upon creating a vacuum, skin may be drawn up towards substance transfer component 92, and the substance transfer component 92 may pierce the skin. Fluid from chamber 97 can then be delivered into the skin through fluid channel 99 and substance transfer component 92. Optionally, device 90 also contains a display 94 and associated electronics 93, batteries or other power supplies, etc., which may be used control delivery of fluid to the skin. In addition, device 90 may also optionally contain memory 98, transmitters for transmitting a signal indicative of device 90 or fluid delivery to a receiver, etc.

Yet another non-limiting example of a device of the invention is shown in FIG. 2. FIG. 2A illustrates a view of the device (with the cover removed), while FIG. 2B schematically illustrates the device in cross-section. In FIG. 2B, device 50 includes a needle 52 contained within a recess 55. Needle 52 may be solid or hollow, depending on the embodiment. Device 50 also includes a self-contained vacuum chamber 60, which wraps around the central portion of the device where needle 52 and recess 55 are located. A channel 62 connects vacuum chamber 60 with recess 55, separated by a foil or a membrane 67. Also shown in device 50 is button 58. When pushed, button 58 breaks foil 67, thereby connecting vacuum chamber 50 with recess 55, creating a vacuum in recess 55. The vacuum may be used, for example, to draw skin into recess 55, preferably such that it contacts needle 52 and pierces the surface, thereby gaining access to an internal fluid. The fluid may be controlled, for example, by controlling the size of needle 52, and thereby the depth of penetration. For example, the penetration may be limited to the epidermis, e.g., to collect interstitial fluid, or to the dermis, e.g., to collect blood. In some cases, the vacuum may also be used to at least partially secure device 50 on the surface of the skin, and/or to assist in the receiving of fluid from the skin. For instance, fluid may flow into channel 62 under action of the vacuum, and optionally to sensor 61, e.g., for detection of an analyte contained within the fluid. For instance, sensor 61 may produce a color change if an analyte is present, or otherwise produce a detectable signal.

Other components may be added to the example of the device illustrated in FIG. 2, in some embodiments of the invention. For example, device 50 may contain a cover, displays, ports, transmitters, sensors, channels such as microfluidic channels, chambers, and/or various electronics, e.g., to control or monitor fluid transport into or out of device 50, to determine an analyte present within a fluid delivered and/or received from the skin, to determine the status of the device, to report or transmit information regarding the device and/or analytes, or the like, as is discussed in more detail herein. As another example, device 50 may contain an adhesive, e.g., on surface 54, for adhesion of the device to the skin.

Figure 2A:
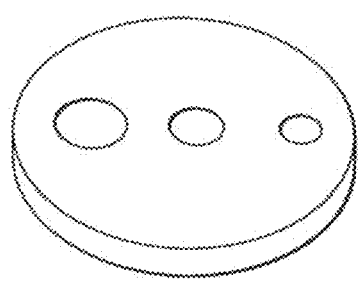
FIGS. 2A-2C illustrate devices according to various embodiments of the invention.
Figure 2B:
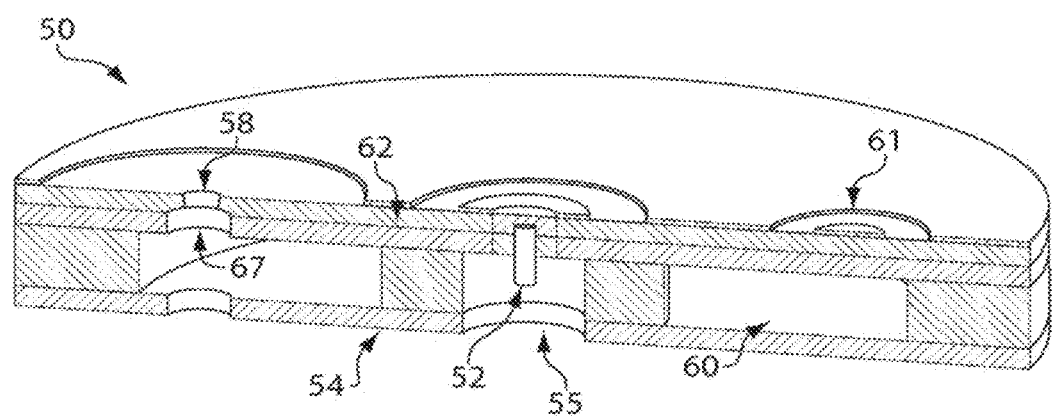
Figure 2C:
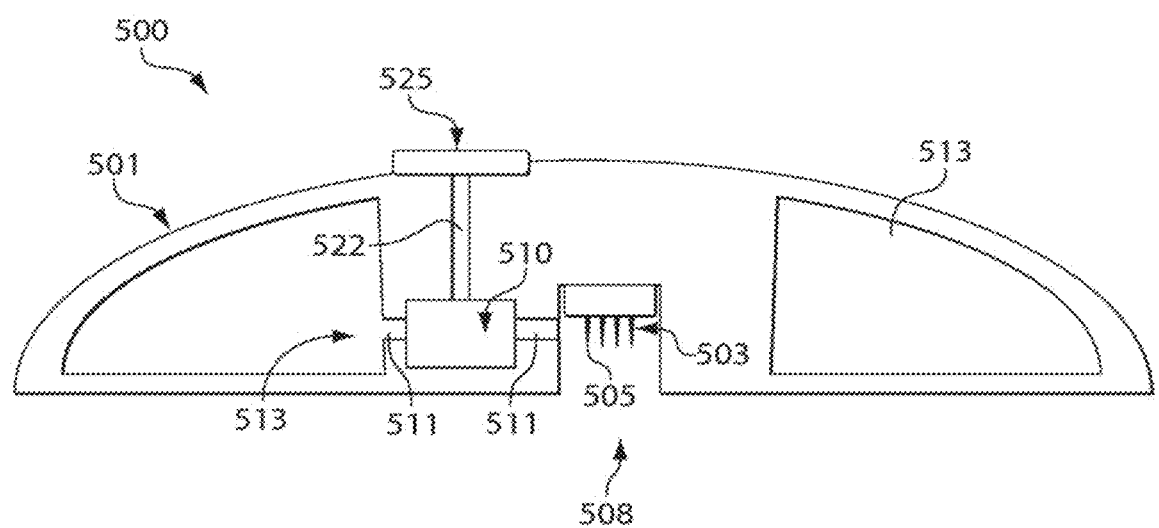

Yet another non-limiting example is illustrated with reference to FIG. 2C. In this example, device 500 includes a housing 501, and an associated substance transfer component 503. Substance transfer component 503 includes a plurality of needles or microneedles 505, although other skin insertion objects or flow activators as discussed herein may also be used. Also shown in FIG. 5 is sensor 510, connected via channels 511 to recess 508 containing needles or microneedles 505. Chamber 513 may be a self-contained vacuum chamber, and chamber 513 may be in fluidic communication with recess 508 via channel 511, for example, as controlled by a controller or an actuator (not shown). In this figure, device 500 also contains display 525, which is connected to sensor 510 via electrical connection 522. As an example of use of device 500, when fluid is drawn from the skin (e.g., blood, interstitial fluid, etc.), the fluid may flow through channel 511 to be determined by sensor 510, e.g., due to action of the vacuum from vacuum chamber 513. In some cases, the vacuum is used, for example, to draw skin into recess 508, preferably such that it contacts needles or microneedles 505 and pierces the surface of the skin to gain access to a fluid internal of the subject, such as blood or interstitial fluid, etc. The fluid may be controlled, for example, by controlling the size of needle 505, and thereby the depth of penetration. For example, the penetration may be limited to the epidermis, e.g., to collect interstitial fluid, or to the dermis, e.g., to collect blood. Upon determination of the fluid and/or an analyte present or suspected to be present within the fluid, a microprocessor or other controller may display on display 525 a suitable signal. As is discussed below, a display is shown in this figure by way of example only; in other embodiments, no display may be present, or other signals may be used, for example, lights, smell, sound, feel, taste, or the like.

In some cases, more than one substance transfer component may be present within the device. For instance, the device may be able to be used repeatedly, and/or the device may be able to deliver and/or receive fluid at more than one location on a subject, e.g., sequentially and/or simultaneously. In some cases, the device may be able to simultaneously deliver and receive fluid to and from a subject. A non-limiting example of a device having more than one substance transfer component is illustrated with reference to FIG. 2E. In this example, device 500 contains a plurality of structures such as those described herein for delivering and/or receiving fluid from a subject. For example, device 500 in this example contains 3 such units, although any number of units are possible in other embodiments. In this example, device 500 contains three such substance transfer components 575. Each of these substance transfer components may independently have the same or different structures, depending on the particular application, and they may have structures such as those described herein.

In some embodiments, the device may be an electrical and/or a mechanical device applicable or affixable to the surface of the skin, e.g., using adhesive, or other techniques such as those described herein. The adhesive may be permanent or temporary, and may be used to affix the device to the surface of the skin. The adhesive may be any suitable adhesive, for example, a pressure sensitive adhesive, a contact adhesive, a permanent adhesive, a hydrogel, a cyanoacrylate, a glue, a gum, hot melts, an epoxy, or the like. In some cases, the adhesive is chosen to be biocompatible or hypoallergenic.

In another set of embodiments, the device may be mechanically held to the skin, for example, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

As another example, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

Any or all of the arrangements described herein can be provided proximate a subject, for example on or proximate a subject's skin. Activation of the devices can be carried out in a variety of ways. In one embodiment, a device can be applied to a subject and a region of the device activated (e.g., pushed, pressed, or tapped by a user) to inject a needle or a microneedle so as to access interstitial fluid. The same or a different tapping or pushing action can activate a vacuum source, open and/or close one or more of a variety of valves, or the like. The device can be a simple one in which it is applied to the skin and operates automatically (where e.g., application to the skin accesses interstitial fluid and draws interstitial fluid into an analysis region) or the device can be applied to the skin and one tapping or other activation can cause fluid to flow through administration of a needle or a microneedle, opening of a valve, activation of vacuum, or any combination. Any number of activation protocols can be carried out by a user repeatedly pushing or tapping a location or selectively, sequentially, and/or periodically activating a variety of switches. In another arrangement, activation of needles or microneedles, creation of suction blisters, opening and/or closing of valves, and other techniques to facilitate one or more analysis can be carried out electronically or in other manners facilitated by the subject or by an outside controlling entity. For example, a device or patch can be provided proximate a subject's skin and a radio frequency, electromagnetic, or other signal can be provided by a nearby controller or a distant source to activate any of the needles, blister devices, valves or other components of the devices described so that any assay or assays can be carried out as desired.

In some embodiments, fluid may be delivered to the subject, and such fluids may contain materials useful for delivery, e.g., forming at least a portion of the fluid, dissolved within the fluid, carried by the fluid (e.g., suspended or dispersed), or the like. Examples of suitable materials include, but are not limited to, particles such as microparticles or nanoparticles, a chemical, a drug or a therapeutic agent, a diagnostic agent, a carrier, or the like.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

In some cases, fluids or other materials delivered to the subject may be used for indication of a past, present and/or future condition of the subject. Thus, the condition of the subject to be determined may be one that is currently existing in the subject, and/or one that is not currently existing, but the subject is susceptible or otherwise is at an increased risk to that condition. The condition may be a medical condition, e.g., diabetes or cancer, or other physiological conditions, such as dehydration, pregnancy, illicit drug use, or the like. In one set of embodiments, the materials may include a diagnostic agent, for example, one which can determine an analyte within the subject, e.g., one that is a marker for a disease state. As a specific non-limiting example, material delivered to the skin, e.g., to the dermis or epidermis, to a pooled region of fluid, etc., of a subject may include a particle including an antibody directed at a marker produced by bacteria. In other cases, however, the materials delivered to the subject may be used to determine conditions that are external to the subject. For example, the materials may contain reaction entities able to recognize pathogens or other environmental conditions surrounding the subject, for example, an antibody able to recognize an external pathogen (or pathogen marker). As a specific example, the pathogen may be anthrax and the antibody may be an antibody to anthrax spores. As another example, the pathogen may be a Plasmodia (some species of which causes malaria) and the antibody may be an antibody that recognizes the Plasmodia.

According to one aspect of the invention, the device is of a relatively small size. In some embodiments, the device may be sized such that it is wearable and/or carryable by a subject. For example, the device may be self-contained, needing no wires, cables, tubes, external structural elements, or other external support. The device may be positioned on any suitable position of the subject, for example, on the arm or leg, on the back, on the abdomen, etc. As mentioned, in some embodiments, the device may be affixed or held onto the surface of the skin using any suitable technique, e.g., using adhesives, mechanical elements such as straps, belts, buckles, strings, ties, elastic bands, or the like. In some cases, the device may be positioned on the subject such that the subject is able to move around (e.g., walking, exercising, typing, writing, drinking or eating, using the bathroom, etc.) while wearing the device. For example, the device may have a mass and/or dimensions such that the subject is able to wear the device for at least about 5 minutes, and in some cases for longer periods of time, e.g., at least about 10 minutes, at least about 15 minutes, at least about 30 minutes, at least about 45 minutes, at least about 1 hour, at least about 3 hours, at least 5 hours, at least about 8 hours, at least about 1 day, at least about 2 days, at least about 4 days, at least about 1 week, at least about 2 weeks, at least about 4 weeks, etc.

In some embodiments, the device is relatively lightweight. For example, the device may have a mass of no more than about 1 kg, no more than about 300 g, no more than about 150 g, no more than about 100 g, no more than about 50 g, no more than about 30 g, no more than about 25 g, no more than about 20 g, no more than about 10 g, no more than about 5 g, or no more than about 2 g. For instance, in various embodiments, the device has a mass of between about 2 g and about 25 g, a mass of between about 2 g and about 10 g, a mass of between 10 g and about 50 g, a mass of between about 30 g and about 150 g, etc.

The device, in some cases, may be relatively small. For example, the device may be constructed and arranged to lie relatively close to the skin. Thus, for instance, the device may have a largest vertical dimension, extending from the skin of the subject when the device is positioned on the skin, of no more than about 25 cm, no more than about 10 cm, no more than about 7 cm, no more than about 5 cm, no more than about 3 cm, no more than about 2 cm, no more than about 1 cm, no more than about 8 mm, no more than about 5 mm, no more than about 3 mm, no more than about 2 mm, no more than about 1 mm, or no more than about 0.5 mm. In some cases, the device may have a largest vertical dimension of between about 0.5 cm and about 1 cm, between about 2 and about 3 cm, between about 2.5 cm and about 5 cm, between about 2 cm and about 7 cm, between about 0.5 mm and about 7 cm, etc.

In another set of embodiments, the device may have a relatively small size. For example, the device may have a largest lateral dimension (e.g., parallel to the skin) of no more than about 25 cm, no more than about 10 cm, no more than about 7 cm, no more than about 5 cm, no more than about 3 cm, no more than about 2 cm, or no more than about 1 cm. In some cases, the device may have a largest lateral dimension of between about 0.5 cm and about 1 cm, between about 2 and about 3 cm, between about 2.5 cm and about 5 cm, between about 2 cm and about 7 cm, etc.

Combinations of these and/or other dimensions are also possible in other embodiments. As non-limiting examples, the device may have a largest lateral dimension of no more than about 5 cm, a largest vertical dimension of no more than about 1 cm, and a mass of no more than about 25 g; or the device may have a largest lateral dimension of no more than about 5 cm, a largest vertical dimension of no more than about 1 cm, and a mass of no more than about 25 g; etc.

In certain embodiments, the may also include a device actuator. The device actuator may be constructed and arranged to cause exposure of the substance transfer component to the skin upon actuation of the device actuator. For example, the activator may cause the substance transfer component to release a chemical to contact the skin, a microneedle or other substance transfer component to be driven into the skin, a vacuum to be applied to the skin, a jet of fluid to be directed to the skin, or the like. The device actuator may be actuated by the subject, and/or by another person (e.g., a health care provider), or the device itself may be self-actuating, e.g., upon application to the skin of a subject. The actuator may be actuated once, or multiple times in some cases.

The device may be actuated, for example, by pushing a button, pressing a switch, moving a slider, turning a dial, or the like. The subject, and/or another person, may actuate the actuator. In some cases, the device may be remotely actuated. For example, a health care provider may send an electromagnetic signal which is received by the device in order to activate the device, e.g., a wireless signal, a radio signal, etc.

In one set of embodiments, the device may include channels such as microfluidic channels, which may be used to deliver and/or receive fluids and/or other materials into or out of the skin, e.g., within the pooled region of fluid. In some cases, the microfluidic channels are in fluid communication with a substance transfer component that is used to deliver and/or receive fluids to or from the skin. For example, in one set of embodiments, the device may include a hypodermic needle that can be inserted into the skin, and fluid may be delivered into the skin via the needle and/or received from the skin via the needle. The device may also include one or more microfluidic channels to contain fluid for delivery to the needle, e.g., from a source of fluid, and/or to receive fluid from the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For example, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In some cases, the device may contain one or more chambers or reservoirs for holding fluid. In some cases, the chambers may be in fluidic communication with one or more substance transfer components and/or one or more microfluidic channels. For instance, the device may contain a chamber for collecting fluid received from a subject (e.g., for storage and/or later analysis), a chamber for containing a fluid for delivery to the subject (e.g., blood, saline, optionally containing drugs, hormones, vitamins, pharmaceutical agents, or the like), etc.

After receipt of the fluid into the device, the device, or a portion thereof, may be removed from the skin of the subject, e.g., by the subject or by another person. For example, the entire device may be removed, or a portion of the device containing the storage reservoir may be removed from the device, and optionally replaced with another storage reservoir. Thus, for instance, in one embodiment, the device may contain two or more modules, for example, a first module that is able to cause receiving of fluid from the skin into a storage reservoir, and a second module containing the storage module. In some cases, the module containing the storage reservoir may be removed from the device. Other examples of modules and modular systems are discussed below; other examples are discussed in U.S. Provisional Patent Application Ser. No. 61/256,931, filed Oct. 30, 2009, entitled "Modular Systems for Application to the Skin," incorporated by reference herein in its entirety.

The received fluid may then be sent to a clinical and/or laboratory setting, e.g., for analysis. In some embodiments, the entire device may be sent to the clinical and/or laboratory setting; in other embodiments, however, only a portion of the device (e.g., a module containing a storage reservoir containing the fluid) may be sent to the clinical and/or laboratory setting. In some cases, the fluid may be shipped using any suitable technique (e.g., by mail, by hand, etc.). In certain instances, the subject may give the fluid to appropriate personnel at a clinical visit. For instance, a doctor may prescribe a device as discussed above for use by the subject, and at the next doctor visit, the subject may give the doctor the received fluid, e.g., contained within a device or module.

In some aspects, the device may contain an indicator. The indicator may be used for determining a condition of a fluid contained within the device, e.g., within a fluid storage chamber or a fluid reservoir. In some embodiments, the indicator may indicate one or more conditions associated with the introduction of fluid into the storage component and/or one or more conditions associated with storage of fluid in the storage component. For example, the indicator may indicate the condition of blood or ISF within the device, e.g., as the device is being transported or shipped to a clinical or a laboratory setting. The indicator may indicate the condition of the blood through any suitable technique, e.g., visually (such as with a color change), using a display, by producing a sound, etc. For instance, the indicator may have a display that is green if the fluid has not been exposed to certain temperatures or if there is no adverse chemical reaction present within the fluid (e.g., a change in pH, growth of microorganisms, etc.), but is yellow or red if adverse conditions are or have been present (e.g., exposure to temperatures that are too extreme, growth of microorganisms, etc.). In other embodiments, the display may display a visual message, a sound may be produced by the device, or the like.

In some cases, the indicator may be activated upon the accessing of fluid by the access component and/or introduction of fluid into the storage component. In one set of embodiments, the indicator may be activated upon the introduction of fluid within a fluid storage reservoir, upon activation of the device (e.g., to receive fluid from a subject, as discussed below), upon activation by a user (e.g., by the subject, or another person), etc.

In some cases, the indicator may determine the condition of fluid within a fluid storage reservoir within the device using one or more suitable sensors, for example, pH sensors, temperature sensors (e.g., thermocouples), oxygen sensors, or the like. For instance, a sensor may be present within or proximate the fluid storage reservoir for determining the temperature of the fluid within the fluid storage reservoir. In some cases, for example, more than one sensor measurement may be taken, e.g., at multiple points of time or even continuously. In some cases, the indicator may also record the sensor determinations, e.g., for analysis or later study.

In certain embodiments, time information may be determined and/or recorded by the indicator. For example, the time fluid enters a fluid storage reservoir may be recorded, e.g., using a time/date stamp (e.g., absolute time), and/or using the duration of time that fluid has been present within the fluid storage reservoir. The time information may also be recorded in some embodiments.

As discussed, in one set of embodiments, information from sensors and/or time information may be used to determine a condition of the fluid within the fluid storage reservoir. For example, if certain limits are met or exceeded, the indicator may indicate that, as discussed above. As a specific non-limiting example, if the temperature of the device is too low (e.g., reaches 0° C.) or too high (e.g., reaches 100° C. or 37° C.), this may be displayed by a display on the indicator. Thus, fluid exposed to temperature extremes may be identified, e.g., as being problematic or spoiled. As a another non-limiting example, it may be desired to keep the pH of fluid within the device within certain conditions, and if the pH is exceeded (e.g., too acidic or too basic), this may be displayed by a display on the indicator, for example, if the pH is less than 6 or 5, or greater than 8 or 9. In some cases, the time that fluid is present within the device may be kept within certain limits as well, as another condition. For example, the indicator may indicate that fluid has been present within the device for more than about 12 hours, more than about 18 hours, or more than about 24 hours, which may indicate the fluid as being problematic, spoiled, etc.

In one set of embodiments, conditions such as these may also be combined (e.g., time and temperature). Thus, for example, fluid exposed to a first temperature may be allowed to be present within the device for a first time, while fluid exposed to a second temperature may be allowed to be present within the device for a second time, before the indicator displays this.

In some embodiments, the indicator may record and/or transmit sensor or time information. This may be recorded and/or transmitted using any suitable format. For instance, the information may be transmitted using a wireless signal, a radio signal, etc., or recorded on any suitable electronic media, e.g., on a microchip, flash drive, optically, magnetically, etc.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the Annual Review of Material Science, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the Annual Review of Biomedical Engineering, 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, MI, and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

As described herein, any of a variety of signaling or display methods, associated with analyses, can be provided including signaling visually, by smell, sound, feel, taste, or the like, in one set of embodiments. Signal structures or generators include, but are not limited to, displays (visual, LED, light, etc.), speakers, chemical-releasing chambers (e.g., containing a volatile chemical), mechanical devices, heaters, coolers, or the like. In some cases, the signal structure or generator may be integral with the device (e.g., integrally connected with a substance transfer component for application to the skin of the subject, e.g., such as a needle or a microneedle), or the signal structure may not be integrally connected with the substance transfer component. As used herein, a "signal structure" or a "signal generator" is any apparatus able to generate a signal that is related to a condition of a medium. For example, the medium may be a bodily fluid, such as blood or interstitial fluid.

In some embodiments, signaling methods such as these may be used to indicate the presence and/or concentration of an analyte determined by the sensor, e.g., to the subject, and/or to another entity, such as those described below.

Where a visual signal is provided, it can be provided in the form of change in opaqueness, a change in intensity of color and/or opaqueness, or can be in the form of a message (e.g., numerical signal, or the like), an icon (e.g., signaling by shape or otherwise a particular medical condition), a brand, logo, or the like. For instance, in one embodiment, the device may include a display. A written message such as "take next dose," or "glucose level is high" or a numerical value might be provided, or a message such as "toxin is present." These messages, icons, logos, or the like can be provided as an electronic read-out by a component of a device and/or can be displayed as in inherent arrangement of one or more components of the device.

In some embodiments, a device is provided where the device determines a physical condition of a subject and produces a signal related to the condition that can be readily understood by the subject (e.g., by provision of a visual "OK" signal as described above) or can be designed so as not to be readily understandable by a subject. Where not readily understandable, the signal can take a variety of forms. In one form, the signal might be a series of letters or numbers that mean nothing to the subject (e.g., A1278CDQ) which would have meaning to a medical professional or the like (and/or be decodable by the same, e.g., with reference to a suitable decoder) and can be associated with a particular physiological condition. Alternatively, a signal in the form of bar code can be provided by a device such that, under a particular condition or set of conditions the bar code appears and/or disappears, or changes, and can be read by a bar code reader to communicate information about the subject or analyte. In another embodiment, the device can be designed such that an ultraviolet signal is produced, or a signal that can be read only under ultraviolet light (e.g., a simple spot or patch, or any other signal such as a series of number, letters, bar code, message, or the like that can be readily understandable or not readily understandable by a subject) can be provided. The signal may be invisible to the human eye but, upon application UV light or other excitation energy, may be readable. The signal can be easily readable or understandable by a user via visual observation, or with other sensory activity such as smell, feel, etc. In another set of embodiments equipment as described above may be needed to determine a signal provided by the device, such as equipment in a clinical setting, etc. In some cases, the device is able to transmit a signal indicative of the analyte to a receiver, e.g., as a wireless signal, a radio signal, etc.

In some embodiments, quantitative and/or qualitative analyses can be provided by a device. That is, the device in some cases may provide analyses that allow "yes/no" tests or the like, or tests that provide information on the quantity, concentration, or level of a particular analyte or analytes. Display configurations can be provided by the invention that reflect the amount of a particular analyte present in a subject at a particular point in time, or any other variable (presence of analysis over time, type of analyte, etc.) display configurations can take a variety of forms. In one example, a dial can be provided, similar to that of a speedometer with a series of level indications (e.g., numbers around the dial) and a "needle" or other device that indicates a particular level. In other configurations, a particular area of the device (e.g., on a display) can exist that is filled in to a greater or lesser extent depending upon the presence and/or quantity of a particular analyte present, e.g., in the form of a bar graph. In another arrangement a "color wheel" can be provided where the amount of a particular analyte present can control which colors of the wheel are visible. Or, different analytes can cause different colors of a wheel or different bars of a graph to become visible or invisible in a multiple analyte analysis. Multiple-analyte quantitative analyses can be reflected in multiple color wheels, a single color wheel with different colors per analyte where the intensity of each color reflects the amount of the analyte, or, for example, a plurality of bar graphs where each bar graph is reflective of a particular analyte and the level of the bar (and/or degree to which an area is filled in with visible color or other visible feature) is reflective of the amount of the analyte. As with all embodiments here, whatever signal is displayed can be understandable or not understandable to any number of participants. For example, it can be understandable to a subject or not understandable to a subject. Where not understandable it might need to be decoded, read electronically, or the like. Where read electronically, for example, a device may provide a signal that is not understandable to a subject or not even visible or otherwise able to be sensed by a subject, and a reader can be provided adjacent or approximate the device that can provide a visible signal that is understandable or not understandable to the subject, or can transmit a signal to another entity for analysis.

In connection with any signals associated with any analyses described herein, another, potentially related signal or other display (or smell, taste, or the like) can be provided which can assist in interpreting and/or evaluating the signal. In one arrangement, a calibration or control is provided proximate (or otherwise easily comparable with) a signal, e.g., a visual calibration/control or comparator next to or close to a visual signal provided by a device and/or implanted agents, particles, or the like.

A visual control or reference can be used with another sensory signal, such as that of smell, taste, temperature, itch, etc. A reference/control and/or experimental confirmation component can be provided, to be used in connection with an in-skin test or vice versa. References/indicators can also be used to indicate the state of life of a device, changing color or intensity and/or changing in another signaling aspect as the device changes relative to its useful life, so that a user can determine when the device should no longer be relied upon and/or removed. For certain devices, an indicator or control can be effected by adding analyte to the control (e.g., from a source outside of the source to be determine) to confirm operability of the device and/or to provide a reference against which to measure a signal of the device. For example, a device can include a button to be tapped by a user which will allow an analyte from a reservoir to transfer to an indicator region to provide a signal, to demonstrate operability of the device and/or provide a comparator for analysis.

Many of the embodiments described herein involve a quantitative analysis and related signal, i.e., the ability to determine the relative amount or concentration of an analyte in a medium. This can be accomplished in a variety of ways. For example, where an agent (e.g. a binding partner attached to a nanoparticle) is used to capture and analyze an analyte, the agent can be provided in a gradient in concentration across a sensing region of the device. Or a sensing region can include a membrane or other apparatus through which analyte is required to flow or pass prior to capture and identification, and the pathway for analyte travel can vary as a function of position of display region. For example, a membrane can be provided across a sensing region, through which analyte must pass prior to interacting with a layer of binding and/or signaling agent, and the membrane may vary in thickness laterally in a direction related to "bar graph" readout. Where a small amount of analyte is present, it may pass through the thinner portion but not the thicker portion of the membrane, but where a larger amount is present, it may pass across a thicker portion. The boundary (where one exists) between a region through which analyte passes, and one through which it does not completely pass, can define the "line" of the bar graph. Other ways of achieving the same or a similar result can include varying the concentration of a scavenger or transporter of the analyte, or an intermediate reactive species (between analyte and signaling event), across a membrane or other article, gradient in porosity or selectivity of the membrane, ability to absorb or transport sample fluid, or the like. These principles, in combination with other disclosure herein, can be used to facilitate any or all of the quantitative analyses described herein.

In one set of embodiments, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered and/or received from the skin, based on a condition of the device, or the like. The signal may represent any suitable data or image. For example, the signal may represent the presence and/or concentration of an analyte in fluid received from a subject, the amount of fluid received from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in one set of embodiments, an image of the signal (e.g., a visual image or photograph) can be obtained and transmitted to a different entity (for example, a user can take a cell phone picture of a signal generated by the device and send it, via cell phone, the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. As signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch or other device can be worn by a subject to determine presence and/or amount of one or more analytes qualitatively, quantitatively, and/or over time. The subject can visit a clinician who can remove the patch (or other device) or a portion of the patch and attach it to a medical record associated with the subject.

According to various sets of embodiments, the device may be used once, or multiple times, depending on the application. For instance, obtaining samples for sensing, according to certain embodiments of the invention, can be done such that sensing can be carried out continuously, discretely, or a combination of these. For example, where a bodily fluid such as blood or interstitial fluid is accessed for determination of an analyte, fluid can be accessed discretely (i.e., as a single dose, once or multiple times), or continuously by creating a continuous flow of fluid which can be analyzed once or any number of times. Additionally, testing can be carried out once, at a single point in time, or at multiple points in time, and/or from multiple samples (e.g., at multiple locations relative to the subject).

Alternatively or in addition, testing can be carried out continuously over any number of points in time involving one or any number of locations relative to the subject or other multiple samples. As an example, one bolus or isolated sample, of fluid such as interstitial fluid can be obtained. From that fluid a test can be carried out to determine whether a particular analyte or other agent exists in the fluid. Alternatively, two or more tests can be carried out involving that quantity of fluid to determine the presence and/or quantity of two or more analytes, and any number of such tests can be carried out. Tests involving that quantity of fluid can be carried out simultaneously or over a period of time. For example, a test for a particular analyte can be carried out at various points in time to determine whether the result changes over time, or different analytes can be determined at different points in time.

In another example, a needle or a microneedle, or other device(s) can be used to access a fluid of a subject such as interstitial fluid. Fluid can be drawn to a point of analysis and analyzed in any manner described herein. For example, an analysis can be carried out once, to determine the presence and/or quantity of a single analyte, or a number of tests can be carried out. From a single sample of fluid, a particular test or number of tests can be carried out essentially simultaneously, or analyses can be carried out over time. Moreover, fluid can be drawn continuously from the subject and one or more tests can be carried out of any number of points in time. A variety of reasons for carrying out one or more tests over the course of time exists, as would be understood by those of ordinary skill in the art. One such reason is to determine whether the quantity or another characteristic of an analyte is constant in a subject, or changes over time. A variety of specific techniques for continuous and/or discrete testing will be described herein.

In one set of embodiments, one or more materials, such as particles, are delivered to the skin. Examples of suitable materials include, but are not limited to, particles such as microparticles or nanoparticles, a chemical, a drug or a therapeutic agent, a diagnostic agent, a carrier, or the like. The particles may be, for example, nanoparticles or microparticles, and in some cases, the particles may be anisotropic particles. In some cases, a plurality of particles may be used, and in some cases, some, or substantially all, of the particles may be the same. For example, at least about 10%, at least about 30%, at least about 40%, at least about 50%, at least about 60%, at least about 70%, at least about 80%, at least about 90%, at least about 95%, or at least about 99% of the particles may have the same shape, and/or may have the same composition.

The particles may be used for a variety of purposes. For instance, the particles may contain a diagnostic agent or a reaction entity able to interact with and/or associate with an analyte, or another reaction entity, or other particles. Such particles may be useful, for example, to determine one or more analytes, such as a marker of a disease state, as discussed below. As another example, the particles may contain a drug or a therapeutic agent, positioned on the surface and/or internally of the particles, which may be released by the particles and delivered to the subject. Specific examples of these and other embodiments are discussed in detail below.

In some cases, materials such as particles may become embedded within the skin, for example, due to physical properties of the materials (e.g., size, hydrophobicity, etc.). Thus, in some cases, a depot of material may be formed within the skin, and the depot may be temporary or permanent. For instance, materials within the depot may eventually degrade (e.g., if the material is biodegradable), enter the bloodstream, or be sloughed off to the environment, e.g., as the cells of the dermis differentiate to form new epidermis and accordingly push the material towards the surface of the skin. Thus, the depot of material may be present within the subject on a temporary basis (e.g., on a time scale of days or weeks), in certain instances.

As mentioned, certain aspects of the present invention are generally directed to particles such as anisotropic particles or colloids, which can be used in a wide variety of applications. For instance, the particles may be present within the skin, or externally of the skin, e.g., in a device on the surface of the skin. The particles may include microparticles and/or nanoparticles. As discussed above, a "microparticle" is a particle having an average diameter on the order of micrometers (i.e., between about 1 micrometer and about 1 mm), while a "nanoparticle" is a particle having an average diameter on the order of nanometers (i.e., between about 1 nm and about 1 micrometer. The particles may be spherical or non-spherical, in some cases. For example, the particles may be oblong or elongated, or have other shapes such as those disclosed in U.S. patent application Ser. No. 11/851,974, filed Sep. 7, 2007, entitled "Engineering Shape of Polymeric Micro- and Nanoparticles," by S. Mitragotri, et al.; International Patent Application No. PCT/US2007/077889, filed Sep. 7, 2007, entitled "Engineering Shape of Polymeric Micro- and Nanoparticles," by S. Mitragotri, et al., published as WO 2008/031035 on Mar. 13, 2008; U.S. patent application Ser. No. 11/272,194, filed Nov. 10, 2005, entitled "Multi-phasic Nanoparticles," by J. Lahann, et al., published as U.S. Patent Application Publication No. 2006/0201390 on Sep. 14, 2006; or U.S. patent application Ser. No. 11/763,842, filed Jun. 15, 2007, entitled "Multi-Phasic Bioadhesive Nan-Objects as Biofunctional Elements in Drug Delivery Systems," by J. Lahann, published as U.S. Patent Application Publication No. 2007/0237800 on Oct. 11, 2007, each of which is incorporated herein by reference.

Other examples of particles can be seen in U.S. patent application Ser. No. 11/272,194, filed Nov. 10, 2005, entitled "Multi-phasic Nanoparticles," by J. Lahann, et al., published as U.S. Patent Application Publication No. 2006/0201390 on Sep. 14, 2006; U.S. patent application Ser. No. 11/763,842, filed Jun. 15, 2007, entitled "Multi-Phasic Bioadhesive Nan-Objects as Biofunctional Elements in Drug Delivery Systems," by J. Lahann, published as U.S. Patent Application Publication No. 2007/0237800 on Oct. 11, 2007; or U.S. Provisional Patent Application Ser. No. 61/058,796, filed Jun. 4, 2008, entitled "Compositions and Methods for Diagnostics, Therapies, and Other Applications," by D. Levinson, each of which is incorporated herein by reference. Other examples of particles can be seen in U.S. patent application Ser. No. 11/272,194, filed Nov. 10, 2005, entitled "Multi-phasic Nanoparticles," by J. Lahann, et al., published as U.S. Patent Application Publication No. 2006/0201390 on Sep. 14, 2006; U.S. patent application Ser. No. 11/763,842, filed Jun. 15, 2007, entitled "Multi-Phasic Bioadhesive Nan-Objects as Biofunctional Elements in Drug Delivery Systems," by J. Lahann, published as U.S. Patent Application Publication No. 2007/0237800 on Oct. 11, 2007; or U.S. Provisional Patent Application Ser. No. 61/058,796, filed Jun. 4, 2008, entitled "Compositions and Methods for Diagnostics, Therapies, and Other Applications," by D. Levinson, each of which is incorporated herein by reference.

In some cases, a pooled region of fluid, such as a suction blister, may be formed in the skin to facilitate delivery and/or receiving of fluid from the skin. Thus, certain aspects of the present invention are generally directed to the creation of suction blisters or other pooled regions of fluid within the skin. In one set of embodiments, a pooled region of fluid can be created between the dermis and epidermis of the skin. Suction blisters or other pooled regions may form in a manner such that the suction blister or other pooled region is not significantly pigmented in some cases, since the basal layer of the epidermis contains melanocytes, which are responsible for producing pigments. Such regions can be created by causing the dermis and the epidermis to at least partially separate, and as will be discussed below, a number of techniques can be used to at least partially separate the dermis from the epidermis.

In one technique, a pool of interstitial fluid is formed between layers of skin of a subject and, after forming the pool, fluid is drawn from the pool by accessing the fluid through a layer of skin, for example, puncturing the outer layer of skin with a microneedle. Specifically, for example, a suction blister can be formed and then the suction blister can be punctured and fluid can be drawn from the blister. In another technique, an interstitial region can be accessed and fluid drawn from that region without first forming a pool of fluid via a suction blister or the like. For example, a microneedle or microneedles can be applied to the interstitial region and fluid can be drawn there from.

Pooled regions of fluids may be formed on any suitable location within the skin of a subject. Factors such as safety or convenience may be used to select a suitable location, as (in humans) the skin is relatively uniform through the body, with the exception of the hands and feet. As non-limiting examples, the pooled region may be formed on an arm or a leg, on the chest, abdomen, or the back of the subject, or the like. The size of the pooled region of fluid that is formed in the skin and/or the duration that the pooled region lasts within the skin depends on a variety of factors, such as the technique of creating the pooled region, the size of the pooled region, the size of the region of skin to which the technique is applied, the amount of fluid received from the pooled region (if any), any materials that are delivered into the pooled region, or the like. For example, if vacuum is applied to the skin to create a suction blister, the vacuum applied to the skin, the duration of the vacuum, and/or the area of the skin affected may be controlled to control the size and/or duration of the suction blister. In some embodiments, it may be desirable to keep the pooled regions relatively small, for instance, to prevent an unsightly visual appearance, to allow for greater sampling accuracy (due to a smaller volume of material), or to allow for more controlled placement of particles within the skin. For example, the volume of the pooled region may be kept to less than about 2 ml or less than about 1 ml in certain cases, or the average diameter of the pooled region (i.e., the diameter of a circle having the same area as the pooled region) may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm.

A variety of techniques may be used to cause pooled regions of fluid to form within the skin. In one set of embodiments, vacuum is applied to create a suction blister, or otherwise used to collect interstitial fluid from a subject. In other embodiments, however, other methods may be used to create as a pooled region of fluid within the skin besides, or in addition to, the use of vacuum. When vacuum (i.e., the amount of pressure below atmospheric pressure, such that atmospheric pressure has a vacuum of 0 mmHg, i.e., the pressure is gauge pressure rather than absolute pressure) is used to at least partially separate the dermis from the epidermis to cause the pooled region to form, the pooled region of fluid thus formed can be referred to as a suction blister. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg may be applied to the skin, e.g., to cause a suction blister and/or to collect interstitial fluid from a subject (as discussed, these measurements are negative relative to atmospheric pressure). Different amounts of vacuum may be applied to different subjects in some cases, for example, due to differences in the physical characteristics of the skin of the subjects.

The vacuum may be applied to any suitable region of the skin, and the area of the skin to which the vacuum may be controlled in some cases. For instance, the average diameter of the region to which vacuum is applied may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. In addition, such vacuums may be applied for any suitable length of time at least sufficient to cause at least some separation of the dermis from the epidermis to occur. For instance, vacuum may be applied to the skin for at least about 1 min, at least about 3 min, at least about 5 min, at least about 10 min, at least about 15 min, at least about 30 min, at least about 1 hour, at least about 2 hours, at least about 3 hours, at least about 4 hours, etc. Examples of devices suitable for creating such suction blisters are discussed in more detail below. In other cases, however, bodily fluids such as blood or interstitial fluid may be received from the skin using vacuum without the creation of a suction blister. Other non-limiting fluids include saliva, sweat, tears, mucus, plasma, lymph, or the like.

Other methods besides vacuum may be used to cause such separation to occur. For example, in another set of embodiments, heat may be used. For instance, a portion of the skin may be heated to at least about 40° C., at least about 50° C., at least about 55° C., or at least about 60° C., using any suitable technique, to cause such separation to occur. The skin may be heated, for instance, using an external heat source (e.g., radiant heat or a heated water bath), a chemical reaction, electromagnetic radiation (e.g., microwave radiation, infrared radiation, etc.), or the like. In some cases, the radiation may be focused on a relatively small region of the skin, e.g., to at least partially spatially contain the amount of heating within the skin that occurs.

In yet another set of embodiments, a separation chemical may be applied to the skin to at least partially cause separation of the dermis and the epidermis to occur. Non-limiting examples of such separation chemicals include proteases such as trypsin, purified human skin tryptase, or compound 48/80. Separation compounds such as these are commercially available from various sources. The separation chemical may be applied directly to the skin, e.g., rubbed into the surface of the skin, or in some cases, the separation chemical can be delivered into the subject, for example, between the epidermis and dermis of the skin. The separation chemical can, for example, be injected in between the dermis and the epidermis.

Another example of a separation chemical is a blistering agent, such as pit viper venom or blister beetle venom. Non-limiting examples of blistering agents include phosgene oxime, Lewisite, sulfur mustards (e.g., mustard gas or 1,5-dichloro-3-thiapentane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl)sulfide, bis(2-chloroethylthio)methane, bis(2-chloroethylthiomethyl)ether, or bis(2-chloroethylthioethyl)ether), or nitrogen mustards (e.g., bis(2-chloroethyl)ethylamine, bis(2-chloroethyl)methylamine, or tris(2-chloroethyl)amine).

In still another set of embodiments, a device may be inserted into the skin and used to mechanically separate the epidermis and the dermis, for example, a wedge or a spike. Fluids may also be used to separate the epidermis and the dermis, in yet another set of embodiments. For example, saline or another relatively inert fluid may be injected into the skin between the epidermis and the dermis to cause them to at least partially separate.

These and/or other techniques may also be combined, in still other embodiments. For example, in one embodiment, vacuum and heat may be applied to the skin of a subject, sequentially and/or simultaneously, to cause such separation to occur. As a specific example, in one embodiment, vacuum is applied while the skin is heated to a temperature of between about 40° C. and about 50° C.

Figure 9:
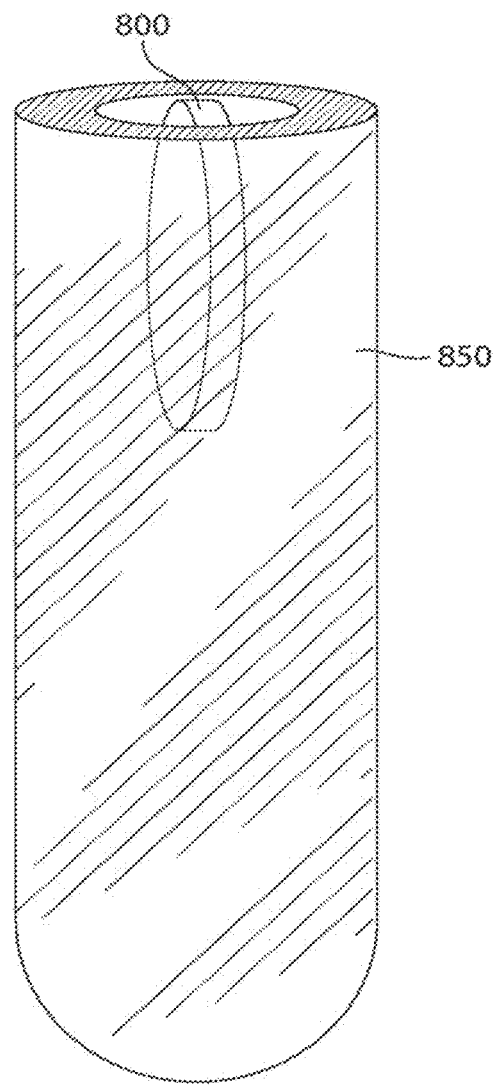
FIG. 9 illustrates an adaptor according to one embodiment of the invention.

One aspect of the present invention is directed to an adaptor able to position a device of the invention in apparatuses designed to contain Vacutainer™ tubes or Vacuette™ tubes. In some cases, the Vacutainer or Vacuette tube sizes have a maximum length of no more than about 75 mm or about 100 mm and a diameter of no more than about 16 mm or about 13 mm. In some cases, the adaptor may be able to immobilize a device of the invention therein, e.g., for subsequent use or processing. In some cases, as previously discussed, devices of the invention may have a largest lateral dimension of no more than about 50 mm, and/or a largest vertical dimension, extending from the skin of the subject when the device is applied to the subject, of no more than about 10 mm. An example of such a device is shown in FIG. 9, with device 800 contained within adapter 850. The device may contained within the adaptor using any suitable technique, e.g., using clips, springs, braces, bands, or the application of force to the device present within the adaptor.

Figure 2D:
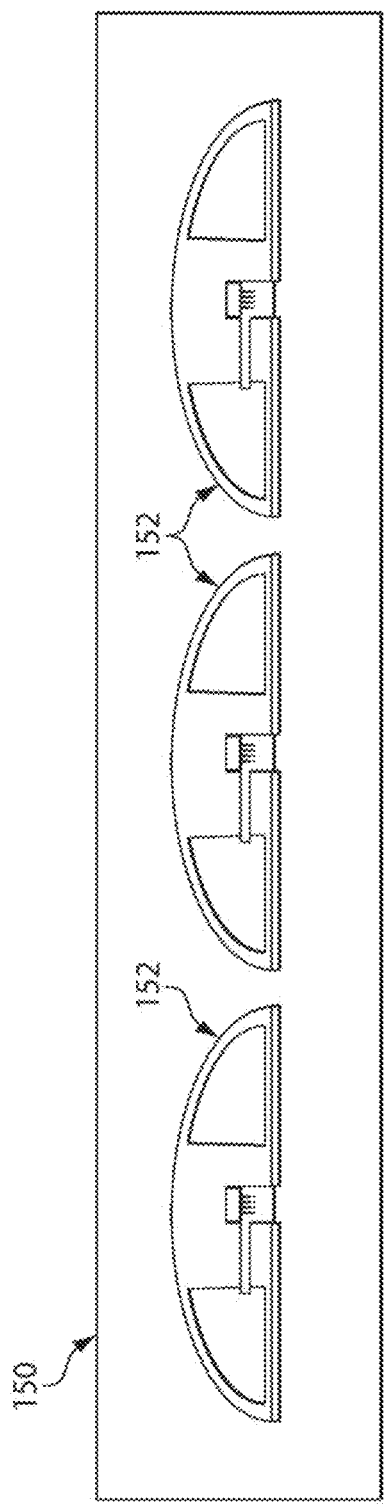
FIG. 2D illustrates a kit containing more than one device, in yet another embodiment of the invention.
Figure 2E:
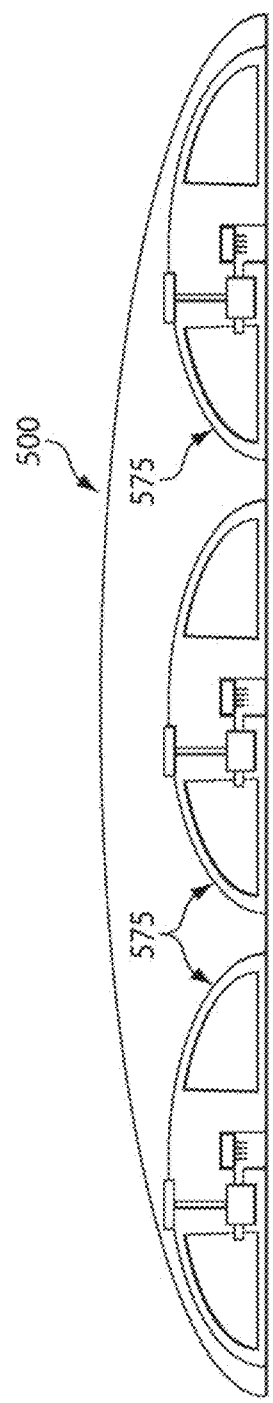
FIG. 2E illustrates a device according to still another embodiment of the invention.

In another aspect, the present invention is directed to a kit including one or more of the compositions previously discussed, e.g., a kit including a device for the delivery and/or receiving of fluid from the skin, a kit including a device able to create a pooled region of fluid within the skin of a subject, a kit including a device able to determine a fluid, or the like. An example of a kit containing more than one device of the invention is illustrated in FIG. 2D, with kit 150 containing devices 152. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. Provisional Patent Application Ser. No. 61/058,796, filed Jun. 4, 2008, entitled "Compositions and Methods for Diagnostics, Therapies, and Other Applications"; U.S. Provisional Patent Application Ser. No. 61/163,791, filed Mar. 26, 2009, entitled "Composition and Methods for Rapid One-Step Diagnosis"; U.S. Provisional Patent Application Ser. No. 61/163,793, filed Mar. 26, 2009, entitled "Compositions and Methods for Diagnostics, Therapies, and Other Applications"; U.S. patent application Ser. No. 12/478,756, filed Jun. 4, 2009, entitled "Compositions and Methods for Diagnostics, Therapies, and Other Applications"; International Patent Application No. PCT/US09/046333, filed Jun. 4, 2009, entitled "Compositions and Methods for Diagnostics, Therapies, and Other Applications"; U.S. Provisional Patent Application Ser. No. 61/163,710, filed Mar. 26, 2009, entitled "Systems and Methods for Creating and Using Suction Blisters or Other Pooled Regions of Fluid within the Skin"; U.S. Provisional Patent Application Ser. No. 61/163,733, filed Mar. 26, 2009, entitled "Determination of Tracers within Subjects"; U.S. Provisional Patent Application Ser. No. 61/163,750, filed Mar. 26, 2009, entitled "Monitoring of Implants and Other Devices"; U.S. Provisional Patent Application Ser. No. 61/154,632, filed Mar. 2, 2009, entitled "Oxygen Sensor"; and U.S. Provisional Patent Application Ser. No. 61/269,436, filed Jun. 24, 2009, entitled "Devices and Techniques associated with Diagnostics, Therapies, and Other Applications, Including Skin-Associated Applications." Also incorporated by reference herein are U.S. Provisional Patent Application Ser. No. 61/263,882, filed Nov. 24, 2009, entitled "Patient-Enacted Sampling Technique"; U.S. Provisional Patent Application Ser. No. 61/294,543, filed Jan. 13, 2010, entitled "Blood Sampling Device and Method"; U.S. patent application Ser. No. 12/716,222, filed Mar. 2, 2010, entitled "Oxygen Sensor," by Levinson, et al.; U.S. patent application Ser. No. 12/716,233, filed Mar. 2, 2010, entitled "Systems and Methods for Creating and Using Suction Blisters or Other Pooled Regions of Fluid within the Skin," by Levinson, et al.; U.S. patent application Ser. No. 12/716,226, filed Mar. 2, 2010, entitled "Techniques and Devices Associated with Blood Sampling," by Levinson, et al.; and U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al; U.S. Provisional Patent Application Ser. No. 61/256,880, filed Oct. 30, 2009, entitled "Systems and Methods for Altering or Masking Perception of Treatment of a Subject," by Chickering, et al.; U.S. Provisional Patent Application Ser. No. 61/256,874, filed Oct. 30, 2009, entitled "Systems and Methods for Application to Skin and Control of Use Thereof," by Benstein, et al.; U.S. Provisional Patent Application Ser. No. 61/256,871, filed Oct. 30, 2009, entitled "Packaging Systems and Methods for Devices Applied to the Skin," by Bernstein, et al.; U.S. Provisional Patent Application Ser. No. 61/334,533, filed May 13, 2010, entitled "Blood Sampling Device and Method," by Chickering, et al.; U.S. Provisional Patent Application Ser. No. 61/334,529, filed May 13, 2010, entitled "Sampling Device Interfaces," by Chickering, et al.; and U.S. patent application Ser. No. 13/006,165, filed Jan. 13, 2011, entitled "Sampling Device Interfaces" by Chickering, et al.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A microneedle structure comprising:
an annular ring having an inner circumference and an outer circumference; and
a first plurality of microneedles that each includes a base portion and a penetrating portion, the base portions of the first plurality of microneedles lying in a plane and arranged in a circular configuration at the outer circumference of the annular ring, the penetrating portions of the first plurality of microneedles extending in a direction perpendicular to the plane.

2. The structure of claim 1, wherein each of the first plurality of microneedles has a bend between the base portion and the penetrating portion.

3. The structure of claim 1, wherein the penetrating portions each include a proximal portion and an opposing distal portion, the proximal portion extending from the base portion and the distal portion comprising a point.

4. The structure of claim 3, wherein the point is formed at an intersection of at least four surfaces of the penetrating portion.

5. The structure of claim 1, further comprising:
a second plurality of microneedles that each includes a base portion and a penetrating portion, the base portions of the second plurality of microneedles being arranged in a circular configuration at the inner circumference of the annular ring, the penetrating portions of the second plurality of microneedles each extending in a direction perpendicular to the plane.

6. The structure of claim 1, wherein a packing density of the microneedles is at least 2 microneedles per square millimeter.

7. The structure of claim 1, wherein the penetrating portion is arranged to pierce human skin and extend at least 100 microns into the skin.

8. The structure of claim 1, wherein the microneedles have a combined skin-penetration area of at least about 500 square nanometers.

9. The structure of claim 1, wherein each penetrating portion has a sword shape with a symmetrical V-type knife edge at a periphery of the penetrating portion.

10. The structure of claim 1, wherein at least some of the microneedles are coated with a substance.

11. The structure of claim 10, wherein the substance comprises one or more of lidocaine, bupivacaine, and tetracaine.

12. A device for receiving fluid from a subject, comprising:
the microneedle structure of claim 1;
a device actuator; and
a housing including an opening to receive fluid into the housing,
wherein actuation of the device actuator moves the first plurality of microneedles relative to the housing.

13. The device of claim 12, further comprising a deployment actuator to move the first plurality of microneedles in a deployment direction toward or through the opening, the deployment actuator being configured to move the first plurality of microneedles in the deployment direction in response to actuation of the device actuator.

14. The device of claim 12, further comprising a storage chamber for receiving the fluid.

15. The device of claim 12, further comprising a retraction actuator to move the first plurality of microneedles in a retraction direction away from the opening, the retraction actuator being configured to move the first plurality of microneedles in the retraction direction in response to actuation of the device actuator.

16. The structure of claim 1, further comprising empty space within the annular ring.

17. A method for forming a microneedle structure, comprising:
providing a layer of material having opposed substantially planar sides;
etching the layer of material to define an annular ring having an inner circumference and an outer circumference and a first plurality of microneedles each having a base portion and a penetrating portion, the base portions of the first plurality of microneedles lying in a plane and arranged in a circular configuration at the outer circumference of the annular ring; and
bending the penetrating portions of the first plurality of microneedles upwardly from the plane such that the penetrating portions extend in a direction perpendicular to the plane.

18. The method of claim 17, wherein the step of etching includes isotropic etching of the layer of material.

19. The method of claim 17, further comprising:
exposing both sides of the layer of material, separately or simultaneously, to etching conditions, such that the steps of etching occurs on both sides of the layer of material.

20. The method of claim 17, wherein prior to bending the penetrating portions of the first plurality of microneedles upwardly from the plane, the penetrating portions of the first plurality of microneedles extend away from a center of the annular ring.

21. The method of claim 17, wherein each of the penetrating portions includes a point formed at an intersection of at least four surfaces.

22. The method of claim 17, further comprising:
etching the layer of material to define a second plurality of microneedles, each of the second plurality of microneedles including a base portion and a penetrating portion, the base portions of the second plurality of microneedles being arranged in a circular configuration at the inner circumference of the annular ring.

* * * * *